United States Patent
Satterfield et al.

(10) Patent No.: US 10,405,547 B2
(45) Date of Patent: *Sep. 10, 2019

(54) SUBSTITUTED CYCLIC AMIDES AS HERBICIDES

(71) Applicant: FMC Corporation, Philadelphia, PA (US)

(72) Inventors: Andrew Duncan Satterfield, Furlong, PA (US); James Francis Bereznak, Newtown Square, PA (US); Andrew Edmund Taggi, New Hope, PA (US)

(73) Assignee: FMC CORPORATION, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/560,612

(22) PCT Filed: Mar. 29, 2016

(86) PCT No.: PCT/US2016/024669
§ 371 (c)(1),
(2) Date: Sep. 22, 2017

(87) PCT Pub. No.: WO2016/164201
PCT Pub. Date: Oct. 13, 2016

(65) Prior Publication Data
US 2018/0049437 A1    Feb. 22, 2018

Related U.S. Application Data

(60) Provisional application No. 62/145,598, filed on Apr. 10, 2015.

(51) Int. Cl.
| | | |
|---|---|---|
| A01N 43/36 | (2006.01) | |
| C07D 403/12 | (2006.01) | |
| A01N 43/40 | (2006.01) | |
| C07D 401/10 | (2006.01) | |
| C07D 403/10 | (2006.01) | |
| C07D 405/10 | (2006.01) | |

(Continued)

(52) U.S. Cl.
CPC ............ *A01N 43/36* (2013.01); *A01N 37/18* (2013.01); *A01N 43/40* (2013.01); *A01N 43/56* (2013.01); *A01N 43/66* (2013.01); *A01N 43/713* (2013.01); *A01N 63/00* (2013.01); *C07D 207/277* (2013.01); *C07D 211/36* (2013.01); *C07D 401/10* (2013.01); *C07D 403/10* (2013.01); *C07D 403/12* (2013.01); *C07D 405/10* (2013.01); *C07D 405/12* (2013.01); *C07D 413/10* (2013.01); *C07D 413/12* (2013.01); *C07D 417/10* (2013.01); *C07D 417/12* (2013.01); *C07D 471/04* (2013.01); *A01N 43/80* (2013.01)

(58) Field of Classification Search
CPC .............. C07D 207/277; C07D 211/36; C07D 211/76; C07D 211/78; C07D 401/04; C07D 401/10; C07D 403/10; C07D 403/12; C07D 405/10; C07D 405/152; C07D 413/10; C07D 413/12; C07D 417/04; C07D 417/10; C07D 417/12; C07D 471/04; A01N 37/18; A01N 43/36; A01N 43/40; A01N 43/56; A01N 43/66; A01N 43/713; A01N 43/80; A01N 47/36; A01N 47/38; A01N 63/00

See application file for complete search history.

(56) References Cited

U.S. PATENT DOCUMENTS

| | | |
|---|---|---|
| 3,741,989 A | 6/1973 | Zaugg |
| 4,594,094 A | 6/1986 | Kollmeyer |

(Continued)

FOREIGN PATENT DOCUMENTS

| | | |
|---|---|---|
| CN | 102531918 B | 10/2013 |
| DE | 1262277 B | 3/1968 |

(Continued)

OTHER PUBLICATIONS

XP002734980; Jan. 20, 2002.

(Continued)

*Primary Examiner* — John Pak
*Assistant Examiner* — Nathan W Schlientz
(74) *Attorney, Agent, or Firm* — Reed A Coats

(57) ABSTRACT

Disclosed are compounds of Formula 1, including all stereoisomers, N-oxides, and salts thereof,

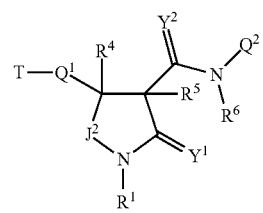

wherein $R^1$, $R^4$, $R^5$, $R^6$, $Q^1$, $Q^2$, $Y^1$, and $Y^2$ are as defined in the disclosure; and T is $J^1$-A- and also as defined in the disclosure.

Also disclosed are compositions containing the compounds of Formula 1 and methods for controlling undesired vegetation comprising contacting the undesired vegetation or its environment with an effective amount of a compound or a composition of the invention.

15 Claims, No Drawings

(51) Int. Cl.

| | |
|---|---|
| *C07D 405/12* | (2006.01) |
| *C07D 413/10* | (2006.01) |
| *C07D 413/12* | (2006.01) |
| *C07D 417/10* | (2006.01) |
| *C07D 417/12* | (2006.01) |
| *C07D 471/04* | (2006.01) |
| *C07D 207/277* | (2006.01) |
| *A01N 43/56* | (2006.01) |
| *A01N 43/66* | (2006.01) |
| *A01N 43/713* | (2006.01) |
| *A01N 37/18* | (2006.01) |
| *A01N 63/00* | (2006.01) |
| *C07D 211/36* | (2006.01) |
| *A01N 43/80* | (2006.01) |

(56) References Cited

U.S. PATENT DOCUMENTS

| | | | |
|---|---|---|---|
| 4,874,422 | A | 10/1989 | Woolard |
| 7,205,318 | B2 | 4/2007 | Qiao et al. |
| 8,293,926 | B2 | 10/2012 | Yasuoka et al. |
| 8,461,202 | B2 | 6/2013 | Sancho Sanz et al. |
| 8,575,154 | B2 | 11/2013 | Kori et al. |
| 8,946,216 | B2 | 2/2015 | Deng et al. |
| 9,944,602 | B2 * | 4/2018 | Satterfield ............ C07D 211/78 |
| 2004/0242671 | A1 | 12/2004 | Grimee et al. |
| 2006/0019831 | A1 | 1/2006 | Reinhard et al. |
| 2007/0123508 | A1 | 5/2007 | Olsson et al. |
| 2011/0218199 | A1 | 9/2011 | Georges et al. |
| 2016/0137639 | A1 | 5/2016 | Kotoku et al. |
| 2016/0289228 | A1 | 10/2016 | Defays et al. |
| 2016/0297756 | A1 | 10/2016 | Satterfield et al. |
| 2017/0158638 | A1 | 6/2017 | Satterfield et al. |
| 2018/0057442 | A1 | 3/2018 | Satterfield |
| 2018/0077931 | A1 | 3/2018 | Stevenson et al. |
| 2018/0099935 | A1 | 4/2018 | Satterfield et al. |
| 2018/0141904 | A1 | 5/2018 | Satterfield et al. |
| 2018/0213788 | A1 | 8/2018 | Satterfield et al. |
| 2018/0215760 | A1 | 8/2018 | Campbell et al. |

FOREIGN PATENT DOCUMENTS

| | | |
|---|---|---|
| EP | 2336104 A1 | 6/2011 |
| IN | 1462DEL08 | 6/2008 |
| JP | 53-056288 A | 5/1978 |
| JP | 54-088114 A | 7/1979 |
| JP | 08-269145 A | 10/1996 |
| KR | 20130142477 A | 12/2013 |
| RU | 2555370 C1 | 7/2015 |
| WO | 2000/09481 A1 | 2/2000 |
| WO | 2004/046081 A1 | 6/2004 |
| WO | 2006/081562 A2 | 8/2006 |
| WO | 2009/062371 A1 | 5/2009 |
| WO | 2015/084796 A1 | 6/2015 |
| WO | 2016/003997 A1 | 1/2016 |
| WO | 2016/094117 A1 | 6/2016 |
| WO | 2016/176082 A1 | 11/2016 |
| WO | 2016/182780 A1 | 11/2016 |
| WO | 2016/196019 A1 | 12/2016 |
| WO | 2016/196593 A1 | 12/2016 |
| WO | 2017/023515 A1 | 2/2017 |
| WO | 2018/118384 A1 | 6/2018 |
| WO | 2018/175226 A1 | 9/2018 |
| WO | 2018/175231 A1 | 9/2018 |

OTHER PUBLICATIONS

XP002734981; WO0009481; Feb. 24, 2000.
XP002759805; Jan. 20, 2002.
XP002759806; Mar. 23, 2009.
Murata et al.; "Oxidation of N-Acyl-Pyrrolidines and -Piperidines with Iron(II)-Hydrogen Peroxide and an Iron Complex-Molecular Oxygen"; *J. Chem. Soc. Perkin Trans.*; 1987; 1259-1262. (XP055297105).
Cauliez et al.; "Studies on Pyrrolidinones. On the Carbamoylation of Some Pyroglutamic Derivatives"; *J. Het. Chem.*; 33; 1996; 1233-1237. (XP055297107).
Hwang et al.; "Diastereoselective Synthesis of Oxazolidinone Derivatives and Their Antifungal Activities"; *Korean J. of Med. Chem.*; vol. 4, No. 1; 1994; 52-56. (XP009191451).
Campaigne et el.; Synthesis of Some Ureidodihydrofurans and Related Pyrimidones as Potential Antimalarials; *J. Med. Chem.*; 1969; 339-342. (XP002278920).
IPCOM000241978D; Jun. 11, 2015.
PubChem CID 29937915; May 28, 2009.

* cited by examiner

SUBSTITUTED CYCLIC AMIDES AS HERBICIDES

FIELD OF THE INVENTION

This invention relates to certain substituted cyclic amides, their N-oxides and salts, and compositions and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1 (including all stereoisomers), N-oxides and salts thereof, agricultural compositions containing them and their use as herbicides:

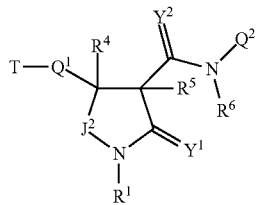

1 wherein

Q$^1$ is a phenyl ring or a naphthalenyl ring system, each ring or ring system optionally substituted with 1 to 4 substituents independently selected from R$^7$; or a 5- to 6-membered heteroaromatic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from S(=O)$_u$(=NR$^8$)$_v$, each ring or ring system optionally substituted with up to 4 substituents independently selected from R$^7$ on carbon atom ring members and selected from R$^9$ on nitrogen atom ring members;

Q$^2$ is a phenyl ring or a naphthalenyl ring system, each ring or ring system optionally substituted with up to 5 substituents independently selected from R$^{10}$; or a 5- to 6-membered heteroaromatic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from S(=O)$_u$(=NR$^8$)$_v$, each ring or ring system optionally substituted with up to 5 substituents independently selected from R$^{10}$ on carbon atom ring members and selected from R$^{11}$ on nitrogen atom ring members;

T is J$^1$-A-, wherein the free bond projecting to the right next to A indicates the connecting point of J$^1$-A- to Q$^1$; or T is R$^{17}$ON=CR$^{17a}$—, (R$^{18}$)$_2$C=NO—, (R$^{19}$)$_2$NN=CR$^{17a}$—, (R$^{18}$)$_2$C=NNR$^{20a}$, R$^{20}$N=CR$^{17a}$—, (R$^{18}$)$_2$C=N—, R$^{17}$ON=CR$^{17a}$C(R$^{23b}$)$_2$— or (R$^{18}$)$_2$C=NOC(R$^{24a}$)$_2$— wherein the free bond projecting to the right indicates the connecting point to Q$^1$;

A is a saturated, partially unsaturated or fully unsaturated chain containing 1 to 3 atoms selected from up to 3 carbon, up to 1 O, up to 1 S and up to 2 N atoms, the chain optionally substituted with up to 2 substituents independently selected from R$^{15}$ on carbon atoms and R$^{16}$ on nitrogen atoms;

Y$^1$ and Y$^2$ are each independently O, S or NR$^{12}$;

J$^1$ is a phenyl ring or a naphthalenyl ring system, each ring or ring system optionally substituted with up to 5 substituents independently selected from R$^{7'}$; or a 4- to 6-membered heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from S(=O)$_u$(=NR$^8$)$_v$, each ring or ring system optionally substituted with up to 5 substituents independently selected from R$^{7'}$ on carbon atom ring members and selected from R$^{9'}$ on nitrogen atom ring members; or C$_4$-C$_{10}$ cycloalkylalkoxy, C$_4$-C$_{10}$ cycloalkylalkyl, C$_2$-C$_8$ alkenyloxy, C$_2$-C$_8$ haloalkenyloxy, C$_2$-C$_8$ alkoxyalkoxy, C$_2$-C$_8$ alkylthioalkyl, C$_2$-C$_8$ alkylsulfinylalkyl, C$_2$-C$_8$ alkylsulfonylalkyl, C$_1$-C$_8$ alkylsulfonyloxy, C$_1$-C$_8$ haloalkylsulfonyloxy, C$_1$-C$_8$ alkylthio, C$_1$-C$_8$ haloalkylthio, C$_3$-C$_8$ cycloalkylthio, C$_1$-C$_8$ alkylsulfinyl, C$_1$-C$_8$ haloalkylsulfinyl, C$_1$-C$_8$ alkylsulfonyl, C$_1$-C$_8$ haloalkylsulfonyl, C$_2$-C$_8$ alkynyl, C$_2$-C$_8$ haloalkynyl, C$_2$-C$_8$ alkoxyalkyl, C$_2$-C$_8$ haloalkoxyalkyl, C$_3$-C$_8$ haloalkoxyalkoxy, C$_2$-C$_8$ haloalkoxyhaloalkyl, C$_1$-C$_8$ haloalkyl, C$_3$-C$_8$ halocycloalkyl, C$_2$-C$_8$ alkylcarbonyloxy or C$_2$-C$_8$ haloalkylcarbonyloxy;

J$^2$ is —CR$^2$R$^3$— or —CR$^2$R$^3$—CR$^{2a}$R$^{3a}$— wherein —CR$^2$R$^3$— moiety is connected to N;

R$^1$ is H, hydroxy, amino, cyano, formyl, C$_3$-C$_8$ alkylcarbonylalkyl, —CPh=N—O(C$_1$-C$_4$ alkyl), —C(C$_1$-C$_4$ alkyl)=N—O(C$_1$-C$_4$ alkyl), —C(O)NH$_2$, C$_1$-C$_6$ alkyl, C$_1$-C$_6$ haloalkyl, C$_2$-C$_6$ alkenyl, C$_3$-C$_6$ alkynyl, C$_2$-C$_6$ cyanoalkyl, C$_3$-C$_6$ cycloalkyl, C$_4$-C$_8$ cycloalkylalkyl, C$_2$-C$_8$ alkoxyalkyl, C$_3$-C$_8$ alkoxyalkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_2$-C$_8$ haloalkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkoxy, C$_1$-C$_6$ alkylthio, C$_1$-C$_6$ haloalkylthio, C$_3$-C$_8$ cycloalkylthio, C$_1$-C$_6$ alkylsulfinyl, C$_1$-C$_6$ haloalkylsulfinyl, C$_3$-C$_8$ cycloalkylsulfinyl, C$_1$-C$_6$ alkylsulfonyl, C$_1$-C$_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl, phenylcarbonyl or $G^1$;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^{2a}$ and $R^{3a}$ are each independently H, halogen or $C_1$-$C_4$ alkyl; or $R^{2a}$ and $R^{3a}$ are taken together with the carbon atom to which they are bonded to form a $C_3$-$C_7$ cycloalkyl ring;

$R^4$ and $R^5$ are each independently H, halogen, hydroxyl, $C_1$-$C_4$ alkoxy or $C_1$-$C_4$ alkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^7$ is independently halogen, hydroxyl, cyano, nitro, $C_1$-$C_4$ alkyl, $C_1$-$C_4$ cyanoalkyl, $C_1$-$C_4$ cyanoalkoxy, $C_1$-$C_4$ haloalkyl, $C_2$-$C_4$ alkenyl, $C_2$-$C_4$ haloalkenyl $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_3$-$C_8$ alkoxyalkoxyalkyl, $C_2$-$C_4$ haloalkoxyalkyl, $C_3$-$C_4$ cycloalkyl, $C_3$-$C_4$ halocycloalkyl, cyclopropylmethyl, 1-methylcyclopropyl, 2-methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, —CHO, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, amino, $C_1$-$C_4$ alkylamino, $C_2$-$C_4$ dialkylamino, formylamino, $C_2$-$C_4$ alkylcarbonylamino, —SF$_5$, —SCN, $C_3$-$C_4$ trialkylsilyl, trimethylsilylmethyl or trimethylsilylmethoxy; or two adjacent $R^7$ are taken together along with the carbon atoms to which they are bonded to form a $C_3$-$C_7$ cycloalkyl ring;

each $R^{10}$ is independently halogen, hydroxyl, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_4$ alkoxyalkyl, $C_3$-$C_8$ alkoxyalkoxyalkyl, $C_1$-$C_4$ cyanoalkyl, $C_1$-$C_4$ cyanoalkoxy, $C_2$-$C_8$ haloalkenyl, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, hydroxy, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, amino, $C_1$-$C_8$ alkylamino, $C_1$-$C_6$ haloalkylamino, $C_3$-$C_8$ cycloalkylamino, $C_2$-$C_8$ dialkylamino, $C_2$-$C_8$ halodialkylamino, formylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, —SF$_5$, —SCN, $C_3$-$C_{12}$ trialkylsilyl, $C_4$-$C_{12}$ trialkylsilylalkyl, $C_4$-$C_{12}$ trialkylsilylalkoxy or $G^2$; or two adjacent $R^{10}$ are taken together along with the carbon atoms to which they are bonded to form a $C_3$-$C_7$ cycloalkyl ring;

each $R^{7'}$ is independently halogen, hydroxyl, cyano, nitro, $C_1$-$C_8$ alkyl, $C_2$-$C_4$ alkoxyalkyl, $C_3$-$C_8$ alkoxyalkoxyalkyl, $C_1$-$C_4$ cyanoalkyl, $C_1$-$C_4$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, hydroxy, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, amino, $C_1$-$C_8$ alkylamino, $C_1$-$C_6$ haloalkylamino, $C_3$-$C_8$ cycloalkylamino, $C_2$-$C_8$ dialkylamino, $C_2$-$C_8$ halodialkylamino, formylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, —SF$_5$, —SCN, $C_3$-$C_{12}$ trialkylsilyl, $C_4$-$C_{12}$ trialkylsilylalkyl, $C_4$-$C_{12}$ trialkylsilylalkoxy; or two adjacent $R^{7'}$ are taken together along with the carbon atoms to which they are bonded to form a $C_3$-$C_7$ cycloalkyl ring;

each $R^8$ is independently H, cyano, $C_2$-$C_3$ alkylcarbonyl or $C_2$-$C_3$ haloalkylcarbonyl;

each $R^9$, $R^{9'}$ and $R^{11}$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{12}$ is independently H, cyano, $C_1$-$C_4$ alkyl, $C_1$-$C_4$ haloalkyl, $C_1$-$C_4$ alkoxy, $C_1$-$C_4$ haloalkoxy, —(C=O)CH$_3$ or —(C=O)CF$_3$;

each $G^1$ is independently phenyl, phenylmethyl (i.e. benzyl), pyridinylmethyl, phenylcarbonyl (i.e. benzoyl), phenoxy, phenylethynyl, phenylsulfonyl, phenylcarbonylalkyl; or a 5- or 6-membered heteroaromatic ring, each optionally substituted on ring members with up to 5 substituents independently selected from $R^{13}$;

each $G^2$ is independently phenyl, phenylmethyl (i.e. benzyl), pyridinylmethyl, phenylcarbonyl (i.e. benzoyl), phenylcarbonylalkyl, phenoxy, phenylethynyl, phenylsulfonyl; or a 5- or 6-membered heteroaromatic ring, each optionally substituted on ring members with up to 5 substituents independently selected from $R^{14}$;

each $R^{13}$ and $R^{14}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^{15}$ is independently halogen, cyano, hydroxy, $C_1$-$C_4$ alkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{16}$ is independently H, cyano, $C_1$-$C_4$ alkyl, $C_1$-$C_4$ haloalkyl, $C_1$-$C_4$ alkoxy, $C_2$-$C_4$ alkylcarbonyl, $C_2$-$C_4$ alkoxycarbonyl or $C_3$-$C_6$ cycloalkyl;

each $R^{17}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{17a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_1$-$C_6$ alkylthio, $C_1$-$C_6$ haloalkylthio, $C_3$-$C_8$ cycloalkylthio, $C_3$-$C_{10}$ trialkylsilyl or $G^1$;

each $R^{18}$ is independently H, hydroxy, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{19}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20}$ is independently H, hydroxy, amino, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy $C_3$-$C_{10}$ trialkylsilyl or $G^1$;

each $R^{23b}$ is independently H, halogen, cyano, hydroxy, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{24a}$ is independently H, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each u and v are independently 0, 1 or 2 in each instance of $S(=O)_u(=NR^8)_v$, provided that the sum of u and v is 0, 1 or 2;

provided that when
a) $J^1$ is an unsubstituted phenyl ring, A is other than —CH$_2$—, —O—, —C≡C—, —C(=O)— or —SO$_2$—; or
b) $J^1$ is an unsubstituted pyridinyl ring, A is other than —CH$_2$—;
c) $J^1$ is C$_4$-C$_{10}$ cycloalkylalkyl, A is other than alkyl; or
d) $J^1$-A- is at the para position of Q$^1$, A is other than O and $J^1$ is other than 2-furanylmethyl.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include CH$_3$OCH$_2$—, CH$_3$OCH$_2$CH$_2$—, CH$_3$CH$_2$OCH$_2$—, CH$_3$CH$_2$CH$_2$CH$_2$OCH$_2$— and CH$_3$CH$_2$OCH$_2$CH$_2$—. "Alkoxyalkoxyalkyl" denotes alkoxy substitution on the alkoxy moiety of alkoxyalkyl moiety. Examples of "alkoxyalkoxyalkyl" include CH$_3$OCH$_2$OCH$_2$—, CH$_3$CH$_2$O(CH$_3$)CHOCH$_2$— and (CH$_3$O)$_2$CHOCH$_2$—. "Alkoxyalkoxy" denotes alkoxy substitution on alkoxy. "Alkenyloxy" includes straight-chain or branched alkenyloxy moieties. Examples of "alkenyloxy" include H$_2$C=CH=CH$_2$O—, (CH$_3$)$_2$C=CH=CH$_2$O—, (CH$_3$)CH=CH=CH$_2$O—, (CH$_3$)CH=C(CH$_3$)CH$_2$O— and CH$_2$=CH=CH$_2$CH$_2$O—. "Alkynyloxy" includes straight-chain or branched alkynyloxy moieties. Examples of "alkynyloxy" include HC≡CCH$_2$O—, CH$_3$C≡CCH$_2$O— and CH$_3$C≡CCH$_2$CH$_2$O—. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include CH$_3$S(O)—, CH$_3$CH$_2$S(O)—, CH$_3$CH$_2$CH$_2$S(O)—, (CH$_3$)$_2$CHS(O)— and the different butylsulfinyl, pentylsulfinyl and hexylsulfinyl isomers. Examples of "alkylsulfonyl" include CH$_3$S(O)$_2$—, CH$_3$CH$_2$S(O)$_2$—, CH$_3$CH$_2$CH$_2$S(O)$_2$—, (CH$_3$)$_2$CHS(O)$_2$—, and the different butylsulfonyl, pentylsulfonyl and hexylsulfonyl isomers. Examples of "alkyl sulfonylamino" include CH$_3$S(O)$_2$NH—, CH$_3$CH$_2$S(O)$_2$NH—, CH$_3$CH$_2$CH$_2$S(O)$_2$NH—, (CH$_3$)$_2$CHS(O)$_2$NH—, and the different butylsulfonylamino, pentylsulfonylamino and hexylsulfonylamino isomers. Examples of "alkylsulfonyloxy" include CH$_3$S(O)$_2$O—, CH$_3$CH$_2$S(O)$_2$O—, CH$_3$CH$_2$CH$_2$S(O)$_2$O—, (CH$_3$)$_2$CHS(O)$_2$O—, and the different butylsulfonyloxy, pentylsulfonyloxy and hexylsulfonyloxy isomers. "Alkylthioalkyl" denotes alkylthio substitution on alkyl. Examples of "alkylthioalkyl" include CH$_3$SCH$_2$—, CH$_3$SCH$_2$CH$_2$—, CH$_3$CH$_2$SCH$_2$—, CH$_3$CH$_2$CH$_2$CH$_2$SCH$_2$— and CH$_3$CH$_2$SCH$_2$CH$_2$—. "Cyanoalkyl" denotes an alkyl group substituted with one cyano group. Examples of "cyanoalkyl" include NCCH$_2$—, NCCH$_2$CH$_2$— and CH$_3$CH(CN)CH$_2$—. "Cyanoalkoxy" denotes an alkoxy group substituted with one cyano group. Examples of "cyanoalkoxy" include NCCH$_2$O—, NCCH$_2$CH$_2$O— and CH$_3$CH(CN)CH$_2$O—. "Alkylsulfinylalkyl" denotes alkylsulfinyl substitution on alkyl. Examples of "alkylsulfinylalkyl" include CH$_3$S(=O)CH$_2$—, CH$_3$S(=O)CH$_2$CH$_2$—, CH$_3$CH$_2$S(=O)CH$_2$— and CH$_3$CH$_2$S(=O)CH$_2$CH$_2$—. "Alkylsulfonylalkyl" denotes alkylsulfonyl substitution on alkyl. Examples of "alkylsulfonylalkyl" include CH$_3$S(=O)$_2$CH$_2$—, CH$_3$S(=O)$_2$CH$_2$CH$_2$—, CH$_3$CH$_2$S(=O)$_2$CH$_2$— and CH$_3$CH$_2$S(=O)$_2$CH$_2$CH$_2$—. "Alkylamino", "dialkylamino", and the like, are defined analogously to the above examples. Examples of "alkylaminoalkyl" include CH$_3$NHCH$_2$—, (CH$_3$)$_2$CHNHCH$_2$— and CH$_3$NHCH(CH$_3$)—. Examples of "alkylaminocarbonyl" include CH$_3$NHC(O)—, (CH$_3$)$_2$CHNHC(O)— and CH$_3$CH$_2$NHC(O)—. Examples of "dialkylaminoalkyl" include (CH$_3$)$_2$NCH$_2$—, (CH$_3$)$_2$NC(CH$_3$)H— and (CH$_3$)(CH$_3$)NCH$_2$—. Examples of "alkylaminocarbonyl" include CH$_3$NC(O)— and CH$_3$CH$_2$NC(O)—. Examples of "dialkylaminocarbonyl" include (CH$_3$)$_2$NC(O)—. Examples of "dialkylaminosulfonyl" include (CH$_3$)$_2$NS(O)$_2$—.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkoxyalkyl" denotes cycloalkoxy substitution on an alkyl moiety. Examples of "cycloalkoxyalkyl" include cyclopropoxymethyl, cyclopentoxyethyl, and other cycloalkoxy moieties bonded to straight-chain or branched alkyl groups. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include F$_3$C—, ClCH$_2$—, CF$_3$CH$_2$— and CF$_3$CCl$_2$—. The terms "halocycloalkyl", "haloalkoxy", "haloalkylthio", "haloalkenyl", "haloalkynyl", and the like, are defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—. Examples of "haloalkylthio" include CCl$_3$S—, CF$_3$S—, CCl$_3$CH$_2$S— and ClCH$_2$CH$_2$CH$_2$S—. Examples of "haloalkylsulfinyl" include CF$_3$S(O)—, CCl$_3$S(O)—, CF$_3$CH$_2$S(O)— and CF$_3$CF$_2$S(O)—. Examples of "haloalkylsulfonyl" include CF$_3$S(O)$_2$—, CCl$_3$S(O)$_2$—, CF$_3$CH$_2$S(O)$_2$— and CF$_3$CF$_2$S(O)$_2$—. Examples of "haloalkenyl" include (Cl)$_2$C=CH—CH$_2$— and CF$_3$CH$_2$CH=CH—CH$_2$—. Examples of "haloalkynyl" include HC≡CCHCl—, CF$_3$C≡C—, CCl$_3$C≡C— and FCH$_2$C≡CCH$_2$—. Examples of "haloalkoxyalkyl" include CF$_3$OCH$_2$O—, ClCH$_2$CH$_2$OCH$_2$CH$_2$O—, Cl$_3$CCH$_2$OCH$_2$O— as well as branched alkyl derivatives.

"Alkylcarbonyl" denotes a straight-chain or branched alkyl moieties bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkylcarbonylalkoxy" include CH$_3$C(=O)CH$_2$O—, CH$_3$CH$_2$CH$_2$C(=O)CH$_2$O— and (CH$_3$)$_2$CHC(=O)CH$_2$O—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers. "Alkylcarbonyloxy" denotes an alkylcarbonyl moiety linked through an oxygen atom attached to the carbonyl. Examples of "alkylcarbonyloxy" include CH$_3$C(=O)O—, CH$_3$CH$_2$CH$_2$C(=O)O— and (CH$_3$)$_2$CHC(=O)O—.

The total number of carbon atoms in a substituent group is indicated by the "$C_i$-$C_j$" prefix where i and j are numbers from 1 to 12. For example, $C_1$-$C_4$ alkylsulfonyl designates methylsulfonyl through butylsulfonyl; $C_2$ alkoxyalkyl designates CH$_3$OCH$_2$—; $C_3$ alkoxyalkyl designates, for example, CH$_3$CH(OCH$_3$)—, CH$_3$OCH$_2$CH$_2$— or CH$_3$CH$_2$OCH$_2$—; and $C_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a compound is substituted with a substituent bearing a subscript that indicates the number of said substituents can exceed 1, said substituents (when they exceed 1) are independently selected from the group of defined substituents, e.g., ([(R$^{10}$)$_n$], n is 1, 2, 3, 4 or 5). Further, when the subscript indicates a range, e.g. (R)$_{i-j}$, then the number of substituents may be selected from the integers between i and j inclusive. When a group contains a substituent which can be hydrogen, for example (R$^1$ or R$^6$), then when this substituent is taken as hydrogen, it is recognized that this is equivalent to said group being unsubstituted. When a variable group is shown to be optionally attached to a position, for example [(R$^{10}$)$_n$] wherein n may be 0, then hydrogen may be at the position even if not recited in the variable group definition. When one or more positions on a group are said to be "not substituted" or "unsubstituted", then hydrogen atoms are attached to take up any free valency.

The expression "fully saturated" in relation to a ring of atoms means that the bonds between the atoms of the ring are all single. The expression "fully unsaturated" in relation to a ring means that the bonds between the atoms in the ring are single or double bonds according to valence bond theory and furthermore the bonds between the atoms in the ring include as many double bonds as possible without double bonds being cumulative (i.e. no C=C=C, N=C=C, etc.). The term "partially unsaturated" in relation to a ring denotes a ring comprising at least one ring member bonded to an adjacent ring member though a double bond and which conceptually potentially accommodates a number of non-cumulated double bonds through adjacent ring members (i.e. in its fully unsaturated counterpart form) greater than the number of double bonds present (i.e. in its partially unsaturated form). When a fully unsaturated ring satisfies Hückel's rule then it can also be described as aromatic.

Unless otherwise indicated, a "ring" or "ring system" as a component of Formula 1 (e.g., substituent Q$^1$) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. A "bridged bicyclic ring system" is formed by bonding a segment of one or more atoms to nonadjacent ring members of a ring. The term "ring member" refers to an atom or other moiety (e.g., C(=O), C(=S), S(O) or S(O)$_2$) forming the backbone of a ring or ring system.

The terms "carbocyclic ring" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring". The term "heteroaromatic bicyclic ring system" denotes a heterocyclic ring system in which at least one of the ring system is aromatic. Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

As noted above, $Q^1$, $J^1$ and $Q^2$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein, for example, $R^v$ is $R^7$ or $R^{7'}$ as defined in the Summary of the Invention for $Q^1$ or $J^1$ and r is an integer (from 0 to 4); or $R^v$ is $R^{10}$ as defined in the Summary of the Invention for $Q^2$, and r is an integer (from 0 to 5).

As noted above, $Q^1$, $J^1$ and $Q^2$ can be (among others) a 5- or 6-membered fully unsaturated heterocyclic ring, optionally substituted with one or more substituents selected from a group of substituents as defined in the Summary of the Invention. Examples of a 5- or 6-membered fully unsaturated heterocyclic ring optionally substituted with from one or more substituents include the rings U-2 through U-61 illustrated in Exhibit 1 wherein $R^v$ is any substituent as defined in the Summary of the Invention for $Q^1$, $J^1$ and $Q^2$, and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

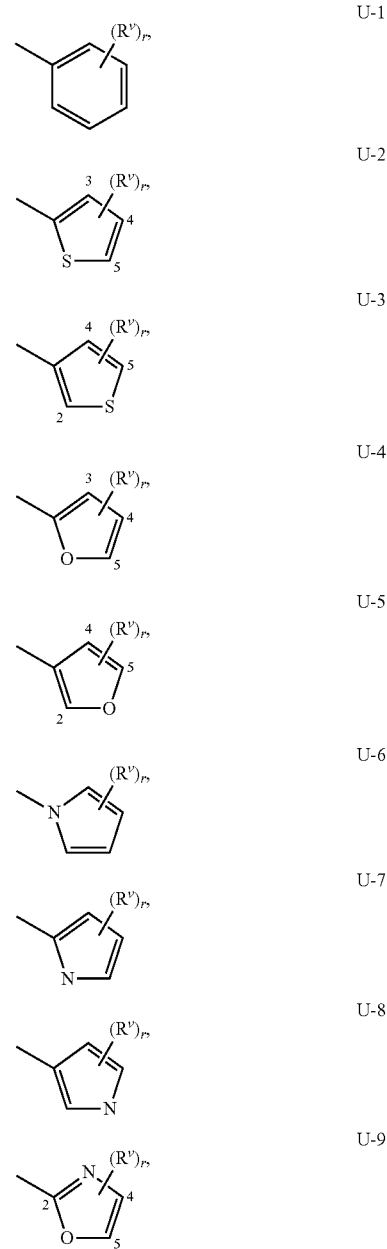

Exhibit 1

-continued
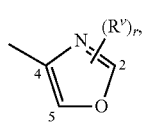 U-10
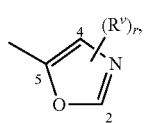 U-11
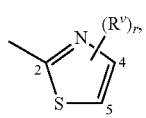 U-12
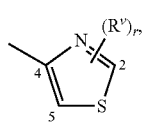 U-13
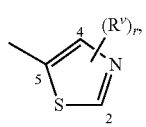 U-14
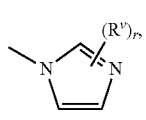 U-15
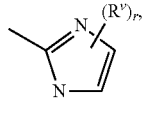 U-16
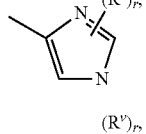 U-17
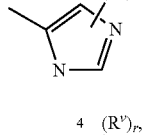 U-18
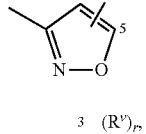 U-19
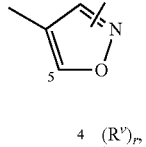 U-20
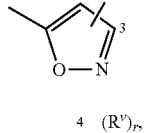 U-21
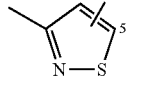 U-22
-continued
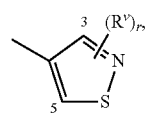 U-23
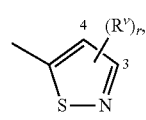 U-24
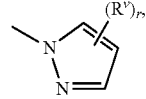 U-25
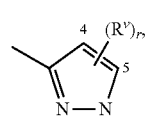 U-26
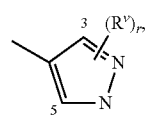 U-27
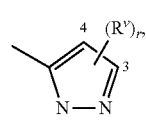 U-28
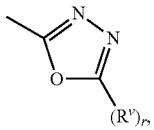 U-29
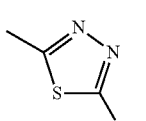 U-30
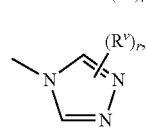 U-31
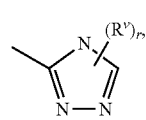 U-32
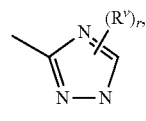 U-33
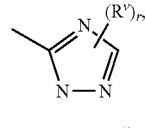 U-34
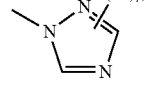 U-35

-continued
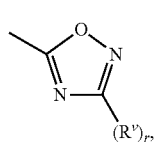 U-36
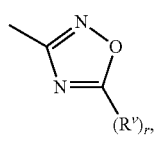 U-37
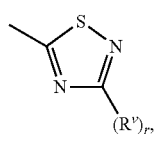 U-38
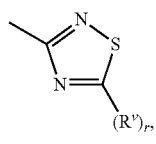 U-39
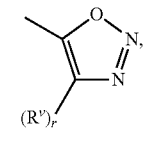 U-40
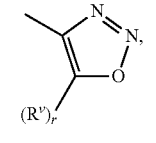 U-41
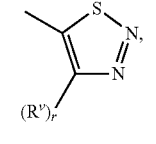 U-42
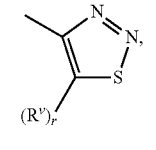 U-43
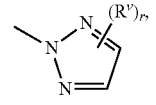 U-44
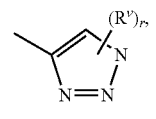 U-45
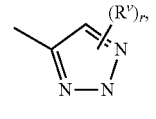 U-46
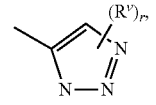 U-47
-continued
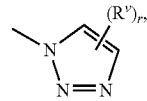 U-48
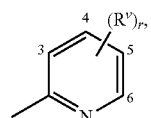 U-49
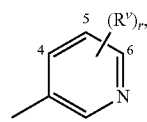 U-50
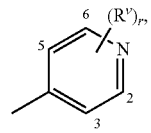 U-51
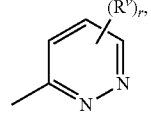 U-52
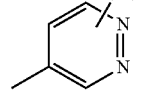 U-53
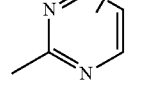 U-54
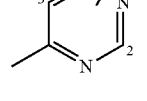 U-55
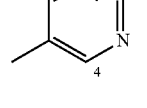 U-56
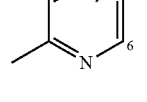 U-57
U-58

-continued

U-59
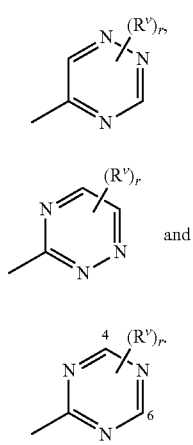
U-60 and

U-61

As noted above, $Q^1$, $J^1$ and $Q^2$ can be (among others) an 8- to 10-membered heteroaromatic bicyclic ring system optionally substituted with one or more substituents selected from a group of substituents as defined in the Summary of the Invention (i.e. $R^7$, $R^{7'}$ and $R^{10}$). Examples of 8- to 10-membered heteroaromatic bicyclic ring system optionally substituted with from one or more substituents include the rings U-62 through U-100 illustrated in Exhibit 2 wherein $R^v$ is any substituent as defined in the Summary of the Invention for $Q^1$, $J^1$ or $Q^2$, and r is typically an integer from 0 to 4 or 5.

Exhibit 2

U-62
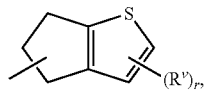

U-63
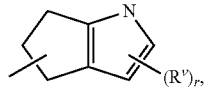

U-64
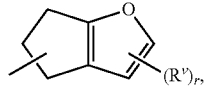

U-65
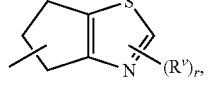

U-66
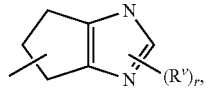

U-67
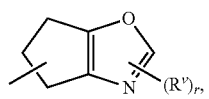

U-68
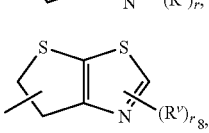

-continued

U-69
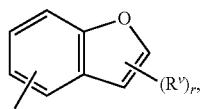

U-70
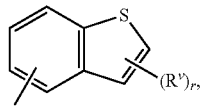

U-71
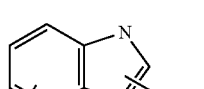

U-72
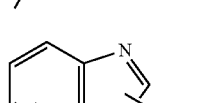

U-73
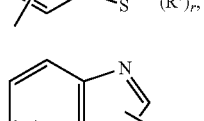

U-74
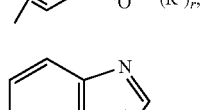

U-75
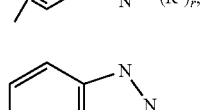

U-76
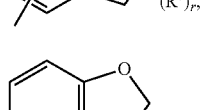

U-77
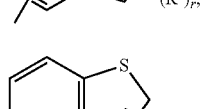

U-78
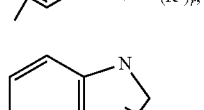

U-79
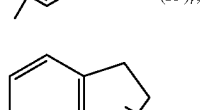

U-80
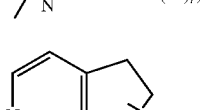

U-81
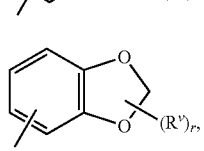

Some examples of a 4- to 6-membered saturated heterocyclic ring optionally substituted with one or more substituents include but not limited to the rings U-101 through U-104 illustrated in Exhibit 3 wherein $R^v$ is any substituent as defined in the Summary of the Invention for $Q^1$ or $Q^2$, and r is typically an integer from 0 to 4 or 5.

Although $R^v$ groups are shown in the structures U-1 through U-104, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Preferably for greatest herbicidal activity, the U group is attached to the remainder of Formula 1 through an available carbon or nitrogen on a fully unsaturated ring of the U group. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. Particularly when $R^4$ and $R^5$ are each H, the $C(O)N(Q^2)(R^6)$ and $Q^1$ substituents are typically mostly in the thermodynamically preferred trans configuration on the pyrrolidinone ring.

For example the $C(O)N(Q^2)(R^6)$ moiety (bonded to the carbon at the 3-position of the pyrrolidinone ring wherein $Y^1$ and $Y^2$ are both oxygen and $J^2$ is —$CR^2R^3$ and both $R^2$ and $R^3$ are H) and $Q^1$ (bonded to the carbon at the 4-position of the pyrrolidinone ring) are generally found in the trans configuration. These two carbon atoms (i.e. at the 3- and 4-positions each posses the central ring of Formula 1) both possess a chiral center. The two most prevelant pairs of enantiomers are depicted as Formula 1' and Formula 1" where the chiral centers are identified (i.e. as 3R,4S or as 3S,4R). The skilled artisan will understand that in some Embodiments of the invention, the R or S designation is determined relative to other substituents around the same carbon and therefore a compound of the invention could also be given the 3S,4S designation. For a comprehensive discussion of all aspects of stereoisomerism, see Ernest L. Eliel and Samuel H. Wilen, *Stereochemistry of Organic Compounds*, John Wiley & Sons, 1994.

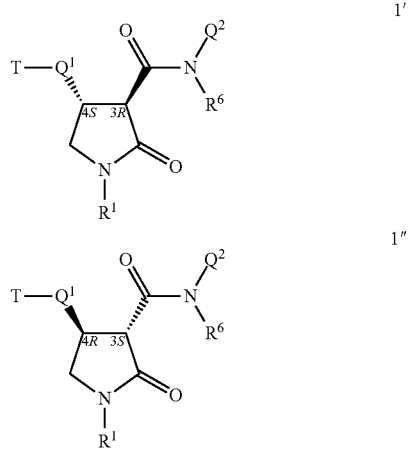

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention comprises racemic mixtures, for example, equal amounts of the enantiomers of Formulae 1' and 1". In addition, this invention includes compounds that are enriched compared to the racemic mixture in an enantiomer of Formula 1. Also included are the essentially pure enantiomers of compounds of Formula 1, for example, Formula 1' and Formula 1".

When enantiomerically enriched (i.e. enantio-enriched), one enantiomer is present in greater amounts than the other, and the extent of enrichment can be defined by an expression of enantiomeric excess ("ee"), which is defined as $(2x-1) \cdot 100\%$, where x is the mole fraction of the dominant enantiomer in the mixture (e.g., an ee of 20% corresponds to a 60:40 ratio of enantiomers). The compounds of the invention can be prepared entantiomerically enriched (i.e. enantio-enriched) by utilizing a corresponding enantiomerically enriched intermediate during the course of synthesis. In these instances the enantiomeric excess is not measured in the final product but is presumed to be "enantiomerically enriched" based on equivalent known chemical transformations in the literature.

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^2$ and $R^3$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond (e.g., $C(O)N(Q^2)(R^6)$) in Formula 1. This invention comprises mixtures of conformational isomers. In addition, this invention includes compounds that are enriched in one conformer relative to others.

Compounds of Formula 1 typically exist in more than one form, and Formula 1 thus include all crystalline and noncrystalline forms of the compounds they represent. Noncrystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1

A compound of Formula 1 wherein when $Q^1$ is a 5- to 6-membered heteroaromatic ring or an 8- to 10-membered heteroaromatic bicyclic ring system, each ring or ring system optionally substituted with up to 4 substituents independently selected from $R^7$ on carbon atom ring members and selected from $R^9$ on nitrogen atom ring members.

Embodiment 2

A compound of Embodiment 1 wherein $Q^1$ is unsubstituted with $R^7$ or $R^9$.

Embodiment 3

A compound of Formula 1 wherein $Q^1$ is a phenyl ring or a naphthalenyl ring system, each ring or ring system optionally substituted with 1 to 4 substituents independently selected from $R^7$.

Embodiment 4

A compound of Embodiment 3 wherein $Q^1$ is a phenyl ring optionally substituted with 1 to 2 substituents independently selected from $R^7$.

Embodiment 5

A compound of Embodiment 4 wherein $Q^1$ is a phenyl ring substituted with 1 substituent selected from $R^7$.

Embodiment 6

A compound of Embodiment 4 wherein $Q^1$ is a phenyl ring unsubstituted with $R^7$.

Embodiment 7

A compound of Formula 1 or any one of Embodiment 1 through Embodiment 6 wherein when $Q^2$ is a 5- to 6-membered heteroaromatic ring or an 8- to 10-membered heteroaromatic bicyclic ring system, each ring or

Embodiment 8

A compound of Formula 1 or any one of Embodiment 1 through Embodiment 6 wherein $Q^2$ is a phenyl ring optionally substituted with 1 to 5 substituents independently selected from $R^{10}$.

Embodiment 9

A compound of Embodiment 8 wherein $Q^2$ is a phenyl ring optionally substituted with 1 to 3 substituents independently selected from $R^{10}$.

Embodiment 10

A compound of Embodiment 9 wherein $Q^2$ is a phenyl ring optionally substituted with 1 to 2 substituents independently selected from $R^{10}$.

Embodiment 11

A compound of Formula 1 or any one of Embodiment 1 through Embodiment 10 wherein $Q^2$ is a phenyl ring having at least one substituent selected from $R^{10}$ at an ortho position (and optionally other substituents).

Embodiment 12

A compound of Formula 1 or any one of Embodiment 1 through Embodiment 9 wherein when $Q^2$ is a phenyl ring substituted with at least two substituents selected from $R^{10}$, then at least one substituent is at an ortho position and at least one substituent is at a para position of the phenyl ring.

Embodiment 13

A compound of Formula 1 or any one of Embodiment 1 through Embodiment 9 wherein $Q^2$ is a phenyl ring substituted with three substituents selected from $R^{10}$ and the three substituents are at an ortho, meta and para positions of the phenyl ring.

Embodiment 14

A compound of Formula 1 or any one of Embodiment 1 through Embodiment 13 wherein T is $J^1$-A-.

Embodiment 15

A compound of Embodiment 14 wherein A is a saturated, partially unsaturated or fully unsaturated chain containing 1- to 3-atoms selected from up to 3 carbon, up to 1 O, up to 1 S and up to 2 N atoms, the chain optionally substituted with up to 2 substituents independently selected from $R^{15}$ on carbon atoms and $R^{16}$ on nitrogen atoms.

Embodiment 16

A compound of Embodiment 15 wherein A is —$CH_2$—, —$CH_2O$—, —$CH_2NH$—, —CH=CH—, —C≡C—, —NH—, —O—, —S—, —SO— or —$SO_2$—.

Embodiment 17

A compound of Embodiment 16 wherein A is —$CH_2$—, —$CH_2O$—, —$CH_2NH$—, —CH=CH—, —C≡C—, —NH— or —O—.

Embodiment 18

A compound of Embodiment 17 wherein A is —$CH_2O$— or —O—.

Embodiment 19

A compound of Formula 1 or any one of Embodiment 1 through Embodiment 18 wherein $J^1$ is a phenyl ring or a naphthalenyl ring system, each ring or ring system optionally substituted with up to 5 substituents independently selected from $R^{7'}$; or a 4- to 6-membered heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{7'}$ on carbon atom ring members and selected from $R^9$ on nitrogen atom ring members; or $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_3$-$C_8$ haloalkoxyalkoxy, $C_1$-$C_8$ haloalkyl, $C_3$-$C_8$ halocycloalkyl, $C_2$-$C_8$ alkylcarbonyloxy or $C_2$-$C_8$ haloalkylcarbonyloxy.

Embodiment 20

A compound of Embodiment 19 wherein $J^1$ is a phenyl ring or a naphthalenyl ring system, each ring or ring system optionally substituted with up to 4 substituents independently selected from $R^{7'}$.

Embodiment 21

A compound of Embodiment 20 wherein $J^1$ is a phenyl ring optionally substituted with up to 3 substituents independently selected from $R^{7'}$.

Embodiment 22

A compound of Embodiment 21 wherein $J^1$ is a phenyl ring optionally substituted with 1 substituents independently selected from $R^{7'}$.

Embodiment 23

A compound of Embodiment 22 wherein $J^1$ is a phenyl ring unsubstituted with $R^{7'}$.

Embodiment 24

A compound of Embodiment 19 wherein $J^1$ is a 4- to 6-membered heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u$ (=NR$^8$)$_v$, each ring or ring system optionally substituted with up to 5 substituents independently selected from $R^{7'}$ on carbon atom ring members and selected from $R^{9'}$ on nitrogen atom ring members.

Embodiment 25

A compound of Embodiment 24 wherein $J^1$ is a 4- to 6-membered heterocyclic ring containing ring members selected from carbon atoms and 1 to 3 heteroatoms independently selected from up to 2 O, up to 2 S and up to 3 N atoms, wherein up to 2 carbon ring members are independently selected from C(=O) and C(=S), and the sulfur atom ring members are independently selected from $S(=O)_u(=NR^8)_v$, each ring or ring system optionally substituted with up to 3 substituents independently selected from $R^{7'}$ on carbon atom ring members and selected from $R^{9'}$ on nitrogen atom ring members.

Embodiment 26

A compound of Embodiment 25 wherein $J^1$ is a 5- to 6-membered heteroaromatic ring optionally substituted with 1 substituent selected from $R^{7'}$ on carbon atom ring members.

Embodiment 27

A compound of Embodiment 26 wherein $J^1$ is an unsubstituted pyridine ring.

Embodiment 28

A compound of Embodiment 19 wherein $J^1$ is $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_3$-$C_8$ haloalkoxyalkoxy, $C_2$-$C_8$ haloalkoxyhaloalkyl, $C_1$-$C_8$ haloalkyl, $C_3$-$C_8$ halocycloalkyl, $C_2$-$C_8$ alkylcarbonyloxy or $C_2$-$C_8$ haloalkylcarbonyloxy.

Embodiment 29

A compound of Formula 1 or any one of Embodiment 1 through Embodiment 13 wherein T is $R^{17}ON=CR^{17a}$—, $(R^{18})_2C=NO$—, $(R^{19})_2NN=CR^{17a}$—, $(R^{18})_2C=NNR^{20a}$—, $R^{20}N=CR^{17a}$—, $(R^{18})_2C=N$—, $R^{23}ON=CR^{17a}C(R^{23b})_2$— or $(R^{18})_2C=NOC(R^{24a})_2$—, wherein the free bond projecting to the right indicates the connecting point to $Q^1$.

Embodiment 30

A compound of Embodiment 29 wherein each $R^{17}$ is independently H, $C_1$-$C_6$ alkyl, $C_3$-$C_8$ cycloalkyl, $C_4$-$C_8$ cycloalkylalkyl, or $C_1$-$C_6$ haloalkyl.

Embodiment 31

A compound of Embodiment 29 wherein each $R^{17a}$ is independently H, $C_1$-$C_6$ alkyl, $C_3$-$C_8$ cycloalkyl, $C_4$-$C_8$ cycloalkylalkyl, or $C_1$-$C_6$ haloalkyl.

Embodiment 32

A compound of Embodiment 29 wherein each $R^{18}$ is independently H, hydroxy, $C_1$-$C_6$ alkyl, $C_3$-$C_8$ cycloalkyl, $C_4$-$C_8$ cycloalkylalkyl or $C_1$-$C_6$ haloalkyl.

Embodiment 33

A compound of Embodiment 29 wherein each $R^{19}$ is independently H, $C_1$-$C_6$ alkyl, $C_3$-$C_8$ cycloalkyl, $C_4$-$C_8$ cycloalkylalkyl or $C_1$-$C_6$ haloalkyl.

Embodiment 34

A compound of Embodiment 29 wherein each $R^{20}$ is independently H, hydroxy, amino, $C_1$-$C_6$ alkyl, $C_3$-$C_8$ cycloalkyl, $C_4$-$C_8$ cycloalkylalkyl or $C_1$-$C_6$ haloalkyl.

Embodiment 35

A compound of Embodiment 29 wherein each $R^{20a}$ is independently H, $C_1$-$C_6$ alkyl, $C_3$-$C_8$ cycloalkyl, $C_4$-$C_8$ cycloalkylalkyl or $C_1$-$C_6$ haloalkyl.

Embodiment 36

A compound of Embodiment 29 wherein each $R^{23b}$ is independently H, halogen, cyano, hydroxy, $C_1$-$C_4$ alkyl, $C_3$-$C_8$ cycloalkyl, $C_4$-$C_8$ cycloalkylalkyl or $C_1$-$C_4$ haloalkyl.

Embodiment 37

A compound of Embodiment 29 wherein each $R^{24a}$ is independently H, $C_1$-$C_4$ alkyl, $C_3$-$C_8$ cycloalkyl, $C_4$-$C_8$ cycloalkylalkyl or $C_1$-$C_4$ haloalkyl.

Embodiment 38

A compound of Formula 1 or any one of Embodiment 1 through Embodiment 37 wherein $J^2$ is —$CR^2R^3$—.

Embodiment 39

A compound of Formula 1 or any one of Embodiment 1 through Embodiment 37 wherein $J^2$ is —$CR^2R^3$—$CR^{2a}R^{3a}$—.

Embodiment 40

A compound of Formula 1 or any one of Embodiment 1 through Embodiment 39 wherein $R^1$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl or $C_4$-$C_8$ cycloalkylalkyl.

Embodiment 41

A compound of Embodiment 40 wherein $R^1$ is H, $C_1$-$C_6$ alkyl or $C_1$-$C_6$ haloalkyl.

Embodiment 42

A compound of Embodiment 41 wherein $R^1$ is H, Me, Et or $CHF_2$.

Embodiment 43

A compound of Embodiment 42 wherein $R^1$ is H, Me or Et.

Embodiment 44

A compound of Embodiment 43 wherein $R^1$ is H.

Embodiment 45

A compound of Embodiment 43 wherein $R^1$ is Me.

Embodiment 46

A compound of Formula 1 or any one of Embodiment 1 through Embodiment 45 wherein $R^2$ is H or $CH_3$.

Embodiment 47

A compound of Embodiment 46 wherein $R^2$ is H.

Embodiment 48

A compound of Formula 1 or any one of Embodiment 1 through Embodiment 47 wherein $R^3$ is H or $CH_3$.

Embodiment 49

A compound of Embodiment 48 wherein $R^3$ is H.

Embodiment 50

A compound of Formula 1 or any one of Embodiment 1 through Embodiment 49 wherein $R^{2a}$ is H or $CH_3$.

Embodiment 51

A compound of Embodiment 50 wherein $R^{2a}$ is H.

Embodiment 52

A compound of Formula 1 or any one of Embodiment 1 through Embodiment 51 wherein $R^{3a}$ is H or $CH_3$.

Embodiment 53

A compound of Embodiment 52 wherein $R^{3a}$ is H.

Embodiment 54

A compound of Formula 1 or any one of Embodiment 1 through Embodiment 53 wherein $R^4$ is H or $CH_3$.

Embodiment 55

A compound of Embodiment 54 wherein $R^4$ is H.

Embodiment 56

A compound of Formula 1 or any one of Embodiment 1 through Embodiment 55 wherein $R^5$ is H or $CH_3$.

Embodiment 57

A compound of Embodiment 56 wherein $R^5$ is H.

Embodiment 58

A compound of Formula 1 or any one of Embodiment 1 through Embodiment 57 wherein $R^6$ is H or $CH_3$.

Embodiment 59

A compound of Embodiment 58 wherein $R^6$ is H.

Embodiment 60

A compound of Formula 1 or any one of Embodiment 1 through Embodiment 59 wherein each $R^7$ is independently halogen, cyano, nitro, $C_1$-$C_4$ alkyl, $C_1$-$C_4$ cyanoalkyl, $C_1$-$C_4$ cyanoalkoxy, $C_1$-$C_4$ haloalkyl, $C_2$-$C_4$ alkenyl, $C_2$-$C_4$ haloalkenyl $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, cyclopropylmethyl, methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, formyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_4$ trialkylsilyl, trimethylsilylmethyl or trimethylsilylmethoxy.

Embodiment 61

A compound of Embodiment 60 wherein each $R^7$ is independently halogen, cyano, $C_1$-$C_2$ alkyl, $C_1$-$C_3$ haloalkyl or $C_1$-$C_3$ alkylsulfonyl.

Embodiment 62

A compound of Embodiment 61 wherein each $R^7$ is independently halogen or $C_1$-$C_2$ haloalkyl.

Embodiment 63

A compound of Embodiment 62 wherein each $R^7$ is independently halogen or $CF_3$.

Embodiment 64

A compound of Embodiment 63 wherein each $R^7$ is independently F or $CF_3$.

Embodiment 65

A compound of Formula 1 or any one of Embodiment 1 through Embodiment 64 wherein each $R^{10}$ is indepen-

Embodiment 66

A compound of Embodiment 65 wherein each $R^{10}$ is independently halogen or $C_1$-$C_2$ haloalkyl.

Embodiment 67

A compound of Embodiment 66 wherein each $R^{10}$ is independently halogen or $CF_3$.

Embodiment 68

A compound of Embodiment 67 wherein each $R^{10}$ is independently F or $CF_3$.

Embodiment 69

A compound of Embodiment 68 wherein each $R^{10}$ is independently F.

Embodiment 70

A compound of Formula 1 or any one of Embodiment 1 through Embodiment 69 wherein each $R^{7'}$ is independently halogen, cyano, nitro, $C_1$-$C_8$ alkyl or $C_1$-$C_8$ haloalkyl.

Embodiment 71

A compound of Embodiment 70 wherein each $R^{7'}$ is independently halogen.

Embodiment 72

A compound of Formula 1 or any one of Embodiment 1 through Embodiment 71 wherein $Y^1$ is O.

Embodiment 73

A compound of Formula 1 or any one of Embodiment 1 through Embodiment 72 wherein $Y^2$ is O.

Embodiment 74

A compound of Formula 1 or any one of Embodiment 1 through Embodiment 73 wherein $Y^1$ and $Y^2$ are both O.

Embodiment 75

A compound of Formula 1 or any one of Embodiment 1 through Embodiment 74 wherein each $R^9$, $R^{9'}$ and $R^{11}$ is independently $C_1$-$C_3$ alkyl or $C_3$-$C_6$ cycloalkyl.

Embodiment 76

A compound of Formula 1 wherein T is attached at the 2- or 3-position of $Q^1$.

Embodiment 77

A compound of Formula 1 wherein T is attached at the 3-position of $Q^1$.

Embodiment 78

A compound of Formula 1 wherein T is $R^{17}ON=CR^{17a}$—, $(R^{18})_2C=NO$— or $(R^{19})_2NN=CR^{17a}$—, wherein the free bond projecting to the right indicates the connecting point to $Q^1$.

Embodiment 79

A compound of Embodiment 77 wherein T is $R^{17}ON=CR^{17a}$— or $(R^{19})_2NN=CR^{17a}$—, wherein the free bond projecting to the right indicates the connecting point to $Q^1$.

Embodiment 80

A compound of Formula 1 wherein $J^1$ is a phenyl ring or a naphthalenyl ring system, each ring or ring system optionally substituted with up to 5 substituents independently selected from $R^{7'}$; or a 4- to 6-membered heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{7'}$ on carbon atom ring members and selected from $R^{9'}$ on nitrogen atom ring members.

Embodiment 81

A compound of Formula 1 wherein $J^1$ is $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_3$-$C_8$ haloalkoxyalkoxy, $C_2$-$C_8$ haloalkoxyhaloalkyl, $C_1$-$C_8$ haloalkyl, $C_3$-$C_8$ halocycloalkyl, $C_2$-$C_8$ alkylcarbonyloxy or $C_2$-$C_8$ haloalkylcarbonyloxy.

Embodiment 82

A compound of Embodiment 80 wherein $J^1$ is $C_4$-$C_{10}$ cycloalkylalkoxy, $C_2$-$C_8$ alkenyloxy, $C_2$-$C_8$ haloalkenyloxy, $C_2$-$C_8$ alkoxyalkoxy, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ haloalkoxyalkoxy, $C_2$-$C_8$ alkylcarbonyloxy or $C_2$-$C_8$ haloalkylcarbonyloxy.

Embodiment 83

A compound of Embodiment 81 wherein $J^1$ is $C_4$-$C_{10}$ cycloalkylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_1$-$C_8$ haloalkyl or $C_3$-$C_8$ halocycloalkyl.

Embodiment 84

A compound of Embodiment 83 wherein $J^1$ is $C_2$-$C_8$ alkylthioalkyl, $C_2$-$C_8$ alkylsulfinylalkyl, $C_2$-$C_8$ alkylsulfonylalkyl, $C_2$-$C_8$ alkoxyalkyl or $C_2$-$C_8$ haloalkoxyalkyl.

Embodiment 85

A compound of Formula 1 or Embodiment 15 wherein A is a saturated, partially unsaturated or fully unsaturated chain containing 2- to 3-atoms selected from up to 3 carbon, up to 1 O, up to 1 S and up to 1 N atom, the chain optionally substituted with up to 2 substituents independently selected from $R^{15}$ on carbon atoms and $R^{16}$ on nitrogen atoms.

Embodiment 86

A compound of Embodiment 85 wherein A is a saturated, partially unsaturated or fully unsaturated chain containing 2- to 3-atoms selected from up to 3 carbon, up to 1 O, and up to 1 N atom, the chain optionally substituted with up to 2 substituents independently selected from $R^{15}$ on carbon atoms and $R^{16}$ on nitrogen atoms.

Embodiment 87

A compound of Embodiment 86 wherein A is a chain containing 2- to 3-atoms selected from up to 2 carbon, up to 1 O, and up to 1 N atom, the chain optionally substituted with up to 2 substituents independently selected from $R^{15}$ on carbon atoms and $R^{16}$ on nitrogen atoms.

Embodiment 88

A compound of Formula 1 wherein A is —$CH_2$—, —$CH_2O$—, —$OCH_2$—, —$CH_2NH$—, —$CH_2CH_2$—, —CH=CH—, —C≡C—, —NH—, —O—, —S—, —SO— or —$SO_2$—.

Embodiment 89

A compound of Formula 1 wherein A is —$CH_2$—, —$CH_2O$—, —$OCH_2$— or —O—.SO— or —$SO_2$—.

Embodiment 90

A compound of Formula 1 wherein A is —$CH_2O$—, —$OCH_2$—, —$CH_2CH_2$—, —CH=CH— or —C≡C—.

Embodiment 91

A compound of Formula 1 or any one of Embodiments 16 through 19 or 88 through 90 wherein the free bond projecting to the right indicates the connecting point of A to $Q^1$ and the free bond projecting to the left indicates the connecting point of A to $J^1$.

Embodiment 92

A compound of Formula 1 wherein when $J^2$ is —$CR^2R^3$— and $J^1$ is a phenyl ring optionally substituted with uot to 5 substituents independently selected from $R^{7'}$, then $R^{7'}$ is other than halogen, hydroxyl, cyano, nitro, $C_1$-$C_6$ alkyl, $C_1$-$C_6$ haloalkyl, $C_2$-$C_6$ alkenyl, $C_2$-$C_6$ alkynyl, CHO, $C_2$-$C_8$ alkylcarbonyl, $C_2$-$C_8$ haloalkylcarbonyl, —C(=O)OH, $C_2$-$C_8$ alkoxycarbonyl, $C_4$-$C_{10}$ cycloalkoxycarbonyl, $C_5$-$C_{12}$ cycloalkylalkoxycarbonyl, —C(=O)$NH_2$, $C_2$-$C_8$ alkylaminocarbonyl, $C_3$-$C_{10}$ dialkylaminocarbonyl, hydroxy, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylamino, $C_2$-$C_8$ dialkylamino, $C_2$-$C_8$ alkylcarbonylamino, $C_1$-$C_6$ alkylsulfonylamino or $C_3$-$C_{10}$ trialkylsilyl.

Embodiment 93

A compound of Formula 1 wherein when $J^2$ is —$CR^2R^3$—$CR^{2a}R^{3a}$— and $J^1$ is a pyridyl ring (i.e. a 6-membered heterocyclic ring optionally substituted with up to 5 substituents independently selected from $R^{7'}$ on carbon atom ring members) then $R^{7'}$ is other than halogen, hydroxyl, cyano, nitro, $C_1$-$C_6$ alkyl, $C_1$-$C_6$ haloalkyl, $C_2$-$C_6$ alkenyl, $C_2$-$C_6$ alkynyl, CHO, $C_2$-$C_8$ alkylcarbonyl, $C_2$-$C_8$ haloalkylcarbonyl, —C(=O)OH, $C_2$-$C_8$ alkoxycarbonyl, $C_4$-$C_{10}$ cycloalkoxycarbonyl, $C_5$-$C_{12}$ cycloalkylalkoxycarbonyl, —C(=O)$NH_2$, $C_2$-$C_8$ alkylaminocarbonyl, $C_3$-$C_{10}$ dialkylaminocarbonyl, hydroxy, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylamino, $C_2$-$C_8$ dialkylamino, $C_2$-$C_8$ alkylcarbonylamino, $C_1$-$C_6$ alkylsulfonylamino or $C_3$-$C_{10}$ trialkylsilyl.

Embodiment 94

A compound of Formula 1 wherein $Q^1$ is a 5- to 6-membered heteroaromatic ring or an 8- to 10-membered heteroaromatic bicyclic ring system, each ring or ring system optionally substituted with up to 4 substituents independently selected from $R^7$ on carbon atom ring members and selected from $R^9$ on nitrogen atom ring members.

Embodiment 95

A compound Formula 1 wherein $Q^1$ is a phenyl ring optionally substituted with 1 to 4 substituents independently selected from $R^7$; or a 5- to 6-membered heteroaromatic ring containing ring members selected from carbon atoms and 1 to 4 heteroatoms independently selected from up to 2 O, up to 2 S and up to 4 N atoms, optionally substituted with up to 4 substituents independently selected from $R^7$ on carbon atom ring members and selected from $R^9$ on nitrogen atom ring members.

Embodiment 96

A compound of Formula 1 or Embodiment 95 wherein $Q^1$ is a phenyl ring optionally substituted with up to 4 substituents independently selected from $R^7$.

Embodiment 97

A compound of Formula 1 wherein $Q^2$ is a phenyl ring optionally substituted with up to 5 substituents independently selected from $R^{10}$; or a 5- to 6-membered heteroaromatic ring containing ring members selected from carbon atoms and 1 to 4 heteroatoms independently selected from up to 2 O, up to 2 S and up to 4 N atoms, optionally substituted with up to 5 substituents independently selected from $R^{10}$ on carbon atom ring members and selected from $R^{11}$ on nitrogen atom ring members.

Embodiment 98

A compound of Formula 1 or Embodiment 97 wherein $Q^2$ is a phenyl ring optionally substituted with up to 4 substituents independently selected from $R^{10}$.

Embodiment 99

A compound of Formula 1 wherein $J^1$ is a phenyl ring optionally substituted with up to 5 substituents independently selected from $R^{7'}$; or a 4- to 6-membered heterocyclic ring containing ring members selected from carbon atoms and 1 to 4 heteroatoms independently selected from up to 2 O, up to 2 S and up to 4 N atoms, optionally substituted with up to 5 substituents independently selected from $R^{7'}$ on carbon atom ring members and selected from $R^{9'}$ on nitrogen atom ring members.

Embodiment 100

A compound of Formula 1 or Embodiment 99 wherein $J^1$ is a phenyl ring optionally substituted with up to 4 substituents independently selected from $R^{7'}$; or a 6-membered heterocyclic ring containing ring members selected from carbon atoms and 1 to 3 heteroatoms independently selected from up to 3 N atoms, optionally substituted with up to 4 substituents independently selected from $R^{7'}$ on carbon atom ring members and selected from $R^{9'}$ on nitrogen atom ring members.

Embodiment 101

A compound of Formula 1 wherein $R^7$ is independently halogen, $CH_3$, $CH_2CH_3$ or $CF_3$.

Embodiment 102

A compound of Formula 1 wherein $R^{10}$ is independently halogen, $CH_3$, $CH_2CH_3$ or $CF_3$.

Embodiment 103

A compound of Formula 1 wherein each $R^{10}$ is independently cyano or $CH_3$.

Embodiment 104

A compound of Formula 1 wherein each $R^{16}$ is H.

Embodiment 105

A compound of Formula 1 wherein each $R^{16}$ is other than H.

Embodiments of this invention, including Embodiments 1-105 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-105 above as well as any other embodiments described herein, and any combination thereof, pertain to the compositions and methods of the present invention.

Combinations of Embodiments 1-105 are illustrated by:

Embodiment A

A compound of Formula 1 wherein
$Q^1$ is a phenyl ring substituted with up to 2 substituents selected from $R^7$;
$Q^2$ is a phenyl ring substituted with 1 to 3 substituents independently selected from $R^{10}$; and
A is —$CH_2$—, —$CH_2O$—, —$CH_2NH$—, —CH=CH—, —C≡C—, —NH—, —O—, —S—, —SO— or —$SO_2$—.

Embodiment B

A compound of Embodiment A wherein
$J^1$ is a phenyl ring optionally substituted with 1 substituents independently selected from $R^{7'}$;
$J^2$ is —$CR^2R^3$—;
$Y^1$ and $Y^2$ are both O;
$R^1$ is H, Me or Et;
$R^4$ is H;
$R^5$ is H;
$R^6$ is H;
each $R^7$ is independently halogen or $CF_3$;
each $R^{7'}$ is independently halogen, cyano, nitro, $C_1$-$C_8$ alkyl or $C_1$-$C_8$ haloalkyl; and
each $R^{10}$ is independently halogen or $CF_3$.

Embodiment C

A compound of Embodiment A wherein
$J^1$ is a 5- to 6-membered heteroaromatic ring optionally substituted with 1 substituent selected from $R^{7'}$ on carbon atom ring member;
$J^2$ is —$CR^2R^3$—;
$Y^1$ and $Y^2$ are both O;
$R^1$ is H, Me or Et;
$R^4$ is H;
$R^5$ is H;
$R^6$ is H;
each $R^7$ is independently halogen or $CF_3$;
each $R^{7'}$ is independently halogen, cyano, nitro, $C_1$-$C_8$ alkyl or $C_1$-$C_8$ haloalkyl; and
each $R^{10}$ is independently halogen or $CF_3$.

Embodiment D

A compound of Embodiment B wherein
$Q^1$ is a phenyl ring unsubstituted with $R^7$;
$Q^2$ is a phenyl ring substituted with at least two substituents selected from $R^{10}$, at least one substituent is at an ortho position and at least one substituent is at a para position of the phenyl ring;
A is —$CH_2$—, —$CH_2O$—, —$CH_2NH$—, —CH=CH—, —C≡C—, —NH— or O;
$J^1$ is a phenyl ring unsubstituted with $R^{7'}$;
$R^2$ is H; and
$R^3$ is H.

Embodiment E

A compound of Embodiment D wherein
A is —$CH_2O$— or —O—.

Embodiment F

A compound of Embodiment C wherein
$Q^1$ is a phenyl ring unsubstituted with $R^7$;
$Q^2$ is a phenyl ring substituted with at least two substituents selected from $R^{10}$, at least one substituent is at an ortho position and at least one substituent is at a para position of the phenyl ring;
A is $CH_2$, $-CH_2O-$, $-CH_2NH-$, $-CH=CH-$, $-C\equiv C-$, $-NH-$ or O;
$J^1$ is a 5- to 6-membered heteroaromatic ring optionally substituted with up to 1 substituent selected from $R^{7'}$ on carbon atom ring member;
$R^2$ is H; and
$R^3$ is H.

Embodiment G

A compound of Embodiment F wherein
$J^1$ is an unsubstituted pyridine ring;
$Q^2$ is a phenyl ring substituted with three substituents selected from $R^{10}$ and the three substituents are at ortho, meta and para positions (of the phenyl ring); and
A is $-CH_2O-$ or $-O-$.

Embodiment H

A compound of Formula 1 wherein
$Q^1$ is a phenyl ring optionally substituted with 1 to 4 substituents independently selected from $R^7$; or a 5- to 6-membered heteroaromatic ring containing ring members selected from carbon atoms and 1 to 4 heteroatoms independently selected from up to 2 O, up to 2 S and up to 4 N atoms, optionally substituted with up to 4 substituents independently selected from $R^7$ on carbon atom ring members and selected from $R^9$ on nitrogen atom ring members;
$Q^2$ is a phenyl ring optionally substituted with up to 5 substituents independently selected from $R^{10}$; or a 5- to 6-membered heteroaromatic ring containing ring members selected from carbon atoms and 1 to 4 heteroatoms independently selected from up to 2 O, up to 2 S and up to 4 N atoms, optionally substituted with up to 5 substituents independently selected from $R^{10}$ on carbon atom ring members and selected from $R^{11}$ on nitrogen atom ring members;
$J^1$ is a phenyl ring optionally substituted with up to 5 substituents independently selected from $R^{7'}$; or a 4- to 6-membered heterocyclic ring containing ring members selected from carbon atoms and 1 to 4 heteroatoms independently selected from up to 2 O, up to 2 S and up to 4 N atoms, optionally substituted with up to 5 substituents independently selected from $R^{7'}$ on carbon atom ring members and selected from $R^{9'}$ on nitrogen atom ring members;
$R^1$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl or $C_4$-$C_8$ cycloalkylalkyl; and
A is a saturated, partially unsaturated or fully unsaturated chain containing 2- to 3-atoms selected from up to 3 carbon, up to 1 O, up to 1 S and up to 1 N atom, the chain optionally substituted with up to 2 substituents independently selected from $R^{15}$ on carbon atoms and $R^{16}$ on nitrogen atoms.

Embodiment I

A compound of Formula 1 or Embodiment H wherein
$Q^1$ is a phenyl ring or a naphthalenyl ring system, each ring or ring system optionally substituted with 1 to 4 substituents independently selected from $R^7$;
$Q^2$ is a phenyl ring optionally substituted with 1 to 5 substituents independently selected from $R^{10}$; and
$J^1$ is a phenyl ring or a naphthalenyl ring system, each ring or ring system optionally substituted with up to 4 substituents independently selected from $R^{7'}$.

Embodiment J

A compound of Embodiment I wherein
A is $-CH_2-$, $-CH_2O-$, $-CH_2NH-$, $-CH=CH-$, $-C\equiv C-$, $-NH-$, $-O-$, $-S-$, $-SO-$ or $-SO_2-$;
each $R^7$ is independently halogen, cyano, $C_1$-$C_2$ alkyl, $C_1$-$C_3$ haloalkyl or $C_1$-$C_3$ alkylsulfonyl;
each $R^{10}$ is independently halogen, cyano, nitro, $C_1$-$C_2$ alkyl, $C_1$-$C_3$ haloalkyl or $C_1$-$C_3$ alkylsulfonyl;
each $R^{7'}$ is independently halogen, cyano, nitro, $C_1$-$C_8$ alkyl or $C_1$-$C_8$ haloalkyl;
$Y^1$ and $Y^2$ are both O.

Embodiment K

A compound of Formula 1 or Embodiment H wherein
$Q^1$ is a phenyl ring or a naphthalenyl ring system, each ring or ring system optionally substituted with 1 to 4 substituents independently selected from $R^7$;
$Q^2$ is a phenyl ring optionally substituted with 1 to 5 substituents independently selected from $R^{10}$; and
$J^1$ is a 4- to 6-membered heterocyclic ring containing ring members selected from carbon atoms and 1 to 3 heteroatoms independently selected from up to 2 O, up to 2 S and up to 3 N atoms, wherein up to 2 carbon ring members are independently selected from C(=O) and C(=S), and the sulfur atom ring members are independently selected from $S(=O)_u(=NR^8)_v$, each ring or ring system optionally substituted with up to 3 substituents independently selected from $R^{7'}$ on carbon atom ring members and selected from $R^{9'}$ on nitrogen atom ring members.

Embodiment L

A compound of Embodiment K wherein
A is $-CH_2-$, $-CH_2O-$, $-CH_2NH-$, $-CH=CH-$, $-C\equiv C-$, $-NH-$, $-O-$, $-S-$, $-SO-$ or $-SO_2-$;
each $R^7$ is independently halogen, cyano, $C_1$-$C_2$ alkyl, $C_1$-$C_3$ haloalkyl or $C_1$-$C_3$ alkylsulfonyl;
each $R^{10}$ is independently halogen, cyano, nitro, $C_1$-$C_2$ alkyl, $C_1$-$C_3$ haloalkyl or $C_1$-$C_3$ alkylsulfonyl;
each $R^{7'}$ is independently halogen, cyano, nitro, $C_1$-$C_8$ alkyl or $C_1$-$C_8$ haloalkyl; and
$Y^1$ and $Y^2$ are both O.

Embodiment M

A compound of Formula 1 or Embodiment H wherein
$Q^1$ is a 5- to 6-membered heteroaromatic ring or an 8- to 10-membered heteroaromatic bicyclic ring system, each ring or ring system optionally substituted with up to 4 substituents independently selected from $R^7$ on carbon atom ring members and selected from $R^9$ on nitrogen atom ring members;

Q² is a phenyl ring optionally substituted with 1 to 5 substituents independently selected from R¹⁰; and J¹ is a 4- to 6-membered heterocyclic ring containing ring members selected from carbon atoms and 1 to 3 heteroatoms independently selected from up to 2 O, up to 2 S and up to 3 N atoms, wherein up to 2 carbon ring members are independently selected from C(=O) and C(=S), and the sulfur atom ring members are independently selected from $S(=O)_u(=NR^8)_v$, each ring or ring system optionally substituted with up to 3 substituents independently selected from $R^{7'}$ on carbon atom ring members and selected from $R^{9'}$ on nitrogen atom ring members.

Embodiment N

A compound of Embodiment M wherein
A is —CH₂—, —CH₂O—, —CH₂NH—, —CH=CH—, —C≡C—, —NH—, —O—, —S—, —SO— or —SO₂—;
each R⁷ is independently halogen, cyano, C₁-C₂ alkyl, C₁-C₃ haloalkyl or C₁-C₃ alkylsulfonyl;
each R¹⁰ is independently halogen, cyano, nitro, C₁-C₂ alkyl, C₁-C₃ haloalkyl or C₁-C₃ alkylsulfonyl;
each $R^{7'}$ is independently halogen, cyano, nitro, C₁-C₈ alkyl or C₁-C₈ haloalkyl; and
Y¹ and Y² are both O.

Embodiment O

A compound of Formula 1 or Embodiment H wherein
Q¹ is a 5- to 6-membered heteroaromatic ring or an 8- to 10-membered heteroaromatic bicyclic ring system, each ring or ring system optionally substituted with up to 4 substituents independently selected from R⁷ on carbon atom ring members and selected from R⁹ on nitrogen atom ring members;
Q² is a phenyl ring optionally substituted with 1 to 5 substituents independently selected from R¹⁰; and
J¹ is a phenyl ring or a naphthalenyl ring system, each ring or ring system optionally substituted with up to 4 substituents independently selected from $R^{7'}$.

Embodiment P

A compound of Embodiment O wherein
A is —CH₂—, —CH₂O—, —CH₂NH—, —CH=CH—, —C≡C—, —NH—, —O—, —S—, —SO— or —SO₂—;
each R⁷ is independently halogen, cyano, C₁-C₂ alkyl, C₁-C₃ haloalkyl or C₁-C₃ alkylsulfonyl;
each R¹⁰ is independently halogen, cyano, nitro, C₁-C₂ alkyl, C₁-C₃ haloalkyl or C₁-C₃ alkylsulfonyl;
each $R^{7'}$ is independently halogen, cyano, nitro, C₁-C₈ alkyl or C₁-C₈ haloalkyl; and
Y¹ and Y² are both O.

Specific embodiments include compounds of Formula 1 selected from the group consisting of:
N-(2,4-difluorophenyl)-2-oxo-4-[3-(phenoxymethyl)phenyl]-3-pyrrolidinecarboxamide; and
2-oxo-4-[3-(2-pyridinyloxy)phenyl]-N-(2,3,4-trifluorophenyl)-3-pyrrolidinecarboxamide.

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimethyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b1) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3 (2H)-pyridazinone, 4-(4-fluorophenyl)-6-[(2-hydroxy-6-oxo-1-cyclohexen-1-yl)carbonyl]-2-methyl-1,2,4-triazine-3,5(2H, 4H)-dione, 5-[(2-hydroxy-6-oxo-1-cyclohexen-1-yl) carbonyl]-2-(3-methoxyphenyl)-3-(3-methoxypropyl)-4 (3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, cyclopyrimorate (6-chloro-3-(2-cyclopropyl-6-methylphenoxy)-4-pyridazinyl 4-morpholinecarboxylate), 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3 (2H)-pyridazinone.

HST inhibitors also include compounds of Formulae A and B.

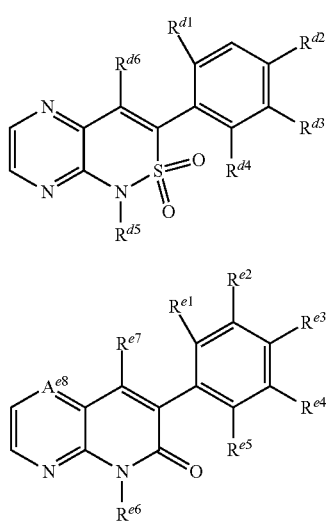

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or $-OC(=O)$-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, $-OC(=O)Et$, $-OC(=O)$-i-Pr or $-OC(=O)$-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide.

The compounds of Formula 1 can be prepared by general methods known in the art of synthetic organic chemistry. One or more of the following methods and variations as described in Schemes 1-18 can be used to prepare the compounds of Formula 1. The definitions of $R^1$, $R^2$, $R^3$, $R^4$, $R^5$, $R^6$, $Q^1$, $Q^2$, $J^1$, $J^2$, T, $Y^1$, and $Y^2$ in the compounds of Formulae 1-19 below are as defined above in the Summary of the Invention unless otherwise noted.

As shown in Scheme 1 compounds of Formula 1a (i.e. Formula 1 wherein T is -A-$J^1$, $R^1$, $R^4$ and $R^5$ are H, and $Y^1$ and $Y^2$ are O) can be prepared by reaction of acids of Formula 2 with amines of Formula 3 in the presence of a dehydrative coupling reagent such as propylphosphonic anhydride, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide. Polymer-supported reagents, such as polymer-supported cyclohexylcarbodiimide, are also suitable. These reactions are typically run at temperatures ranging from 0-60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See *Organic Process Research & Development* 2009, 13, 900-906 for coupling conditions employing propylphosphonic anhydride. The method of Scheme 1 utilizing propylphosphonic anhydride is illustrated by Step F of Synthesis Example 2.

Scheme 1

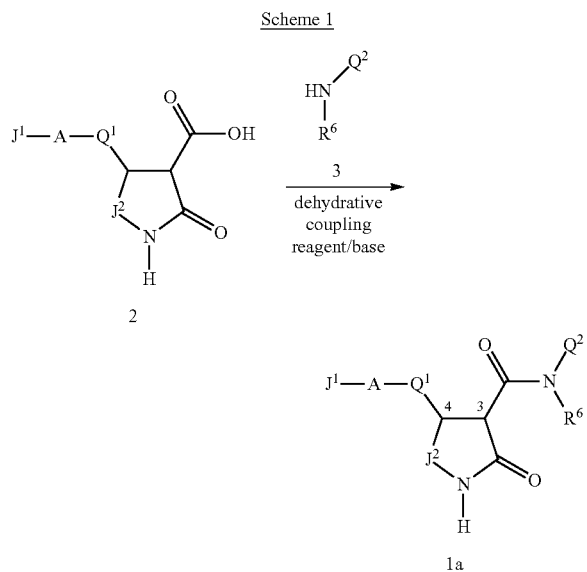

As shown in Scheme 2, compounds of Formula 2 can be prepared by hydrolysis of esters of Formula 4 by methods well known to those skilled in the art. Hydrolysis is carried out with aqueous base or aqueous acid, typically in the presence of a co-solvent. Suitable bases for the reaction include, but are not limited to, hydroxides such as sodium and potassium hydroxide and carbonates such as sodium and potassium carbonate. Suitable acids for the reaction include, but are not limited to, inorganic acids such as hydrochloric acid, hydrobromic acid and sulfuric acid, and organic acids such as acetic acid and trifluoroacetic acid. A wide variety of co-solvents are suitable for the reaction including, but not limited to, methanol, ethanol and tetrahydrofuran. The reaction is conducted at temperatures ranging from −20° C. to the boiling point of the solvent, and typically from 0 to 100° C. The method of Scheme 2 is illustrated by Step E of Synthesis Example 2.

Scheme 2

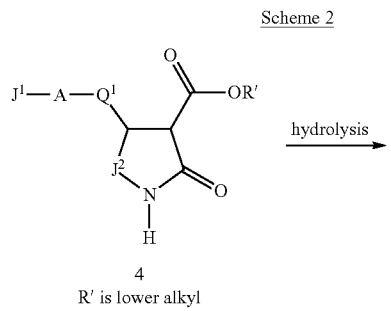

R' is lower alkyl

-continued

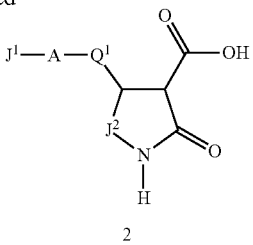

As shown in Scheme 3, a compound of Formula 4a or 4b can be obtained by reduction of a compound of Formula 5a and 5b respectively and subsequent in situ cyclization of the resulting intermediate amine. A wide variety of methods for reduction of the aliphatic nitro or nitrile group in compounds of Formula 5a or 5b are known in the literature. Methods well known to those skilled in the art include catalytic hydrogenation in the presence of palladium on carbon or Raney nickel, iron or zinc metal in acidic medium (see, for example, *Berichte der Deutschen Chemischen Gesellschaft* 1904, 37, 3520-3525), and lithium aluminum hydride. Reduction of aliphatic nitro group can also be achieved with samarium(II) iodide in the presence of a proton source such as methanol (see for example, *Tetrahedron Letters* 1991, 32 (14), 1699-1702). Alternatively sodium borohydride in the presence of a nickel catalyst such as nickel(II) acetate or nickel(II) chloride can be used (see for example, *Tetrahedron Letters* 1985, 26 (52), 6413-6416). The method of Scheme 3 utilizing sodium borohydride in the presence of nickel(II) chloride is illustrated by Step D of Synthesis Example 1.

Scheme 3

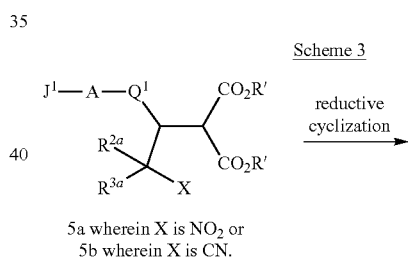

5a wherein X is NO$_2$ or
5b wherein X is CN.

R' is lower alkyl

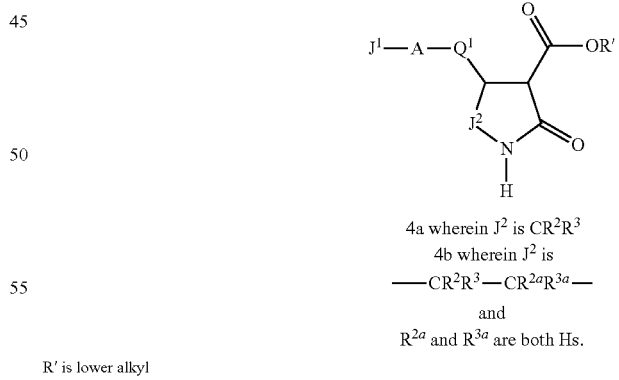

4a wherein J$^2$ is CR$^2$R$^3$
4b wherein J$^2$ is
—CR$^2$R$^3$—CR$^{2a}$R$^{3a}$—
and
R$^{2a}$ and R$^{3a}$ are both Hs.

As shown in Scheme 4, a compound of Formula 5a or 5b can be prepared by reacting diesters of Formula 6 with nitroalkanes of Formula 7a or nitriles of Formula 7b, typically in the presence of a base. Suitable bases for the reaction include alkali metal lower alkoxides such as sodium methoxide in methanol or sodium ethoxide in ethanol. Compounds of Formula 6 can readily be prepared by methods known to those skilled in the art, e.g., by Knoevenagel condensation of aldehydes and malonates (see for example G. Jones, *Organic Reactions* Volume 15, John Wiley and Sons, 1967).

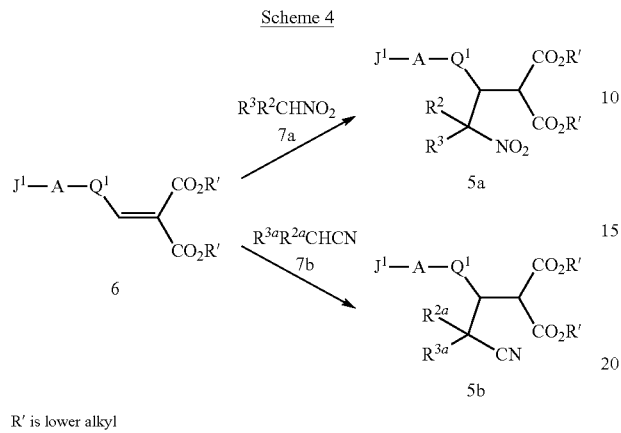

R' is lower alkyl

Compounds of Formulae 5c or 5d (i.e. Formulae 5a or 5b wherein $R^2$ and $R^3$ are H) can be prepared by reacting compounds of Formulae 8a or 8b with malonates of Formula 9 in the presence of a base as shown in Scheme 5. Suitable bases for this reaction include, but are not limited to, alkali metal lower alkoxides such as sodium methoxide in methanol or sodium ethoxide in ethanol, or bases such as lithium bis(trimethylsilyl)amide, sodium bis(trimethylsilyl)amide and lithium diisopropylamide in solvents such as tetrahydrofuran. Typically, the reaction is carried out in the range of from −78° C. to 23° C. See *Synthesis* 2005, 2239-2245 for conditions for effecting this transformation. Conditions for effecting this transformation in refluxing water in the absence of a catalyst have been reported in *Synthetic Communications* 2013, 43, 744-748.

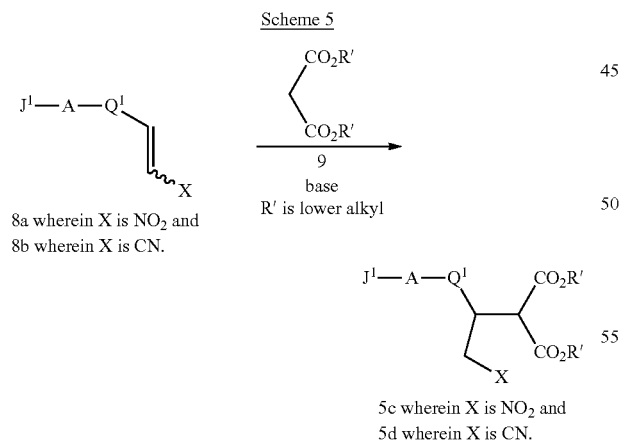

Compounds of Formula 6 can readily be prepared by Knoevenagel condensation of aldehydes of Formula 14 and malonates 9 as shown in Scheme 6. Also as shown in Scheme 6, compounds of Formulae 8a and 8b can be prepared by Knoevenagel condensation of aldehydes of Formula 14 and nitromethane.

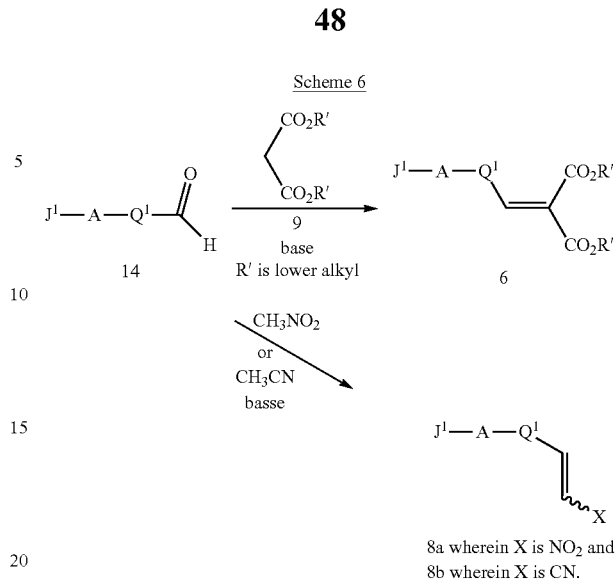

As shown in Scheme 7, aldehydes of Formula 14 can be prepared by reaction of aldehydes of Formula 20 with corresponding electrophiles of Formula 21 in the presence of base with or without a metal catalyst. In Formula 21, G denotes a leaving group, i.e. a nucleofuge. Depending upon selection of $J^1$, suitable electrophiles for the reaction can include aryl or alkyl halides such as chlorides, bromides and iodides, alkylsulfonates, acid anhydrides such as tert-butoxycarbonyl anhydride and acetic anhydride, and haloalkylsilanes such as chlorotrimethylsilane. Suitable bases for the reaction include inorganic bases such as alkali or alkaline earth metal (e.g., lithium, sodium, potassium and cesium) hydroxides, alkoxides, carbonates, and phosphates, and organic bases such as triethylamine, N,N-diisopropylethylamine and 1,8-diazabicyclo[5.4.0]undec-7-ene. Suitable catalysts include palladium, nickel, rhodium or copper with or without ligands such as phosphines or N-heterocyclic carbenes. A wide variety of solvents are suitable for the reaction including, for example but not limited to, tetrahydrofuran, dichloromethane, N,N-dimethylformamide, N,N-dimethylacetamide, N-methylpyrrolidinone, acetonitrile, $C_2$-$C_6$ alcohols and acetone as well as mixtures of these solvents. This reaction is conducted at temperatures ranging from −20 to 200° C., and typically between 0 and 50° C. For an example, when A is —CH$_2$OH, see Organic and Biomolecular Chemistry 2013, 11, 3046-3056. Aldehydes of Formula 20 are commercially available or readily prepared from commercially available material by a skilled one in the art.

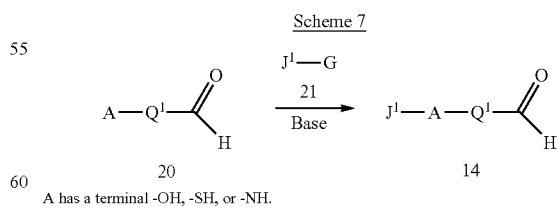

A has a terminal -OH, -SH, or -NH.

When A comprises 1-3 C atoms, a compound of Formula 14 can be made by one skilled in the art using standard transition metal cross coupling methods. For a representative palladium catalyzed Heck coupling procedure see:

Bioorg. Chem. 2010, 38, 139-143. For an example of a palladium catalyzed aryl halide trialkylbismuth procedure see: Synlett 2010, 19, 2936-2940. For a palladium catalyzed Suzuki type reactions see: J. Med. Chem. 2000, 43, 3076 and J. Med. Chem. 2012, 43, 1831-1843.

Compounds of Formulae 5a' and 5a" can be prepared stereoselectively by reacting nitroalkenes of Formula 8a with malonates of Formula 9 in the presence of a chiral catalyst and optionally in the presence of a suitable base as shown in Scheme 7A. Suitable catalysts include, but are not limited to Ni(II) with vicinal diamine ligands such as Ni(II) Bis[(R,R)—N,N'-dibenzylcyclohexane-1,2-diamine]dibromide, Ni(II) Bis[(S,S)—N,N-dibenzylcyclohexane-1,2-diamine]dibromide or nickel(II) bromide with chiral 1,1'-bi(tetrahydroisoquinoline) type diamines. Suitable organic bases for this reaction include, but are not limited to, piperidine, morpholine, triethylamine, 4-methylmorpholine or N,N-diisopropylethylamine. This transformation can be accomplished neat or in solvents such as tetrahydrofuran, toluene or dichloromethane. Typically, the reaction is carried out in the range of from −78° C. to 80° C. using 0 to 1 equivalent of catalyst and optionally 0 to 1 equivalent of a base. Conditions for effecting this transformation have been reported in J. Am. Chem. Soc. 2005, 9958-9959 or Eur. J. Org. Chem. 2011, 5441-5446 for conditions. Nitroalkenes of Formula 8a can readily be prepared from aldehydes and nitromethane by methods known to those skilled in the art.

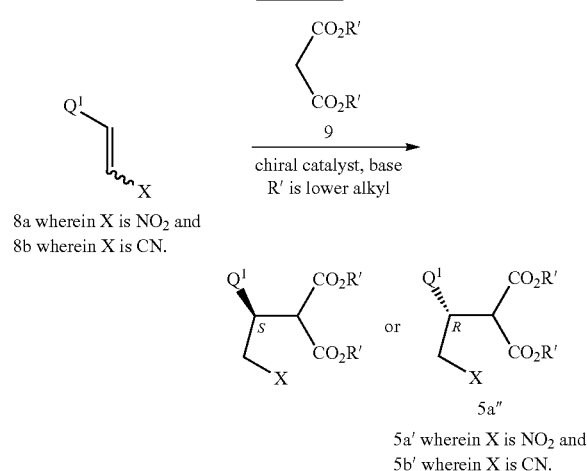

Scheme 7A 8a wherein X is $NO_2$ and
8b wherein X is CN.

5a' wherein X is $NO_2$ and
5b' wherein X is CN.

As shown in Scheme 8, compounds of Formula 1aa and 1ab can also be prepared by reductive cyclization of compounds of Formula 10a and 10b analogous to the method of Scheme 3. As also shown in Scheme 8, compounds of Formula 1ba and 1bb (i.e. Formula 1 wherein $R^1$ is OH, $R^4$ and $R^5$ are H, and $Y^1$ and $Y^2$ are O) can be prepared from compounds of Formula 10b by catalytic transfer hydrogenation with ammonium formate in the presence of palladium on carbon, and subsequent in situ cyclization of the intermediate hydroxylamine. See J. Med. Chem. 1993, 36, 1041-1047 for catalytic transfer hydrogenation/cyclization conditions to produce N-hydroxypyrrolidinones.

Scheme 8

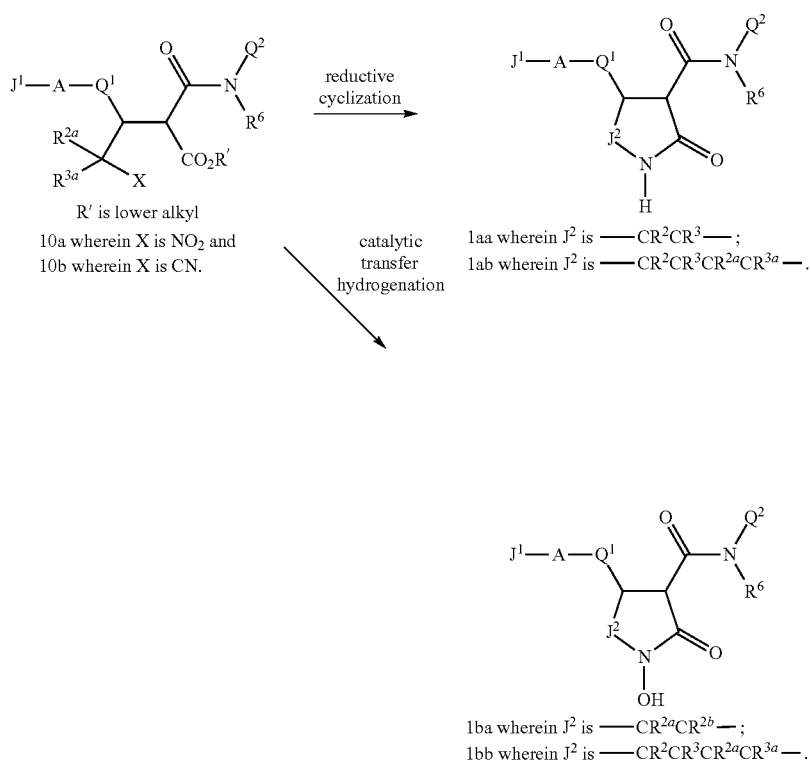

R' is lower alkyl
10a wherein X is $NO_2$ and
10b wherein X is CN.

1aa wherein $J^2$ is —$CR^2CR^3$—;
1ab wherein $J^2$ is —$CR^2CR^3CR^{2a}CR^{3a}$—.

1ba wherein $J^2$ is —$CR^{2a}CR^{2b}$—;
1bb wherein $J^2$ is —$CR^2CR^3CR^{2a}CR^{3a}$—.

As shown in Scheme 9, compounds of Formula 10a and 10b can be prepared by 5 reacting compounds of Formula 11 with a compound of Formula 7a or a compound of Formula 7b in a solvent, in the presence of a base analogous to the method described in Scheme 4.

Scheme 9

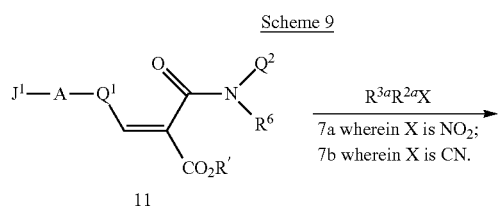

10a wherein X is NO$_2$;
10b wherein X is CN.

As shown in Scheme 10, compounds of Formula 10aa (i.e. Formula 10a wherein R$^{2a}$ and R$^{3a}$ are H) can be prepared, analogous to the method of Scheme 5, by reacting nitroalkenes of Formula 8 with malonates of Formula 12.

Scheme 10

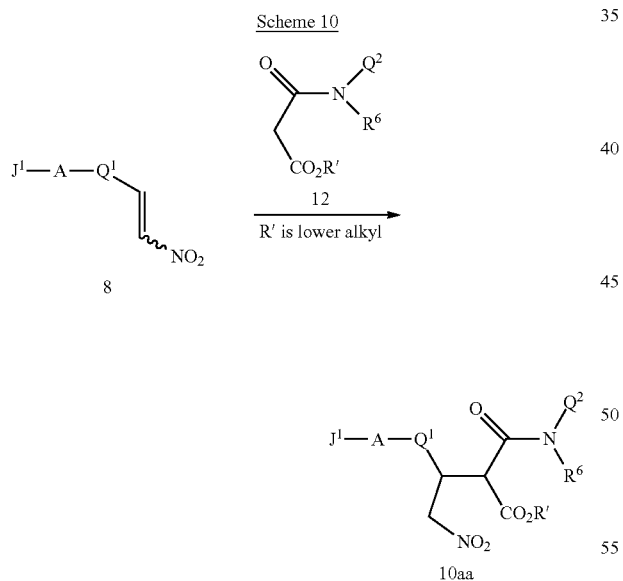

As shown in Scheme 11, compounds of Formula 11 can be prepared by reaction of malonic amide of Formula 12 with aldehydes of Formula 14 by methods known to those skilled in the art. As also shown in Scheme 11, malonic amides of Formula 12 can readily be prepared from lower alkyl malonyl chlorides of Formula 13 such as methyl malonyl chloride and amines of Formula 3 by methods known to those skilled in the art.

Scheme 11

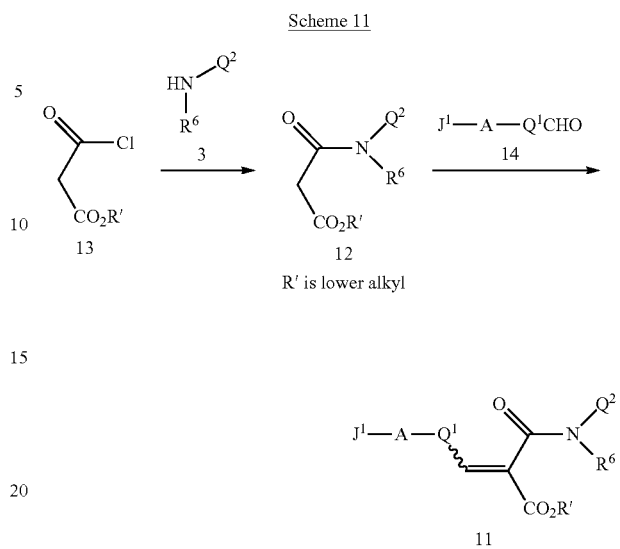

R' is lower alkyl

As shown in Scheme 12, mixtures of compounds of Formula 1c (i.e. Formula 1 wherein R$^1$ and R$^5$ are H, R$^4$ is halogen and Y$^1$ and Y$^2$ are O) and Formula 1d (i.e. Formula 1 wherein R$^1$ and R$^4$ are H, R$^5$ is halogen and Y$^1$ and Y$^2$ are O) can be prepared by reacting compounds of Formula 1a with a halogen source in a solvent, in the presence or absence of an initiator. Separation of the regioisomers produced in this reaction can be achieved by standard methods such as chromatography or fractional crystallization. Suitable halogen sources for this reaction include bromine, chlorine, N-chlorosuccinimide, N-bromosuccinimide and N-iodosuccinimide. Suitable initiators for this reaction include 2,2'-azobisisobutyronitrile (AIBN) and benzoyl peroxide. Typically, the reaction is carried out in solvents such as dichloromethane in the range of from 0° C. to the boiling point of the solvent.

Scheme 12

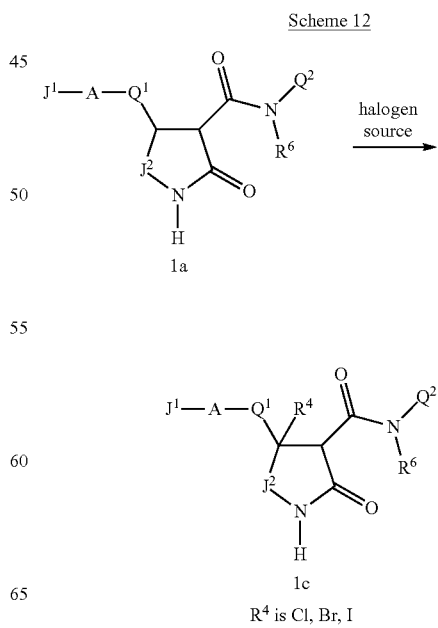

R$^4$ is Cl, Br, I

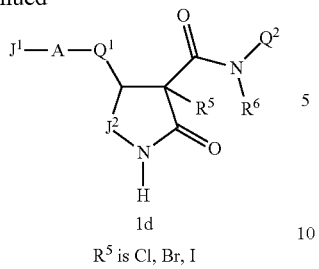

1d

R⁵ is Cl, Br, I

As shown in Scheme 13, compounds of Formula 1e (i.e. Formula 1 wherein $R^1$ is $NH_2$, $R^4$ and $R^5$ are H and $Y^1$ and $Y^2$ are O) can be prepared by reacting compounds of Formula 1a with an aminating reagent such as O-(diphenylphosphinyl)hydroxylamine and hydroxylamino-O-sulphonic acid. For procedures, conditions and reagents see *Bioorg. & Med. Chem. Lett.* 2009, 19, 5924-5926 and *J. of Org. Chem.* 2002, 67, 6236-6239.

Scheme 13

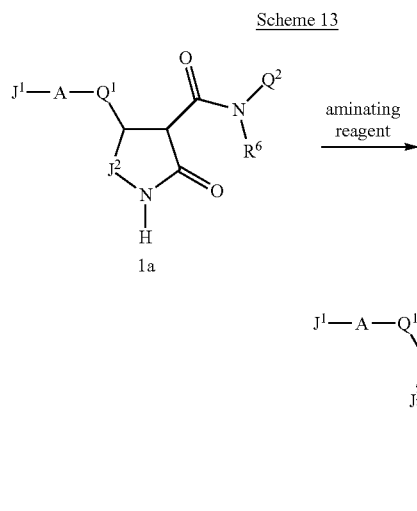

1e

As shown in Scheme 14, compounds of Formula 1f (i.e. Formula 1 wherein $R^4$, $R^5$ and $R^6$ are H and $Y^1$ and $Y^2$ are O) can be produced by reaction of compounds of Formula 15 with isocyanates (i.e. Formula 16 wherein $Y^2$ is O) or isothiocyanates (i.e. Formula 16 wherein $Y^2$ is S) in the presence of base. Examples of the base which can be used for the present process include those listed for the method of Scheme 4. The reaction temperature can be selected from the range of from −78° C. to the boiling point of the inert solvent used. Typically, the reaction is carried out at temperatures ranging from −78° C. to 100° C. in solvents such as toluene.

Scheme 14

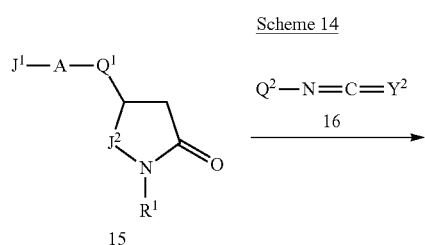

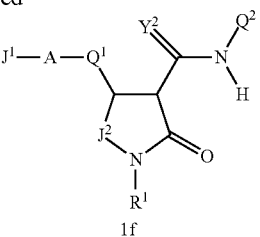

1f

As shown in Scheme 15, compounds of Formula 15 can be prepared by reaction of compounds of Formula 17 with corresponding electrophiles of Formula 18 in the presence of base. In Formula 18, G denotes a leaving group, i.e. a nucleofuge. Depending upon selection of $R^1$, suitable electrophiles for the reaction can include alkyl halides such as chlorides, bromides and iodides, alkylsulfonates, acid anhydrides such as tert-butoxycarbonyl anhydride and acetic anhydride, and haloalkylsilanes such as chlorotrimethylsilane. Suitable bases for the reaction include inorganic bases such as alkali or alkaline earth metal (e.g., lithium, sodium, potassium and cesium) hydroxides, alkoxides, carbonates, and phosphates, and organic bases such as triethylamine, N,N-diisopropylethylamine and 1,8-diazabicyclo[5.4.0]undec-7-ene. A wide variety of solvents are suitable for the reaction including, for example but not limited to, tetrahydrofuran, dichloromethane, N,N-dimethylformamide, N,N-dimethylacetamide, N-methylpyrrolidinone, acetonitrile, $C_2$-$C_6$ alcohols and acetone as well as mixtures of these solvents. This reaction is conducted at temperatures ranging from −20 to 200° C., and typically between 0 and 50° C.

Scheme 15

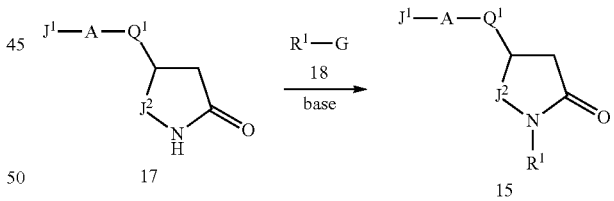

As shown in Scheme 16, compounds of Formula 17 can be prepared by decarboxylation of acids of Formula 2 by methods well known to those skilled in the art. Decarboxylation is carried by heating compounds of Formula 2 in a solvent, typically in the presence of an acid. Suitable acids for the reaction include, but are not limited to, p-toluenesulfonic acid. A wide variety of co-solvents are suitable for the reaction including, but not limited to, toluene, isopropanol acetate and isobutyl methylketone. The reaction is conducted at temperatures ranging from −20° C. and to the boiling point of the solvent, and typically from 0 to 150° C.

Scheme 16

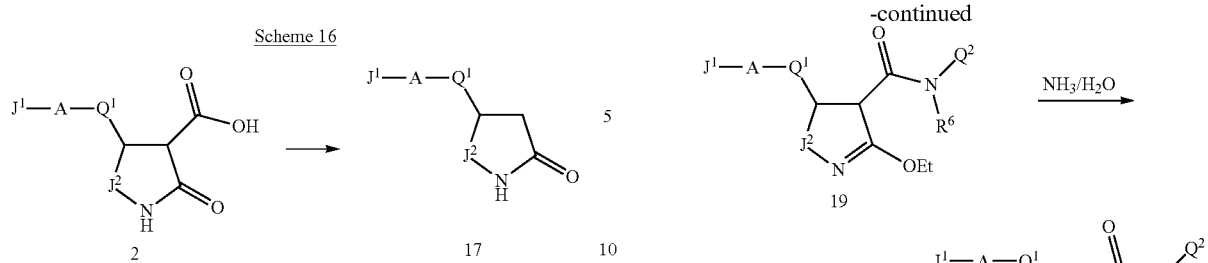

As shown in Scheme 17, compounds of Formula 1g (i.e. Formula 1 wherein $R^1$ is H, $R^4$ and $R^5$ are H, and $Y^1$ and $Y^2$ are S) can be prepared by reacting compounds of Formula 1a with at least two equivalents of a thionation reagent such as Lawesson's reagent, tetraphosphorus decasulfide or diphosphorus pentasulfide in a solvent such as tetrahydrofuran or toluene. Typically, the reaction is carried out at temperatures ranging from 0 to 115° C. One skilled in the art recognizes that using less than two equivalents of the thionating reagent can provide mixtures comprising Formula 1 products wherein $Y^1$ is O and $Y^2$ is S, or $Y^1$ is S and $Y^2$ is O, which can be separated by conventional methods such as chromatography and crystallization.

Scheme 17

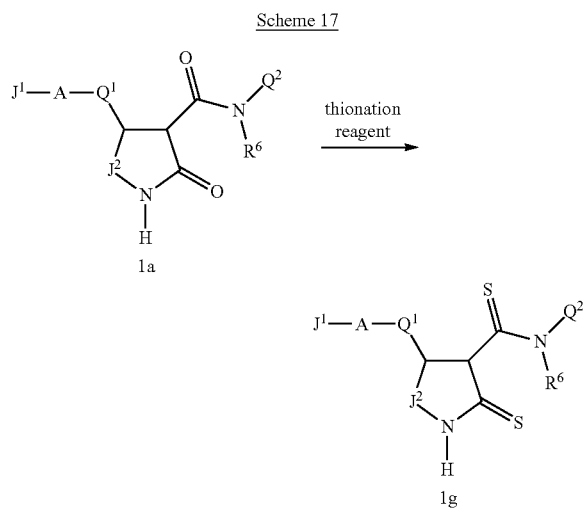

As shown in Scheme 18, compounds of Formula 1h (i.e. Formula 1 wherein $R^1$, $R^4$, $R^5$ are H, $Y^2$ is O and $Y^1$ is NH) can be prepared by alkylation of compounds of Formula 1a triethyloxonium tetrafluoroborate (Meerwein's reagent) followed by treatment of the resulting imino ether of Formula 19 with aqueous ammonia.

Scheme 18

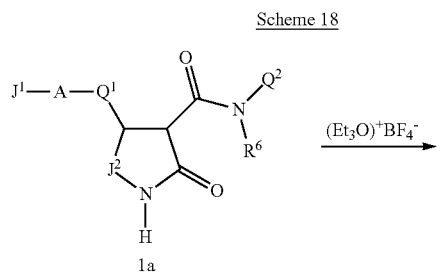

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in CDCl$_3$ at 500 MHz unless otherwise noted; "s" means singlet, "d" means doublet, "t" means triplet, "q" means quartet, "m" means multiplet, "d" means doublet. Mass spectra (MS) are reported as the molecular weight of the highest isotopic abundance parent ion (M+1) formed by addition of H+(molecular weight of 1) to the molecule, or (M−1) formed by the loss of H+(molecular weight of 1) from the molecule, observed by using liquid chromatography coupled to a mass spectrometer (LCMS) using either atmospheric pressure chemical ionization (AP+) where "amu" stands for unified atomic mass units.

Synthesis Example 1

Preparation N-(2-Fluorophenyl)-2-oxo-4-[3-(2-pyridinyloxy)phenyl]-3-pyrrolidinecarboxamide (Compound 34)

Step A: Preparation of 3-(2-pyridinyloxy)benzaldehyde

2-Fluoropyridine (20.0 g, 164 mmol) was dissolved in 150 mL N,N-dimethylformamide and then treated with potassium tert-butoxide (19.9 g, 177 mmol). The reaction exothermed to 57° C. and then was allowed to cool to ambient temperature over 1 hour. 3-Hydroxybenzaldehyde (13.9 mL, 162 mmol) was added and the mixture was heated to 120° C. overnight. The reaction mixture was allowed to cool to ambient temperature and then partitioned between ethyl acetate and 1N aqueous HCl solution. The organic layer was washed with brine, dried over magnesium sulfate and concentrated to yield a brown sludge which was subsequently triturated with diethyl ether. The resulting solid was isolated by filtration and air dried to afford 14.9 g of the title compound.

$^1$H NMR (DMSO-d$_6$) δ 10.01 (s, 1H), 8.17 (m, 1H), 7.91 (m, 1H), 7.78 (m, 1H), 7.66 (t, 1H), 7.63 (s, 1H), 7.50 (m, 1H), 7.16-7.20 (m, 1H), 7.13 (d, 1H).

Step B: Preparation of 2-[3-[(1E)-2-nitroethenyl]phenoxy]pyridine

To a solution of 3-(pyrid-2-yloxy)benzaldehyde (alternatively known as 3-(2-pyridinyloxy)benzaldehyde, i.e. the product of Step A, 20.1 g, 101 mmol) in 250 mL of 1-chlorobutane was added nitromethane (6.54 mL, 121 mmol), piperdine (0.988 mL, 10.0 mmol) and glacial acetic acid (0.577 mL, 10.0 mmol). The mixture was then heated to reflux for 48 hours with azeotropic removal of water. The reaction was allowed to cool to ambient temperature. The reaction mixture was concentrated onto Celite® diatomaceous filter aid and then purified by medium pressure liquid chromatography (0% to 15% ethyl acetate in hexanes as eluent) to yield 19.2 g of the title compound as a yellow oil.

$^1$H NMR δ 8.19 (m, 1H), 7.99 (d, 1H), 7.74 (m, 1H), 7.56 (m, 1H), 7.48 (t, 1H) 7.36 (m, 2H), 7.29 (m, 1H), 7.05 (m, 1H), 6.99 (d, 1H).

Step C: Preparation of 1,3-diethyl 2-[2-nitro-1-[3-(2-pyridinyloxy)phenyl]ethyl]propanedioate 2-[3-[(1E)-2-nitroethenyl]phenoxy]pyridine (i.e. the product of Step B, 19.4 g, 105 mmol), diethyl malonate (14.5 mL, 95.2 mmol) and Ni(II) Bis[N,N'-dibenzylcyclohexane-1,2-diamine]dibromide (0.955 g, 1.19 mmol) were refluxed in dichloromethane for 48 hours. The reaction mixture was then cooled to ambient temperature, concentrated onto Celite® diatomaceous filter aid under reduced pressure, and then purified by medium pressure liquid chromatography eluting with 0% to 50% ethyl acetate in hexanes to afford 30.2 g of the title compound as a colorless oil.

$^1$H NMR (500 MHz, DMSO-d$_6$) δ 8.15 (m, 1H) 7.86 (m, 1H) 7.34 (m, 1H) 7.15 (m, 3H) 7.03 (m, 1H) 6.96 (m, 1H) 4.99 (m, 2H) 4.17 (m, 2H) 4.09 (m, 1H) 4.03 (m, 1H) 3.89 (m, 2H) 1.18 (t, 3H) 0.92 (t, 3H).

Step D: Preparation of Ethyl 2-oxo-4-[3-(2-pyridinyloxy)phenyl]-3-pyrrolidinecarboxylate 1,3-Diethyl 2-[2-nitro-1-[3-(2-pyridinyloxy)phenyl]ethyl]propanedioate (i.e. the product of Step C, 30.1 g, 74.9 mmol) was dissolved in 500 mL of ethanol at ambient temperature. NiCl$_2$.6H$_2$O (17.8 g, 74.9 mmol) was added and the mixture was stirred until completely dissolved. The reaction mass was then cooled to 0° C. in an ice bath and then sodium borohydride (8.50 g, 225 mmol) was added slowly, so that the temperature did not exceed 5° C. Upon complete addition, the ice bath was removed and the reaction mass was stirred at ambient temperature overnight. The ethanol was then removed under reduced pressure and 500 mL ethyl acetate and 1.25 L of saturated ammonium chloride solution were added, and the reaction was stirred until the next day. The organic layer was separated from the aqueous layer and then concentrated onto silica gel under reduced pressure and then purified by MPLC eluting with 0% to 100% ethyl acetate in hexanes to give 7.5 g of the title compound as a yellow oil.

$^1$H NMR δ 8.19 (m, 1H), 7.71 (m, 1H), 7.37 (m, 1H), 7.05 (m, 4H), 6.93 (m, 1H), 6.37 (bs, 1H), 4.24 (m, 2H), 4.13 (m, 1H), 3.82 (m, 1H), 3.55 (d, 1H), 3.45 (m, 1H), 1.27 (m, 3H).

Step E: Preparation of N-(2-Fluorophenyl)-2-oxo-4-[3-(2-pyridinyloxy)phenyl]-3-pyrrolidinecarboxamide Ethyl 2-oxo-4-[3-(2-pyridinyloxy)phenyl]-3-pyrrolidinecarboxylate (i.e. the product of Step D, 0.40 g, 1.2 mmol) was added to 2-fluoroaniline (2.0 mL, 6.8 mmol) and heated in a CEM Microwave reactor for 45 minutes at 190° C. The reaction mixture was cooled to ambient temperature and then diluted with 200 mL dichloromethane. This solution was concentrated under reduced pressure onto Celite® and then purified by MPLC (0% to 100% ethyl acetate in hexanes as eluent) resulting in 0.23 g of the title compound, a product of the present invention, as a solid.

$^1$H NMR δ 10.04 (s, 1H), 8.13 (m, 2H), 8.00 (m, 1H), 7.83 (m, 1H), 7.38 (m, 1H), 7.12 (m, 8H), 4.00 (m, 2H), 3.70 (t, 1H), 3.25 (t, 1H).

Synthesis Example 2

Preparation of N-(2,3-difluorophenyl)-2-oxo-4-[3-[[3-(trifluoromethyl)-1H-pyrazol-1-yl]methyl]phenyl]-3-pyrrolidinecarboxamide (Compound 25)

Step A: Preparation of 3-[[3-(Trifluoromethyl)-1H-pyrazole-1-yl]methyl]benzaldehyde 3-(Trifluoromethyl)pyrazole (0.82 g, 6.0 mmol), 3-(bromomethyl)benzaldehyde (1.0 g, 5.0 mmol) and potassium carbonate (2.1 g, 15 mmol) were combined in 50 mL N,N-dimethylformamide and heated to 80° C. for 18 hours. The reaction mixture was cooled to ambient temperature and then partitioned between ethyl acetate and brine. The organic layer was dried over magnesium sulfate and concentrated under reduced pressure to yield a green oil which was adsorbed onto silica gel and then purified by MPLC eluting with 0% to 100% ethyl acetate in hexanes to afford 0.82 g of the title compound.

$^1$H NMR δ 10.01 (s, 1H), 7.86 (m, 1H), 7.76 (s, 1H), 7.56 (m, 1H), 7.50 (m, 1H), 7.45 (m, 1H), 6.58 (d, 1H), 5.44 (s, 2H).

Step B: Preparation of 1-[[3-[(1E)-2-Nitroethenyl] phenyl]methyl]-3-(trifluoromethyl)-1H-pyrazole (i.e. 1-[[3-[(1E)-2-Nitroethenyl]phenyl]methyl]-3-(trifluoromethyl)-1H-pyrazole)

To a solution of 3-[[3-(trifluoromethyl)-1H-pyrazole-1-yl]methyl]benzaldehyde (i.e. the product of Step A, 16.5 g, 65 mmol) in 100 mL of 1-chlorobutane was added nitromethane (4.2 mL, 78 mmol), piperdine (0.64 mL, 6.5 mmol) and glacial acetic acid (0.37 mL, 6.5 mmol). The mixture was then heated to reflux for 48 hours with azeotropic removal of water. The reaction was allowed to cool to ambient temperature. The reaction mixture was concentrated onto Celite® diatomaceous filter aid and then purified by MPLC, eluting with 0% to 15% ethyl acetate in hexanes to yield 11.2 g of the title compound as a yellow solid.

$^1$H NMR (500 MHz, CHLOROFORM-d) δ 7.97 (d, 1H), 7.55 (m, 2H), 7.46 (m, 2H), 7.38 (m, 2H), 6.58 (d, 1H), 5.40 (s, 2H).

Step C: Preparation of 1,3-diethyl 2-[2-nitro-1-[3-[[3-(trifluoromethyl)-1H-pyrazol-1-yl]methyl]phenyl]ethyl]propanedioate 1-[[3-[(1E)-2-Nitroethenyl]phenyl]methyl]-3-(trifluoromethyl)-1H-pyrazole (i.e. 1-[[3-[(1E)-2-Nitroethenyl]phenyl]methyl]-3-(trifluoromethyl)-1H-pyrazole, i.e. the product of Step B, 11 g, 38 mmol), diethyl malonate (6.9 mL, 45 mmol) and Ni(II) Bis[N,N'-dibenzylcyclohexane-1,2-diamine]dibromide (0.46 g, 0.57 mmol) were stirred in dichloromethane for approximately 16 hours. The reaction mixture was then cooled to ambient temperature, concentrated onto Celite® diatomaceous filter aid under reduced pressure, and then purified by MPLC eluting with 0% to 50% ethyl acetate in hexanes to afford 11 g of the title compound as a yellow oil.

$^1$H NMR δ 7.34 (m, 2H), 7.23 (d, 1H), 7.15 (m, 2H), 6.54 (d, 1H), 5.32 (m, 2H), 4.88 (m, 2H), 4.21 (m, 3H), 3.98 (q, 2H), 3.78 (d, 1H), 1.25 (t, 3H), 1.01 (t, 3H).

Step D: Preparation of Ethyl 2-oxo-4-[3-[[3-(trifluoromethyl)-1H-pyrazole-1-yl]methyl]phenyl]-3-pyrrolidinecarboxylate 1,3-Diethyl 2-[2-nitro-1-[3-[[3-(trifluoromethyl)-1H-pyrazol-1-yl]methyl]phenyl]ethyl]propanedioate (i.e. the product of Step C, 30.1 g, 74.9 mmol) was dissolved in 500 mL of ethanol at ambient temperature. NiCl$_2$·6H$_2$O (17.8 g, 74.9 mmol) was added and the mixture was stirred until completely dissolved. The reaction mass was then cooled to 0° C. in an ice bath and then sodium borohydride (8.50 g, 225 mmol) was added slowly so that the temperature did not exceed 5° C. Upon complete addition, the ice bath was removed and the reaction mass was stirred at ambient temperature for 3 hours. 300 mL of ethyl acetate and 300 mL of saturated ammonium chloride solution were added, and the reaction was stirred until the organic layer was clear and the aqueous layer was blue. The organic layer was separated from the aqueous layer, and the aqueous layer was extracted again with ethyl acetate. The combined organic layers were washed with ammonium chloride, dried over magnesium sulfate and then concentrated onto silica gel under reduced pressure and then purified by MPLC eluting with 0% to 100% ethyl acetate in hexanes to afford 3.5 g of the title compound as a yellow oil with some impurities which was used without additional purification. MS (M–1)=380 amu.

Step E: Preparation of 2-oxo-4-[3-[[3-(trifluoromethyl)-1H-pyrazole-1-yl]methyl]phenyl]-3-pyrrolidinecarboxylic acid Ethyl 2-oxo-4-[3-[[3-(trifluoromethyl)-1H-pyrazole-1-yl]methyl]phenyl]-3-pyrrolidinecarboxylate (i.e. the product of Step D, 3.78 g, 9.1 mmol) was dissolved in 65 mL of ethanol and then 1.4 mL of 50% sodium hydroxide solution was added over 5 minutes. The reaction was then stirred overnight at ambient temperature. The mixture was diluted with water until the white precipitate was dissolved. The organic layer was extracted twice with 125 mL diethyl ether and then acidified to a pH of 2 with concentrated hydrochloric acid. The aqueous layer was then extracted with ethyl acetate. The ethyl acetate layer was washed with brine and dried over magnesium sulfate and concentrated under reduced pressure to yield 1.9 g of the title compound as a pink glass.

$^1$H NMR (DMSO-d$_6$) δ 12.74 (bs, 1H), 8.09 (d, 2H), 7.33 (m, 3H), 7.12 (m, 1H), 6.74 (d, 1H), 5.41 (s, 2H), 3.83 (m, 2H), 3.51 (m, 2H).

Step F: Preparation of N-(2,3-Difluorophenyl)-2-oxo-4-[3-[[3-(trifluoromethyl)-1H-pyrazol-1-yl]methyl]phenyl]-3-pyrrolidinecarboxamide 2-oxo-4-[3-[[3-(trifluoromethyl)-1H-pyrazole-1-yl]methyl]phenyl]-3-pyrrolidinecarboxylic acid (i.e. the product of Step E, 0.33 g, 0.92 mmol), triethyl amine (0.38 mL, 0.28 mmol) and 2,3-difluoroaniline (0.14 g, 1.1 mmol) were dissolved in 25 mL of dichloromethane and stirred at ambient temperature for 15 minutes and then treated with 50% propylphosphonic anhydride (T3P®) in ethyl acetate (1.8 mL, 3.1 mmol) and stirred overnight. The reaction mixture was concentrated under reduced pressure and then purified by MPLC eluting with 0% to 100% ethyl acetate in hexanes to afford 0.092 g of the title compound, a product of the present invention, as a solid.

$^1$H NMR (DMSO-d$_6$) δ 10.22 (s, 1H), 8.21 (s, 1H), 8.07 (d, 1H), 7.77 (m, 1H), 7.34 (m, 3H), 7.16 (m, 3H), 6.71 (d, 1H), 5.42 (s, 2H), 4.02 (m, 1H), 3.92 (m, 1H), 3.67 (t, 1H), 3.26 (t, 1H).

Synthesis Example 3

Preparation of N-(2-fluorophenyl)-4-[3-[(methoxyimino)methyl]phenyl]-1-methyl-2-oxo-3-pyrrolidinecarboxamide (Compound 53)

Step A: Preparation of 1,3-diethyl 2-[(3-iodophenyl)methylene]propanedioate

To a solution of 3-iodobenzaldehyde (10 g, 43 mmol) in benzene (100 mL), was added diethyl malonate (8.3 g, 52 mmol) and piperidine (0.73 g, 8.6 mmol) at 5° C. The reaction mixture was heated to the reflux temperature of the solvent with a Dean-Stark apparatus to remove water for 24 h. The reaction mixture was evaporated to give the crude product which was purified by silica gel column chromatography eluting with a 5% to 20% gradient of ethyl acetate in petroleum ether gave to the title product (17 g).

$^1$H NMR (400 MHz) δ 7.80 (s, 1H), 7.60 (s, 1H), 7.40 (m, 1H), 7.30 (s, 1H), 7.10 (m, 1H), 4.35 (m, 4H), 1.77 (m, 6H).

Step B: Preparation of 1,3-diethyl 2-[1-(3-iodophenyl)-2-nitroethyl]propanedioate To a solution of 1,3-diethyl 2-[(3-iodophenyl)methylene]propanedioate (i.e. the compound prepared in Step A, 17 g, 45 mmol) in ethanol (170 mL), was added nitromethane (28 g, 450 mmol) and 20% sodium methoxide in methanol (0.25 g, 4.55 mmol) at 5° C. and the reaction mixture was stirred at ambient temperature for 16 h. The reaction mixture was evaporated to give the title crude compound (16 g) which was used without further purification.

$^1$H NMR (400 MHz) δ 7.60 (t, 2H), 7.20 (d, 1H), 7.10 (t, 1H), 4.95 (m, 2H), 4.20 (m, 3H), 4.00 (m, 2H), 3.75 (d, 1H), 1.20 (m, 6H).

Step C: Preparation of ethyl 4-(3-iodophenyl)-2-oxo-3-pyrrolidinecarboxylate To a solution of 1,3-diethyl 2-[1-(3-iodophenyl)-2-nitroethyl]propanedioate (i.e. the compound prepared in Step B, 16 g, 36 mmol) in ethanol (150 mL)/water (32 mL) was added iron powder (10 g, 180 mmol), ammonium chloride (1.0 g, 18 mmol) and the reaction mixture was heated at 110° C. for 24 h. The reaction mixture was filtered through Celite® diatomaceous earth filter aid and the filtrate was concentrated. Water was added to the crude residue, and the mixture was extracted (3×) with ethyl acetate. The combined organic layers were washed with water, brine and then dried over sodium sulfate. The solvent was evaporated to provide the title compound as a crude intermediate (15 g). A 500 mg sample of the crude intermediate was purified by preparative thin-layer chromatography to provide 250 mg of the title compound.

$^1$H NMR (400 MHz) δ 7.60 (m, 2H), 7.20 (m, 1H), 7.10 (m, 1H), 6.10 (s, 1H), 4.20 (m, 2H), 4.00 (m, 2H), 3.63 (t, 1H), 3.40 (m, 1H), 3.30 (m, 1H), 1.23 (m, 3H).

Step D: Preparation of 4-(3-iodophenyl)-2-oxo-3-pyrrolidinecarboxylic acid

To a solution of ethyl 4-(3-iodophenyl)-2-oxo-3-pyrrolidinecarboxylate (i.e. the compound prepared in Step C, 9.0 g, 25 mmol) in tetrahydrofuran (50 mL) and water (10 mL) was added lithium hydroxide monohydrate (1.6 g, 38 mmol) at 0° C. and the reaction mixture was stirred at ambient temperature for 4 h. The reaction mixture was then evaporated and the solid was mixed in water. The aqueous mixture was extracted with ethyl acetate and the organic layer was discarded. The aqueous layer was acidified with concentrated hydrochloric acid at 0° C. The resulting solid was collected by filtration and dried under vacuum to give the title compound (5 g) as an off-white solid.

$^1$H NMR (400 MHz) δ 12.89 (s, 1H), 8.10 (s, 1H), 7.65 (d, 1H), 7.53 (d, 1H), 7.39 (d, 1H), 7.18 (t, 1H), 3.81 (m, 1H), 3.50 (m, 2H), 3.20 (m, 1H).

Step E: Preparation of 4-(3-iodophenyl)-1-methyl-2-oxo-3-pyrrolidinecarboxylic acid Potassium t-butoxide (37 mL, 1 M solution in tetrahydrofuran) was cooled to 0° C. To this solution was added 4-(3-iodophenyl)-2-oxo-3-pyrrolidinecarboxylic acid (i.e. the compound prepared in Step D, 5.0 g, 15 mmol) in tetrahydrofuran was slowly added and stirred for 10 min. Methyl bromide (25% in acetonitrile, 14 mL, 38 mmol), was added and the reaction mixture was stirred for 4 h. The reaction mixture was diluted with acetonitrile and acidified with 1 N aqueouse hydrochloric acid at 0° C. The reaction mixture was then extracted (3×) with ethyl acetate and the combined organics were washed with brine and dried over sodium sulfate to give a crude residue which was washed with diethyl ether to give the title compound (2.3 g) as an off-white solid.

$^1$H NMR (400 MHz) δ 12.77 (s, 1H), 7.74 (s, 1H), 7.65 (d, 1H), 7.38 (d, 1H), 7.15 (t, 1H), 3.81 (m, 2H), 3.62 (m, 1H), 3.45 (d, 1H), 2.80 (s, 3H).

Step F: Preparation of N-(2-fluorophenyl)-4-(3-iodophenyl)-1-methyl-2-oxo-3-pyrrolidinecarboxamide To a solution of 4-(3-iodophenyl)-1-methyl-2-oxo-3-pyrrolidinecarboxylic acid (i.e. the compound prepared in Step E, 0.5 g, 1.4 mmol) and 2-fluoroaniline (0.15 mL, 1.6 mmol) in N,N-dimethylformamide (10 mL) was added triethylamine (0.6 mL, 4.3 mmol) and stirred at ambient temperature for 10 min. Then propylphosphonic anhydride (T3P®) solution (50% in ethyl acetate, 1.7 mL, 2.89 mmol) was added at 0° C. and stirred for 2 h. The reaction mixture was then diluted with water and extracted with ethyl acetate. The combined organic layers were washed with water and brine and then dried over sodium sulfate. The solvent was evaporated to give a crude residue which was washed with diethyl ether/pentane to give the title compound (0.4 g) as an off-white solid.

$^1$H NMR (400 MHz) δ 10.08 (s, 1H), 8.00 (m, 1H), 7.75 (s, 1H), 7.63 (d, 1H), 7.37 (d, 1H), 7.35 (m, 1H), 7.15 (m, 3H), 3.95 (m, 2H), 3.77 (m, 1H), 3.41 (m, 1H), 2.80 (s, 3H).

Step G: Preparation of N-(2-fluorophenyl)-4-(3-formylphenyl)-1-methyl-2-oxo-3-pyrrolidinecarboxamide To a solution of N-(2-fluorophenyl)-4-(3-iodophenyl)-1-methyl-2-oxo-3-pyrrolidinecarboxamide (i.e. the compound prepared in Step F, 0.5 g, 1.1 mmol) and tetrakis(triphenylphosphine)palladium(0) (0.086 g, 0.075 mmol) in N,N-dimethylformamide (5 mL) in steel bomb was stirred under carbon monoxide gas (100 p.s.i.) for 30 min. the pressure was released and tributyl silane (0.83 mL) was added and the reaction mixture was stirred under carbon monoxide gas (100 p.s.i.) at ambient temperature for 48 h. The reaction mixture was then diluted with water and extracted with ethyl acetate. The combined organic layers were washed with water and brine and dried over sodium sulfate. The solvent was evaporated to give the crude residue which was purified via silica gel column chromatography eluting with 20% ethyl acetate in petroleum ether to yield the title compound (0.27 g) as light brown solid.

$^1$H NMR (400 MHz) δ 10.15 (s, 1H), 10.00 (s, 1H), 8.15 (t, 1H), 7.82 (m, 1H), 7.64 (m, 1H), 7.55 (m, 1H), 7.39 (m, 1H), 7.12 (m, 3H), 4.20 (m, 1H), 3.80 (t, 1H), 3.31 (d, 1H), 3.22 (m, 1H), 3.10 (s, 3H).

Step H: Preparation of N-(2-fluorophenyl)-4-[3-[(methoxyimino)methyl]phenyl]-1-methyl-2-oxo-3-pyrrolidinecarboxamide To a solution of N-(2-fluorophenyl)-4-(3-formylphenyl)-1-methyl-2-oxo-3-pyrrolidinecarboxamide (i.e. the compound prepared in Step G, 0.15 g, 0.41 mmol) and methoxylamine hydrochloride (0.054 g, 0.64 mmol) in tetrahydrofuran (10 mL) was added sodium acetate (0.047 g, 0.57 mmol) and stirred at ambient temperature for 2 h. The reaction mixture was then diluted with water and extracted with ethyl acetate. The combined organic layers were washed with water and brine and dried over sodium sulfate. The solvent was evaporated to give the crude product which was purified by preparative silica gel thin-layer chromatography in 40% ethyl acetate/petroleum ether to yield (0.07 g) of the title compound, a compound of the present invention, as an off-white solid.

$^1$H NMR (400 MHz) δ 9.85 (s, 1H), 8.25 (t, 1H), 8.10 (s, 1H), 7.55 (s, 1H), 7.45 (s, 1H), 7.25 (s, 2H), 6.99 (m, 3H), 4.25 (m, 1H), 4.10 (s, 3H), 3.75 (d, 1H), 3.50 (m, 1H), 3.33 (m, 1H), 3.00 (s, 3H).

Synthesis Example 4

Preparation of (3S,4S)-4-[3-[(5-fluoro-2-pyridinyl) oxy]phenyl]-1-methyl-2-oxo-N-(2,3,4-trifluorophenyl)-3-pyrrolidinecarboxamide (Compound 87)

Step A. Preparation of 3-[(5-fluoro-2-pyridinyl)oxy] benzaldehyde

A solution 3-hydroxybenzaldehyde (20 g, 164 mmol) in N,N-dimethylformamide (150 mL) was treated with potassium tert-butoxide (23.0 g, 205 mmol) over a period of 1 h. The resulting mixture was stirred at 25° C. for 1 h and then treated with 2,5-difluoropyridine (18.64 g, 162 mmol). The resulting reaction mixture was stirred at 120° C. for 18 h. The reaction mixture was then cooled and partitioned between ethyl acetate and brine. The organic phase was washed with brine, dried over MgSO$_4$ and concentrated under reduced pressure onto Celite® diatomaceous earth filter aid. Purification by solid chromatography eluting with a gradient of ethyl acetate in hexanes (0 to 35%) provided 10.0 g of the title compound a white solid.

$^1$H NMR (DMSO-d6) δ 10.00 (s, 1H), 8.18 (d, 1H), 7.88 (m, 1H), 7.78 (m, 1H), 7.66 (t, 1H), 7.62 (m, 1H), 7.50 (m, 1H), 7.23 (m, 1H).

Step B: Preparation of 5-fluoro-2-[3-[(1E)-2-nitroethenyl]phenoxy]pyridine

A solution of 3-[(5-fluoro-2-pyridinyl)oxy]benzaldehyde (i.e. the product obtained in Step A, 10 g, 46.0 mmol) in 1-chlorobutane (250 mL) was treated with nitromethane (3.36 g, 55.2 mmol) followed by piperidine (391 mg, 4.6 mmol) and acetic acid (276 mg, 4.6 mmol). The resulting reaction mass was stirred at reflux, with azeotropic removal of water, for 18 h. The crude reaction mixture was then concentrated under reduced pressure and purified by chromatography (0 to 25% ethyl acetate in hexanes as eluent) resulting in 8.7 g of a yellow oil.

$^1$H NMR δ 8.02 (d, 1H), 7.98 (d, 1H), 7.55 (d, 1H), 7.49 (m, 2H), 7.38 (d, 1H), 7.31 (m, 1H), 7.26 (m, 1H), 6.98 (m, 1H).

Step C: Preparation of 1,3-dimethyl 2-[(1S)-1-[3-[(5-fluoro-2-pyridinyl)oxy]phenyl]-2-nitroethyl] propanedioate A stirred mixture of 5-fluoro-2-[3-[(1E)-2-nitroethenyl] phenoxy]pyridine (i.e. the product obtained in Step B, 8.67 g, 33.3 mmol) and dimethyl malonate (5.5 g, 41.7 mmol) in toluene (150 mL) was treated with Ni(II) bis[(R,R)—N,N'-dibenzylcyclohexane-1,2-diamine]bromide (prepared as described in *J. Am. Chem. Soc.* 2005, 127, 9958-9959; 0.400 g, 0.499 mmol). The reaction mass was stirred at 80° C. for 18 h. The resulting mixture was cooled to 25° C., filtered and concentrated under reduced pressure to yield 13.0 g of an amber oil which was used without further purification in the next step.

$^1$H NMR δ 8.05 (d, 1H), 7.45 (m, 1H), 7.35 (t, 1H), 7.06 (m, 2H), 6.99 (m, 1H), 6.87 (m, 1H), 4.90 (m, 2H), 4.25 (m, 1H), 3.85 (d, 1H), 3.75 (s, 3H), 3.62 (s, 3H).

Step D: Preparation of methyl (3R,4S)-4-[3-[(5-fluoro-2-pyridinyl)oxy]phenyl]-2-oxo-3-pyrrolidinecarboxylate A stirred mixture of 1,3-dimethyl 2-[(1S)-1-[3-[(5-fluoro-2-pyridinyl)oxy]phenyl]-2-nitroethyl]propanedioate (13.0 g, 33.1 mmol), nickel(II) chloride hexahydrate (7.88 g, 33.1 mmol) and methanol (300 mL) was cooled in an ice bath and treated with sodium borohydride (i.e. the product obtained in Step C, 3.76 g, 99.3 mmol) in 0.5 g portions added over 60 min. The resulting mixture was stirred at 25° C. for 18 h. Saturated ethylenediaminetetraacetic acid, disodium salt solution (800 mL) and ethyl acetate (500 mL) were then added and the mixture was stirred for 18 h and then filtered through a pad of Celite® diatomaceous filter aid to remove insoluble particulates. The layers of the filtrate were separated, and the aqueous layer was extracted with ethyl acetate (2×500 mL). The combined organic extracts were washed with saturated ammonium chloride solution (800 mL), and brine (1000 mL). The organic extract was dried over MgSO$_4$ and concentrated under reduced pressure to afford a viscous grey oil (8.99 g) which was used without further purification.

$^1$H NMR δ 8.02 (d, 1H), 7.45 (m, 1H), 7.37 (t, 1H), 7.09 (m, 1H), 7.02 (m, 2H), 6.94 (m, 2H), 4.13 (m, 1H), 3.82 (m, 1H), 3.78 (s, 3H), 3.58 (d, 1H), 3.42 (m, 1H).

Step E: Preparation of (3R,4S)-4-[3-[(5-fluoro-2-pyridinyl)oxy]phenyl]-2-oxo-3-pyrrolidinecarboxylic acid A mixture of methyl (3R,4S)-4-[3-[(5-fluoro-2-pyridinyl) oxy]phenyl]-2-oxo-3-pyrrolidinecarboxylate (i.e. the product obtained in Step D, 8.49 g, 25.7 mmol) and aqueous sodium hydroxide (50 wt %, 6.16 g, 77.2 mmol) in methanol (125 mL) was stirred at 25° C. for 18 h. The reaction mixture was then diluted with water (250 mL) and extracted with diethyl ether (2×150 mL). The ether extract was discarded and the aqueous phase was acidified with concentrated hydrochloric acid to pH 2. The acidic aqueous was extracted with ethyl acetate (2×300 mL). The combined organic extracts were washed with brine, dried (MgSO$_4$), and concentrated under reduced pressure to afford 5.5 g of a beige glass which was carried to the next step without further purification.

$^1$H NMR (DMSO-d$_6$) δ 12.7 (s, 1H), 8.16 (d, 1H), 8.07 (s, 1H), 7.83 (m, 1H), 7.37 (m, 1H), 7.17 (m, 1H), 7.12 (m, 2H), 7.01 (m, 1H), 3.88 (m, 1H), 3.62 (m, 1H), 3.51 (d, 1H), 3.21 (t, 1H).

Step F: Preparation of (3R,4S)-4-[3-[(5-fluoro-2-pyridinyl)oxy]phenyl]-1-methyl-2-oxo-3-pyrrolidinecarboxylic acid To a solution of potassium tert-butoxide (4.75 g, 42.4 mmol) in 42.4 mL of tetrahydrofuran at 0° C. was charged a solution of (3R,4S)-4-[3-[(5-fluoro-2-pyridinyl)oxy]phenyl]-2-oxo-3-pyrrolidinecarboxylic acid (i.e. the product obtained in Step E, 5.5 g, 17.4 mmol) in tetrahydrofuran (50 mL). The resulting reaction mass was stirred for 15 min. at 0° C. Iodomethane (6.24 g, 44 mmol) in 40 mL of tetrahydrofuran was dripped in over 20 min. The resulting mixture was allowed to warm to 25° C. and stirred over night. The reaction mass was concentrated under reduced pressure and partitioned between ethyl ether and water. The organic phase was discarded and the aqueous was acidified to a pH of 1 with concentrated hydrochloric acid. The acidified aqueous layer was extracted with ethyl acetate. The organic extract was dried (MgSO$_4$) and concentrated under reduced pressure to yield 4.0 g of a yellow glass which was carried on without further purification.

$^1$H NMR δ 9.29 (s, 1H), 8.03 (d, 1H), 7.46 (m, 1H), 7.37 (m, 1H), 7.13 (m, 1H), 7.06 (m, 1H), 7.02 (m, 1H), 6.92 (m, 1H), 3.96 (m, 1H), 3.79 (m, 1H), 3.57 (d, 1H), 3.50 (m, 1H), 2.97 (d, 3H).

Step G: Preparation of (3S,4S)-4-[3-[(5-fluoro-2-pyridinyl)oxy]phenyl]-1-methyl-2-oxo-N-(2,3,4-trifluorophenyl)-3-pyrrolidinecarboxamide To a solution of (3R,4S)-4-[3-[(5-fluoro-2-pyridinyl)oxy]phenyl]-1-methyl-2-oxo-3-pyrrolidinecarboxylic acid (i.e. the product obtained in Step F, 500 mg, 1.51 mmol) in 5.0 mL of tetrahydrofuran at 25° C. was charged triethylamine (632 µl, 4.54 mmol). The reaction mixture was stirred for 5 min. and then treated with 2,3,4-trifluoroaniline (208 µl, 1.97 mmol). After stirring for another 5 min. the mixture was treated with propylphosphonic anhydride (50% in ethyl acetate, 1.63 g, 2.57 mmol). The resulting mixture was stirred overnight at 25° C. The crude mixture was concentrated under reduced pressure and purified by silica gel chromatography eluting with 0 to 15% ethyl acetate in dichloromethane resulting in 278 mg of the title compound, a compound of the invention, as a viscous yellow oil.

$^1$H NMR δ 9.86 (s, 1H), 8.02 (d, 1H), 7.93 (m, 1H), 7.45 (m, 1H), 7.39 (t, 1H), 7.19 (m, 1H), 7.12 (m, 1H), 7.03 (m, 1H), 6.93 (m, 1H), 6.90 (m, 1H), 4.11 (m, 1H), 3.80 (m, 1H), 3.62 (d, 1H), 3.50 (m, 1H), 2.99 (d, 3H).

By the procedures described herein together with methods known in the art, the following compounds of Tables 1 to 6120 can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, c-Pr cyclopropyl, t-Bu means tertiary butyl, c-Bu means cyclobutyl, Ph means phenyl, OMe means methoxy, OEt means ethoxy, SMe means methylthio, NHMe means methylamino, CN means cyano, NO$_2$ means nitro, TMS means trimethylsilyl, SOMe means methylsulfinyl, C$_2$F$_5$ means CF$_2$CF$_3$ and SO$_2$Me means methyl sulfonyl.

TABLE 1

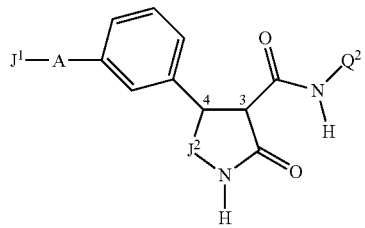

J$^2$ is —CH$_2$—; A is —CH$_2$—; Q$^2$ is Ph(2-F); and J$^1$ is

| J$^1$ |
|---|
| Ph(3-Cl) |
| Ph(3-F) |
| Ph(3-Br) |
| Ph(3-Me) |
| Ph(3-CF$_3$) |
| Ph(3-OCF$_3$) |
| Ph(3-OCF$_2$H) |
| Ph(3-OMe) |
| Ph(3-OCF$_2$CF$_2$H) |
| Ph(2-Cl) |
| Ph(2-F) |
| Ph(2-Br) |
| Ph(2-Me) |
| Ph(2-CF$_3$) |
| Ph(2-OCF$_3$) |
| Ph(2-OCF$_2$H) |
| Ph(2-OMe) |
| Ph(2-OCF$_2$CF$_2$H) |
| Ph(4-Cl) |
| Ph(4-F) |
| Ph(4-Br) |
| Ph(4-Me) |
| Ph(4-CF$_3$) |
| Ph(4-OCF$_3$) |
| 4-Pyridinyl(3-F) |
| 4-Pyridinyl(3-CF$_3$) |
| 4-Pyridinyl(3-Me) |
| 4-Pyridinyl(2-F) |
| 4-Pyridinyl(2-CF$_3$) |
| 4-Pyridinyl(2-Me) |
| 2-Thienyl |
| 2-Thienyl(4-CF$_3$) |
| 2-Thienyl(5-CF$_3$) |
| 3-Thienyl |
| 3-Thienyl(4-CF$_3$) |
| 3-Thienyl(5-CF$_3$) |
| 2-Furanyl |
| 2-Furanyl(4-CF$_3$) |
| 2-Furanyl(5-CF$_3$) |
| 3-Furanyl |
| 3-Furanyl(4-CF$_3$) |
| 3-Furanyl(5-CF$_3$) |
| Pyrazol-1-yl |
| Pyrazol-1-yl(4-CF$_3$) |
| Imidazol-1-yl |
| Imidazol-1-yl(4-CF$_3$) |
| Imidazol-1-yl(2-CF$_3$) |
| Imidazol-2-yl(1-Me) |
| Imidazol-4-yl(1-Me) |
| Imidazol-4-yl(2-Me) |
| Pyrazol-4-yl(1-Me) |
| Triazol-4-yl(1-Me) |
| Triazol-4-yl(2-Me) |
| Triazol-2-yl(4-Me) |
| Triazol-1-yl(4-Me) |
| Pyrazin-2-yl |
| Pyrazin-2-yl(5-CF$_3$) |
| Pyrimidin-2-yl |
| Pyrimidin-2-yl(5-CF$_3$) |
| Pyrimidin-5-yl |
| Pyrimidin-5-yl(2-CF$_3$) |
| 3-fluoroprop-2-ynyl |
| 3-chloroprop-2-ynyl |
| 5-propoxypentyl |

TABLE 1-continued

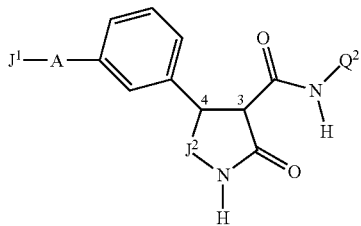

J² is —CH₂—; A is —CH₂—; Q² is Ph(2-F); and J¹ is

J¹

2-ethoxyethyl
5-(1,1,2,2-tetrafluoroethoxy)pentyl
2-(1,1,2,2-tetrafluoroethoxy)ethyl
5-(trifloromethoxy)pentyl
Ph(4-OCF₂H)
Ph(4-OMe)
Ph(4-OCF₂CF₂H)
Ph(2,3-di-F)
Ph(2,4-di-F)
Ph(2,5-di-F)
Ph(2,6-di-F)
Ph(3,4-di-F)
Ph(3,5-di-F)
Ph(3-Me,4-F)
Ph(3-F,4-Me)
Ph(3-CF₃,4-F)
Ph(3-F,4-CF₃)
Ph(2,3,4-tri-F)
Ph(3,4,5-tri-F)
2-Pyridinyl
2-Pyridinyl(6-F)
2-Pyridinyl(6-CF₃)
2-Pyridinyl(6-Me)
2-Pyridinyl(5-F)
2-Pyridinyl(5-CF₃)
2-Pyridinyl(5-Me)
2-Pyridinyl(4-F)
2-Pyridinyl(4-CF₃)
1,3,5-Triazin-2-yl
Thiazol-2-yl
Thiazol-2-yl(5-CF₃)
Thiazol-5-yl
Thiazol-5-yl(2-CF₃)
Oxazol-2-yl
Oxazol-2-yl(5-CF₃)
Oxazol-5-yl
Oxazol-5-yl(2-CF₃)
Isothiazol-5-yl
Isothiazol-5-yl(3-CF₃)
Isothiazol-3-yl
Isothiazol-3-yl(5-CF₃)
Isoxazol-5-yl
Isoxazol-5-yl(3-CF₃)
Isoxazol-3-yl
Isoxazol-3-yl(5-CF₃)
Tetrazol-1-yl
Tetrazol-1-yl(5-Me)
Tetrazol-5-yl(1-Me)
1,2,4-Triazol-1-yl
1,3,4-Oxadiazol-2-yl
1,3,4-Thiadiazol-2-yl
1,2,4-Oxadiazol-3-yl
1,2,4-Thiadiazol-3-yl
Tetrahydropyran-2-yl
Tetrahydropyran-3-yl
Tetrahydrofuran-2-yl
Tetrahydrofuran-3-yl
Oxetan-2-yl
Oxetan-3-yl
Oxiran-2-yl
1,3-Dioxolan-4-yl
2,2-difluoro-1,3-Dioxolan-4-yl
1,3-Dithiolan-4-yl
1,4-Dioxolan-2-yl TABLE 1-continued

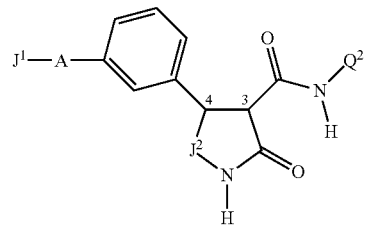

J² is —CH₂—; A is —CH₂—; Q² is Ph(2-F); and J¹ is

J¹

1,4-Dithiolan-2-yl
2-(trifluoromethoxy)ethyl
4-(1,1,2,2,-tetrafluoroethoxy)butoxy
2-(1,1,2,2,-tetrafluoroethoxy)ethoxy
4-(trifluoromethoxy)butoxy
2(trifluoromethoxy)ethoxy
Trifluoromethyl
3,3,3-trifluoropropyl
2-Pyridinyl(4-Me)
2-Pyridinyl(3-F)
2-Pyridinyl(3-CF₃)
2-Pyridinyl(3-Me)
3-Pyridinyl
3-Pyridinyl(6-F)
3-Pyridinyl(6-CF₃)
3-Pyridinyl(6-Me)
3-Pyridinyl(5-F)
3-Pyridinyl(5-CF₃)
3-Pyridinyl(5-Me)
3-Pyridinyl(4-F)
3-Pyridinyl(4-CF₃)
3-Pyridinyl(4-Me)
3-Pyridinyl(2-F)
3-Pyridinyl(2-CF₃)
3-Pyridinyl(2-Me)
4-Pyridinyl
4-Pyridinyl(6-F)
4-Pyridinyl(6-CF₃)
4-Pyridinyl(6-Me)
4-Pyridinyl(5-F)
4-Pyridinyl(5-CF₃)
4-Pyridinyl(5-Me)
1-naphthyl
2-naphthyl
Benzofuran-2-yl
Benzothiophen-2-yl
1,3-Benzoxazol-2-yl
1,3-Benzthiazol-2-yl
7-quinolyl
Indazol-1-yl
Benzimidazol-1-yl
Indol-1-yl
Pyrrolo[2,3-c]pyridin-1-yl
Cyclopropylmethoxy
2-cyclopropylethoxy
4-cyclohexylbutoxy
Cyclopropylmethyl
4-cyclohexylbutyl
Oct-7-enoxy
[(E)-but-2-enoxy]
2,2-difluorovinyloxy
3,3-dichloroallyloxy
2-methoxyethoxy
3-propoxypropoxy
2-methylthioethyl
2-methylsulfinylethyl
2-methylsulfonylethyl
2-CF₃SO₂CH₂CH₂O
Methylsulfanyl
Trifluoromethylthio
Cyclopropylthio
Methylsulfinyl
Trifluoromethylsulfinyl
Cyclopropylsulfinyl

TABLE 1-continued

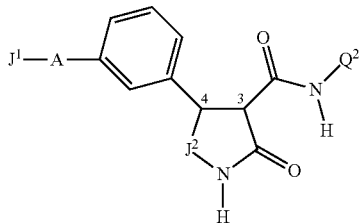

$J^2$ is —$CH_2$—; A is —$CH_2$—; $Q^2$ is Ph(2-F); and $J^1$ is

| $J^1$ |
|---|
| Methylsulfonyl |
| Trifluoromethylsulfonyl |
| Cyclopropylsulfonyl |
| Prop-2-ynyl |
| But-2-ynyl |
| 2-fluorocyclopropyl |
| 4,4-difluorocyclohexyl |
| Acetoxy |
| 2,2-dimethylpropanoyloxy |

TABLE 1-continued

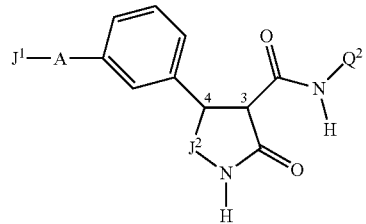

$J^2$ is —$CH_2$—; A is —$CH_2$—; $Q^2$ is Ph(2-F); and $J^1$ is

| $J^1$ |
|---|
| 3-methylbutanoyloxy |
| 2,2,2-trifluoroacetyloxy |
| 4,4,4-trifluorobutanoyloxy |

Table 2-360

Table 2 is constructed in the same manner except that the Row heading "$J^2$ is —$CH_2$—; A is —$CH_2$—; $Q^2$ is Ph(2-F); and $J^1$ is" is replaced with the Row Heading listed for Table 2 below (i.e. "$J^2$ is —$CH_2$—; A is —$CH_2$—; $Q^2$ is Ph(2,3-di-F); and $J^1$ is"). Therefore the first entry in Table 2 is a compound of Formula 1 wherein $J^2$ is —$CH_2$—; A is —$CH_2$—; $Q^2$ is Ph(2,3-di-F); and $J^1$ is Ph(3-Cl) (i.e. 3-chlorophenyl). Tables 3 through 360 are constructed similarly.

| Table | Row Heading |
|---|---|
| 2 | $J^2$ is —$CH_2$—; A is —$CH_2$—; $Q^2$ is Ph(2,3-di-F); and $J^1$ is |
| 3 | $J^2$ is —$CH_2$—; A is —$CH_2$—; $Q^2$ is Ph(2,4-di-F); and $J^1$ is |
| 4 | $J^2$ is —$CH_2$—; A is —$CH_2$—; $Q^2$ is Ph(2,3,4-tri-F); and $J^1$ is |
| 5 | $J^2$ is —$CH_2$—; A is —$CH_2$—; $Q^2$ is Ph(2-$CF_3$); and $J^1$ is |
| 6 | $J^2$ is —$CH_2$—; A is —$CH_2$—; $Q^2$ is Ph(2-Me); and $J^1$ is |
| 7 | $J^2$ is —$CH_2$—; A is —$CH_2$—; $Q^2$ is Ph(2-$NO_2$); and $J^1$ is |
| 8 | $J^2$ is —$CH_2$—; A is —$CH_2$—; $Q^2$ is Ph(2-Cl); and $J^1$ is |
| 9 | $J^2$ is —$CH_2$—; A is —$CH_2$—; $Q^2$ is Ph(2-$SO_2$Me); and $J^1$ is |
| 10 | $J^2$ is —$CH_2$—; A is —$CH_2$—; $Q^2$ is Ph(2-F,3-Cl); and $J^1$ is |
| 11 | $J^2$ is —$CH_2$—; A is —$CH_2CH_2$—; $Q^2$ is Ph(2-F); and $J^1$ is |
| 12 | $J^2$ is —$CH_2$—; A is —$CH_2CH_2$—; $Q^2$ is Ph(2,3-di-F); and $J^1$ is |
| 13 | $J^2$ is —$CH_2$—; A is —$CH_2CH_2$—; $Q^2$ is Ph(2,4-di-F); and $J^1$ is |
| 14 | $J^2$ is —$CH_2$—; A is —$CH_2CH_2$—; $Q^2$ is Ph(2,3,4-tri-F); and $J^1$ is |
| 15 | $J^2$ is —$CH_2$—; A is —$CH_2CH_2$—; $Q^2$ is Ph(2-$CF_3$); and $J^1$ is |
| 16 | $J^2$ is —$CH_2$—; A is —$CH_2CH_2$—; $Q^2$ is Ph(2-Me); and $J^1$ is |
| 17 | $J^2$ is —$CH_2$—; A is —$CH_2CH_2$—; $Q^2$ is Ph(2-$NO_2$); and $J^1$ is |
| 18 | $J^2$ is —$CH_2$—; A is —$CH_2CH_2$—; $Q^2$ is Ph(2-Cl); and $J^1$ is |
| 19 | $J^2$ is —$CH_2$—; A is —$CH_2CH_2$—; $Q^2$ is Ph(2-$SO_2$Me); and $J^1$ is |
| 20 | $J^2$ is —$CH_2$—; A is —$CH_2CH_2$—; $Q^2$ is Ph(2-F,3-Cl); and $J^1$ is |
| 21 | $J^2$ is —$CH_2$—; A is —$CH_2CH_2CH_2$—; $Q^2$ is Ph(2-F); and $J^1$ is |
| 22 | $J^2$ is —$CH_2$—; A is —$CH_2CH_2CH_2$—; $Q^2$ is Ph(2,3-di-F); and $J^1$ is |
| 23 | $J^2$ is —$CH_2$—; A is —$CH_2CH_2CH_2$—; $Q^2$ is Ph(2,4-di-F); and $J^1$ is |
| 24 | $J^2$ is —$CH_2$—; A is —$CH_2CH_2CH_2$—; $Q^2$ is Ph(2,3,4-tri-F); and $J^1$ is |
| 25 | $J^2$ is —$CH_2$—; A is —$CH_2CH_2CH_2$—; $Q^2$ is Ph(2-$CF_3$); and $J^1$ is |
| 26 | $J^2$ is —$CH_2$—; A is —$CH_2CH_2CH_2$—; $Q^2$ is Ph(2-Me); and $J^1$ is |
| 27 | $J^2$ is —$CH_2$—; A is —$CH_2CH_2CH_2$—; $Q^2$ is Ph(2-$NO_2$); and $J^1$ is |
| 28 | $J^2$ is —$CH_2$—; A is —$CH_2CH_2CH_2$—; $Q^2$ is Ph(2-Cl); and $J^1$ is |
| 29 | $J^2$ is —$CH_2$—; A is —$CH_2CH_2CH_2$—; $Q^2$ is Ph(2-$SO_2$Me); and $J^1$ is |
| 30 | $J^2$ is —$CH_2$—; A is —$CH_2CH_2CH_2$—; $Q^2$ is Ph(2-F,3-Cl); and $J^1$ is |
| 31 | $J^2$ is —$CH_2$—; A is —O—; $Q^2$ is Ph(2-F); and $J^1$ is |
| 32 | $J^2$ is —$CH_2$—; A is —O—; $Q^2$ is Ph(2,3-di-F); and $J^1$ is |
| 33 | $J^2$ is —$CH_2$—; A is —O—; $Q^2$ is Ph(2,4-di-F); and $J^1$ is |
| 34 | $J^2$ is —$CH_2$—; A is —O—; $Q^2$ is Ph(2,3,4-tri-F); and $J^1$ is |
| 35 | $J^2$ is —$CH_2$—; A is —O—; $Q^2$ is Ph(2-$CF_3$); and $J^1$ is |
| 36 | $J^2$ is —$CH_2$—; A is —O—; $Q^2$ is Ph(2-Me); and $J^1$ is |
| 37 | $J^2$ is —$CH_2$—; A is —O—; $Q^2$ is Ph(2-$NO_2$); and $J^1$ is |
| 38 | $J^2$ is —$CH_2$—; A is —O—; $Q^2$ is Ph(2-Cl); and $J^1$ is |
| 39 | $J^2$ is —$CH_2$—; A is —O—; $Q^2$ is Ph(2-$SO_2$Me); and $J^1$ is |
| 40 | $J^2$ is —$CH_2$—; A is —O—; $Q^2$ is Ph(2-F,3-Cl); and $J^1$ is |
| 41 | $J^2$ is —$CH_2$—; A is —$OCH_2$—; $Q^2$ is Ph(2-F); and $J^1$ is |
| 42 | $J^2$ is —$CH_2$—; A is —$OCH_2$—; $Q^2$ is Ph(2,3-di-F); and $J^1$ is |
| 43 | $J^2$ is —$CH_2$—; A is —$OCH_2$—; $Q^2$ is Ph(2,4-di-F); and $J^1$ is |
| 44 | $J^2$ is —$CH_2$—; A is —$OCH_2$—; $Q^2$ is Ph(2,3,4-tri-F); and $J^1$ is |

| Table | Row Heading |
|---|---|
| 45 | J² is —CH₂—; A is —OCH₂—; Q² is Ph(2-CF₃); and J¹ is |
| 46 | J² is —CH₂—; A is —OCH₂—; Q² is Ph(2-Me); and J¹ is |
| 47 | J² is —CH₂—; A is —OCH₂—; Q² is Ph(2-NO₂); and J¹ is |
| 48 | J² is —CH₂—; A is —OCH₂—; Q² is Ph(2-Cl); and J¹ is |
| 49 | J² is —CH₂—; A is —OCH₂—; Q² is Ph(2-SO₂Me); and J¹ is |
| 50 | J² is —CH₂—; A is —OCH₂—; Q² is Ph(2-F,3-Cl); and J¹ is |
| 51 | J² is —CH₂—; A is —OCH₂CH₂—; Q² is Ph(2-F); and J¹ is |
| 52 | J² is —CH₂—; A is —OCH₂CH₂—; Q² is Ph(2,3-di-F); and J¹ is |
| 53 | J² is —CH₂—; A is —OCH₂CH₂—; Q² is Ph(2,4-di-F); and J¹ is |
| 54 | J² is —CH₂—; A is —OCH₂CH₂—; Q² is Ph(2,3,4-tri-F); and J¹ is |
| 55 | J² is —CH₂—; A is —OCH₂CH₂—; Q² is Ph(2-CF₃); and J¹ is |
| 56 | J² is —CH₂—; A is —OCH₂CH₂—; Q² is Ph(2-Me); and J¹ is |
| 57 | J² is —CH₂—; A is —OCH₂CH₂—; Q² is Ph(2-NO₂); and J¹ is |
| 58 | J² is —CH₂—; A is —OCH₂CH₂—; Q² is Ph(2-Cl); and J¹ is |
| 59 | J² is —CH₂—; A is —OCH₂CH₂—; Q² is Ph(2-SO₂Me); and J¹ is |
| 60 | J² is —CH₂—; A is —OCH₂CH₂—; Q² is Ph(2-F,3-Cl); and J¹ is |
| 61 | J² is —CH₂—; A is —CH₂O—; Q² is Ph(2-F); and J¹ is |
| 62 | J² is —CH₂—; A is —CH₂O—; Q² is Ph(2,3-di-F); and J¹ is |
| 63 | J² is —CH₂—; A is —CH₂O—; Q² is Ph(2,4-di-F); and J¹ is |
| 64 | J² is —CH₂—; A is —CH₂O—; Q² is Ph(2,3,4-tri-F); and J¹ is |
| 65 | J² is —CH₂—; A is —CH₂O—; Q² is Ph(2-CF₃); and J¹ is |
| 66 | J² is —CH₂—; A is —CH₂O—; Q² is Ph(2-Me); and J¹ is |
| 67 | J² is —CH₂—; A is —CH₂O—; Q² is Ph(2-NO₂); and J¹ is |
| 68 | J² is —CH₂—; A is —CH₂O—; Q² is Ph(2-Cl); and J¹ is |
| 69 | J² is —CH₂—; A is —CH₂O—; Q² is Ph(2-SO₂Me); and J¹ is |
| 70 | J² is —CH₂—; A is —CH₂O—; Q² is Ph(2-F,3-Cl); and J¹ is |
| 71 | J² is —CH₂—; A is —CH₂CH₂O—; Q² is Ph(2-F); and J¹ is |
| 72 | J² is —CH₂—; A is —CH₂CH₂O—; Q² is Ph(2,3-di-F); and J¹ is |
| 73 | J² is —CH₂—; A is —CH₂CH₂O—; Q² is Ph(2,4-di-F); and J¹ is |
| 74 | J² is —CH₂—; A is —CH₂CH₂O—; Q² is Ph(2,3,4-tri-F); and J¹ is |
| 75 | J² is —CH₂—; A is —CH₂CH₂O—; Q² is Ph(2-CF₃); and J¹ is |
| 76 | J² is —CH₂—; A is —CH₂CH₂O—; Q² is Ph(2-Me); and J¹ is |
| 77 | J² is —CH₂—; A is —CH₂CH₂O—; Q² is Ph(2-NO₂); and J¹ is |
| 78 | J² is —CH₂—; A is —CH₂CH₂O—; Q² is Ph(2-Cl); and J¹ is |
| 79 | J² is —CH₂—; A is —CH₂CH₂O—; Q² is Ph(2-SO₂Me); and J¹ is |
| 80 | J² is —CH₂—; A is —CH₂CH₂O—; Q² is Ph(2-F,3-Cl); and J¹ is |
| 81 | J² is —CH₂—; A is —S—; Q² is Ph(2-F); and J¹ is |
| 82 | J² is —CH₂—; A is —S—; Q² is Ph(2,3-di-F); and J¹ is |
| 83 | J² is —CH₂—; A is —S—; Q² is Ph(2,4-di-F); and J¹ is |
| 84 | J² is —CH₂—; A is —S—; Q² is Ph(2,3,4-tri-F); and J¹ is |
| 85 | J² is —CH₂—; A is —S—; Q² is Ph(2-CF₃); and J¹ is |
| 86 | J² is —CH₂—; A is —S—; Q² is Ph(2-Me); and J¹ is |
| 87 | J² is —CH₂—; A is —S—; Q² is Ph(2-NO₂); and J¹ is |
| 88 | J² is —CH₂—; A is —S—; Q² is Ph(2-Cl); and J¹ is |
| 89 | J² is —CH₂—; A is —S—; Q² is Ph(2-SO₂Me); and J¹ is |
| 90 | J² is —CH₂—; A is —S—; Q² is Ph(2-F,3-Cl); and J¹ is |
| 91 | J² is —CH₂—; A is —SCH₂—; Q² is Ph(2-F); and J¹ is |
| 92 | J² is —CH₂—; A is —SCH₂—; Q² is Ph(2,3-di-F); and J¹ is |
| 93 | J² is —CH₂—; A is —SCH₂—; Q² is Ph(2,4-di-F); and J¹ is |
| 94 | J² is —CH₂—; A is —SCH₂—; Q² is Ph(2,3,4-tri-F); and J¹ is |
| 95 | J² is —CH₂—; A is —SCH₂—; Q² is Ph(2-CF₃); and J¹ is |
| 96 | J² is —CH₂—; A is —SCH₂—; Q² is Ph(2-Me); and J¹ is |
| 97 | J² is —CH₂—; A is —SCH₂—; Q² is Ph(2-NO₂); and J¹ is |
| 98 | J² is —CH₂—; A is —SCH₂—; Q² is Ph(2-Cl); and J¹ is |
| 99 | J² is —CH₂—; A is —SCH₂—; Q² is Ph(2-SO₂Me); and J¹ is |
| 100 | J² is —CH₂—; A is —SCH₂—; Q² is Ph(2-F,3-Cl); and J¹ is |
| 101 | J² is —CH₂—; A is —CH₂S—; Q² is Ph(2-F); and J¹ is |
| 102 | J² is —CH₂—; A is —CH₂S—; Q² is Ph(2,3-di-F); and J¹ is |
| 103 | J² is —CH₂—; A is —CH₂S—; Q² is Ph(2,4-di-F); and J¹ is |
| 104 | J² is —CH₂—; A is —CH₂S—; Q² is Ph(2,3,4-tri-F); and J¹ is |
| 105 | J² is —CH₂—; A is —CH₂S—; Q² is Ph(2-CF₃); and J¹ is |
| 106 | J² is —CH₂—; A is —CH₂S—; Q² is Ph(2-Me); and J¹ is |
| 107 | J² is —CH₂—; A is —CH₂S—; Q² is Ph(2-NO₂); and J¹ is |
| 108 | J² is —CH₂—; A is —CH₂S—; Q² is Ph(2-Cl); and J¹ is |
| 109 | J² is —CH₂—; A is —CH₂S—; Q² is Ph(2-SO₂Me); and J¹ is |
| 110 | J² is —CH₂—; A is —CH₂S—; Q² is Ph(2-F,3-Cl); and J¹ is |
| 111 | J² is —CH₂—; A is —NH—; Q² is Ph(2-F); and J¹ is |
| 112 | J² is —CH₂—; A is —NH—; Q² is Ph(2,3-di-F); and J¹ is |
| 113 | J² is —CH₂—; A is —NH—; Q² is Ph(2,4-di-F); and J¹ is |
| 114 | J² is —CH₂—; A is —NH—; Q² is Ph(2,3,4-tri-F); and J¹ is |
| 115 | J² is —CH₂—; A is —NH—; Q² is Ph(2-CF₃); and J¹ is |
| 116 | J² is —CH₂—; A is —NH—; Q² is Ph(2-Me); and J¹ is |
| 117 | J² is —CH₂—; A is —NH—; Q² is Ph(2-NO₂); and J¹ is |
| 118 | J² is —CH₂—; A is —NH—; Q² is Ph(2-Cl); and J¹ is |
| 119 | J² is —CH₂—; A is —NH—; Q² is Ph(2-SO₂Me); and J¹ is |
| 120 | J² is —CH₂—; A is —NH—; Q² is Ph(2-F,3-Cl); and J¹ is |
| 121 | J² is —CH₂—; A is —CH₂NH—; Q² is Ph(2-F); and J¹ is |

| Table | Row Heading |
|---|---|
| 122 | $J^2$ is —$CH_2$—; A is —$CH_2NH$—; $Q^2$ is Ph(2,3-di-F); and $J^1$ is |
| 123 | $J^2$ is —$CH_2$—; A is —$CH_2NH$—; $Q^2$ is Ph(2,4-di-F); and $J^1$ is |
| 124 | $J^2$ is —$CH_2$—; A is —$CH_2NH$—; $Q^2$ is Ph(2,3,4-tri-F); and $J^1$ is |
| 125 | $J^2$ is —$CH_2$—; A is —$CH_2NH$—; $Q^2$ is Ph(2-$CF_3$); and $J^1$ is |
| 126 | $J^2$ is —$CH_2$—; A is —$CH_2NH$—; $Q^2$ is Ph(2-Me); and $J^1$ is |
| 127 | $J^2$ is —$CH_2$—; A is —$CH_2NH$—; $Q^2$ is Ph(2-$NO_2$); and $J^1$ is |
| 128 | $J^2$ is —$CH_2$—; A is —$CH_2NH$—; $Q^2$ is Ph(2-Cl); and $J^1$ is |
| 129 | $J^2$ is —$CH_2$—; A is —$CH_2NH$—; $Q^2$ is Ph(2-$SO_2Me$); and $J^1$ is |
| 130 | $J^2$ is —$CH_2$—; A is —$CH_2NH$—; $Q^2$ is Ph(2-F,3-Cl); and $J^1$ is |
| 131 | $J^2$ is —$CH_2$—; A is —$NHCH_2$—; $Q^2$ is Ph(2-F); and $J^1$ is |
| 132 | $J^2$ is —$CH_2$—; A is —$NHCH_2$—; $Q^2$ is Ph(2,3-di-F); and $J^1$ is |
| 133 | $J^2$ is —$CH_2$—; A is —$NHCH_2$—; $Q^2$ is Ph(2,4-di-F); and $J^1$ is |
| 134 | $J^2$ is —$CH_2$—; A is —$NHCH_2$—; $Q^2$ is Ph(2,3,4-tri-F); and $J^1$ is |
| 135 | $J^2$ is —$CH_2$—; A is —$NHCH_2$—; $Q^2$ is Ph(2-$CF_3$); and $J^1$ is |
| 136 | $J^2$ is —$CH_2$—; A is —$NHCH_2$—; $Q^2$ is Ph(2-Me); and $J^1$ is |
| 137 | $J^2$ is —$CH_2$—; A is —$NHCH_2$—; $Q^2$ is Ph(2-$NO_2$); and $J^1$ is |
| 138 | $J^2$ is —$CH_2$—; A is —$NHCH_2$—; $Q^2$ is Ph(2-Cl); and $J^1$ is |
| 139 | $J^2$ is —$CH_2$—; A is —$NHCH_2$—; $Q^2$ is Ph(2-$SO_2Me$); and $J^1$ is |
| 140 | $J^2$ is —$CH_2$—; A is —$NHCH_2$—; $Q^2$ is Ph(2-F,3-Cl); and $J^1$ is |
| 141 | $J^2$ is —$CH_2$—; A is —HC=CH—; $Q^2$ is Ph(2-F); and $J^1$ is |
| 142 | $J^2$ is —$CH_2$—; A is —HC=CH—; $Q^2$ is Ph(2,3-di-F); and $J^1$ is |
| 143 | $J^2$ is —$CH_2$—; A is —HC=CH—; $Q^2$ is Ph(2,4-di-F); and $J^1$ is |
| 144 | $J^2$ is —$CH_2$—; A is —HC=CH—; $Q^2$ is Ph(2,3,4-tri-F); and $J^1$ is |
| 145 | $J^2$ is —$CH_2$—; A is —HC=CH—; $Q^2$ is Ph(2-$CF_3$); and $J^1$ is |
| 146 | $J^2$ is —$CH_2$—; A is —HC=CH—; $Q^2$ is Ph(2-Me); and $J^1$ is |
| 147 | $J^2$ is —$CH_2$—; A is —HC=CH—; $Q^2$ is Ph(2-$NO_2$); and $J^1$ is |
| 148 | $J^2$ is —$CH_2$—; A is —HC=CH—; $Q^2$ is Ph(2-Cl); and $J^1$ is |
| 149 | $J^2$ is —$CH_2$—; A is —HC=CH—; $Q^2$ is Ph(2-$SO_2Me$); and $J^1$ is |
| 150 | $J^2$ is —$CH_2$—; A is —HC=CH—; $Q^2$ is Ph(2-F,3-Cl); and $J^1$ is |
| 151 | $J^2$ is —$CH_2$—; A is —HC=CH—; $Q^2$ is Ph(2-F); and $J^1$ is |
| 152 | $J^2$ is —$CH_2$—; A is —HC=CH—; $Q^2$ is Ph(2,3-di-F); and $J^1$ is |
| 153 | $J^2$ is —$CH_2$—; A is —HC=CH—; $Q^2$ is Ph(2,4-di-F); and $J^1$ is |
| 154 | $J^2$ is —$CH_2$—; A is —HC=CH—; $Q^2$ is Ph(2,3,4-tri-F); and $J^1$ is |
| 155 | $J^2$ is —$CH_2$—; A is —HC=CH—; $Q^2$ is Ph(2-$CF_3$); and $J^1$ is |
| 156 | $J^2$ is —$CH_2$—; A is —HC=CH—; $Q^2$ is Ph(2-Me); and $J^1$ is |
| 157 | $J^2$ is —$CH_2$—; A is —HC=CH—; $Q^2$ is Ph(2-$NO_2$); and $J^1$ is |
| 158 | $J^2$ is —$CH_2$—; A is —HC=CH—; $Q^2$ is Ph(2-Cl); and $J^1$ is |
| 159 | $J^2$ is —$CH_2$—; A is —HC=CH—; $Q^2$ is Ph(2-$SO_2Me$); and $J^1$ is |
| 160 | $J^2$ is —$CH_2$—; A is —HC=CH—; $Q^2$ is Ph(2-F,3-Cl); and $J^1$ is |
| 161 | $J^2$ is —$CH_2$—; A is —HN=CH—; $Q^2$ is Ph(2-F); and $J^1$ is |
| 162 | $J^2$ is —$CH_2$—; A is —HN=CH—; $Q^2$ is Ph(2,3-di-F); and $J^1$ is |
| 163 | $J^2$ is —$CH_2$—; A is —HN=CH—; $Q^2$ is Ph(2,4-di-F); and $J^1$ is |
| 164 | $J^2$ is —$CH_2$—; A is —HN=CH—; $Q^2$ is Ph(2,3,4-tri-F); and $J^1$ is |
| 165 | $J^2$ is —$CH_2$—; A is —HN=CH—; $Q^2$ is Ph(2-$CF_3$); and $J^1$ is |
| 166 | $J^2$ is —$CH_2$—; A is —HN=CH—; $Q^2$ is Ph(2-Me); and $J^1$ is |
| 167 | $J^2$ is —$CH_2$—; A is —HN=CH—; $Q^2$ is Ph(2-$NO_2$); and $J^1$ is |
| 168 | $J^2$ is —$CH_2$—; A is —HN=CH—; $Q^2$ is Ph(2-Cl); and $J^1$ is |
| 169 | $J^2$ is —$CH_2$—; A is —HN=CH—; $Q^2$ is Ph(2-$SO_2Me$); and $J^1$ is |
| 170 | $J^2$ is —$CH_2$—; A is —HN=CH—; $Q^2$ is Ph(2-F,3-Cl); and $J^1$ is |
| 171 | $J^2$ is —$CH_2$—; A is —CHN=NH—; $Q^2$ is Ph(2-F); and $J^1$ is |
| 172 | $J^2$ is —$CH_2$—; A is —CHN=NH—; $Q^2$ is Ph(2,3-di-F); and $J^1$ is |
| 173 | $J^2$ is —$CH_2$—; A is —CHN=NH—; $Q^2$ is Ph(2,4-di-F); and $J^1$ is |
| 174 | $J^2$ is —$CH_2$—; A is —CHN=NH—; $Q^2$ is Ph(2,3,4-tri-F); and $J^1$ is |
| 175 | $J^2$ is —$CH_2$—; A is —CHN=NH—; $Q^2$ is Ph(2-$CF_3$); and $J^1$ is |
| 176 | $J^2$ is —$CH_2$—; A is —CHN=NH—; $Q^2$ is Ph(2-Me); and $J^1$ is |
| 177 | $J^2$ is —$CH_2$—; A is —CHN=NH—; $Q^2$ is Ph(2-$NO_2$); and $J^1$ is |
| 178 | $J^2$ is —$CH_2$—; A is —CHN=NH—; $Q^2$ is Ph(2-Cl); and $J^1$ is |
| 179 | $J^2$ is —$CH_2$—; A is —CHN=NH—; $Q^2$ is Ph(2-$SO_2Me$); and $J^1$ is |
| 180 | $J^2$ is —$CH_2$—; A is —CHN=NH—; $Q^2$ is Ph(2-F,3-Cl); and $J^1$ is |
| 181 | $J^2$ is —$CH_2CH_2$—; A is —$CH_2$—; $Q^2$ is Ph(2-F); and $J^1$ is |
| 182 | $J^2$ is —$CH_2CH_2$—; A is —$CH_2$—; $Q^2$ is Ph(2,3-di-F); and $J^1$ is |
| 183 | $J^2$ is —$CH_2CH_2$—; A is —$CH_2$—; $Q^2$ is Ph(2,4-di-F); and $J^1$ is |
| 184 | $J^2$ is —$CH_2CH_2$—; A is —$CH_2$—; $Q^2$ is Ph(2,3,4-tri-F); and $J^1$ is |
| 185 | $J^2$ is —$CH_2CH_2$—; A is —$CH_2$—; $Q^2$ is Ph(2-$CF_3$); and $J^1$ is |
| 186 | $J^2$ is —$CH_2CH_2$—; A is —$CH_2$—; $Q^2$ is Ph(2-Me); and $J^1$ is |
| 187 | $J^2$ is —$CH_2CH_2$—; A is —$CH_2$—; $Q^2$ is Ph(2-$NO_2$); and $J^1$ is |
| 188 | $J^2$ is —$CH_2CH_2$—; A is —$CH_2$—; $Q^2$ is Ph(2-Cl); and $J^1$ is |
| 189 | $J^2$ is —$CH_2CH_2$—; A is —$CH_2$—; $Q^2$ is Ph(2-$SO_2Me$); and $J^1$ is |
| 190 | $J^2$ is —$CH_2CH_2$—; A is —$CH_2$—; $Q^2$ is Ph(2-F,3-Cl); and $J^1$ is |
| 191 | $J^2$ is —$CH_2CH_2$—; A is —$CH_2CH_2$—; $Q^2$ is Ph(2-F); and $J^1$ is |
| 192 | $J^2$ is —$CH_2CH_2$—; A is —$CH_2CH_2$—; $Q^2$ is Ph(2,3-di-F); and $J^1$ is |
| 193 | $J^2$ is —$CH_2CH_2$—; A is —$CH_2CH_2$—; $Q^2$ is Ph(2,4-di-F); and $J^1$ is |
| 194 | $J^2$ is —$CH_2CH_2$—; A is —$CH_2CH_2$—; $Q^2$ is Ph(2,3,4-tri-F); and $J^1$ is |
| 195 | $J^2$ is —$CH_2CH_2$—; A is —$CH_2CH_2$—; $Q^2$ is Ph(2-$CF_3$); and $J^1$ is |
| 196 | $J^2$ is —$CH_2CH_2$—; A is —$CH_2CH_2$—; $Q^2$ is Ph(2-Me); and $J^1$ is |
| 197 | $J^2$ is —$CH_2CH_2$—; A is —$CH_2CH_2$—; $Q^2$ is Ph(2-$NO_2$); and $J^1$ is |
| 198 | $J^2$ is —$CH_2CH_2$—; A is —$CH_2CH_2$—; $Q^2$ is Ph(2-Cl); and $J^1$ is |

-continued

| Table | Row Heading |
|---|---|
| 199 | $J^2$ is —$CH_2CH_2$—; A is —$CH_2CH_2$—; $Q^2$ is Ph(2-$SO_2$Me); and $J^1$ is |
| 200 | $J^2$ is —$CH_2CH_2$—; A is —$CH_2CH_2$—; $Q^2$ is Ph(2-F,3-Cl); and $J^1$ is |
| 201 | $J^2$ is —$CH_2CH_2$—; A is —$CH_2CH_2CH_2$—; $Q^2$ is Ph(2-F); and $J^1$ is |
| 202 | $J^2$ is —$CH_2CH_2$—; A is —$CH_2CH_2CH_2$—; $Q^2$ is Ph(2,3-di-F); and $J^1$ is |
| 203 | $J^2$ is —$CH_2CH_2$—; A is —$CH_2CH_2CH_2$—; $Q^2$ is Ph(2,4-di-F); and $J^1$ is |
| 204 | $J^2$ is —$CH_2CH_2$—; A is —$CH_2CH_2CH_2$—; $Q^2$ is Ph(2,3,4-tri-F); and $J^1$ is |
| 205 | $J^2$ is —$CH_2CH_2$—; A is —$CH_2CH_2CH_2$—; $Q^2$ is Ph(2-$CF_3$); and $J^1$ is |
| 206 | $J^2$ is —$CH_2CH_2$—; A is —$CH_2CH_2CH_2$—; $Q^2$ is Ph(2-Me); and $J^1$ is |
| 207 | $J^2$ is —$CH_2CH_2$—; A is —$CH_2CH_2CH_2$—; $Q^2$ is Ph(2-$NO_2$); and $J^1$ is |
| 208 | $J^2$ is —$CH_2CH_2$—; A is —$CH_2CH_2CH_2$—; $Q^2$ is Ph(2-Cl); and $J^1$ is |
| 209 | $J^2$ is —$CH_2CH_2$—; A is —$CH_2CH_2CH_2$—; $Q^2$ is Ph(2-$SO_2$Me); and $J^1$ is |
| 210 | $J^2$ is —$CH_2CH_2$—; A is —$CH_2CH_2CH_2$—; $Q^2$ is Ph(2-F,3-Cl); and $J^1$ is |
| 211 | $J^2$ is —$CH_2CH_2$—; A is —O—; $Q^2$ is Ph(2-F); and $J^1$ is |
| 212 | $J^2$ is —$CH_2CH_2$—; A is —O—; $Q^2$ is Ph(2,3-di-F); and $J^1$ is |
| 213 | $J^2$ is —$CH_2CH_2$—; A is —O—; $Q^2$ is Ph(2,4-di-F); and $J^1$ is |
| 214 | $J^2$ is —$CH_2CH_2$—; A is —O—; $Q^2$ is Ph(2,3,4-tri-F); and $J^1$ is |
| 215 | $J^2$ is —$CH_2CH_2$—; A is —O—; $Q^2$ is Ph(2-$CF_3$); and $J^1$ is |
| 216 | $J^2$ is —$CH_2CH_2$—; A is —O—; $Q^2$ is Ph(2-Me); and $J^1$ is |
| 217 | $J^2$ is —$CH_2CH_2$—; A is —O—; $Q^2$ is Ph(2-$NO_2$); and $J^1$ is |
| 218 | $J^2$ is —$CH_2CH_2$—; A is —O—; $Q^2$ is Ph(2-Cl); and $J^1$ is |
| 219 | $J^2$ is —$CH_2CH_2$—; A is —O—; $Q^2$ is Ph(2-$SO_2$Me); and $J^1$ is |
| 220 | $J^2$ is —$CH_2CH_2$—; A is —O—; $Q^2$ is Ph(2-F,3-Cl); and $J^1$ is |
| 221 | $J^2$ is —$CH_2CH_2$—; A is —$OCH_2$—; $Q^2$ is Ph(2-F); and $J^1$ is |
| 222 | $J^2$ is —$CH_2CH_2$—; A is —$OCH_2$—; $Q^2$ is Ph(2,3-di-F); and $J^1$ is |
| 223 | $J^2$ is —$CH_2CH_2$—; A is —$OCH_2$—; $Q^2$ is Ph(2,4-di-F); and $J^1$ is |
| 224 | $J^2$ is —$CH_2CH_2$—; A is —$OCH_2$—; $Q^2$ is Ph(2,3,4-tri-F); and $J^1$ is |
| 225 | $J^2$ is —$CH_2CH_2$—; A is —$OCH_2$—; $Q^2$ is Ph(2-$CF_3$); and $J^1$ is |
| 226 | $J^2$ is —$CH_2CH_2$—; A is —$OCH_2$—; $Q^2$ is Ph(2-Me); and $J^1$ is |
| 227 | $J^2$ is —$CH_2CH_2$—; A is —$OCH_2$—; $Q^2$ is Ph(2-$NO_2$); and $J^1$ is |
| 228 | $J^2$ is —$CH_2CH_2$—; A is —$OCH_2$—; $Q^2$ is Ph(2-Cl); and $J^1$ is |
| 229 | $J^2$ is —$CH_2CH_2$—; A is —$OCH_2$—; $Q^2$ is Ph(2-$SO_2$Me); and $J^1$ is |
| 230 | $J^2$ is —$CH_2CH_2$—; A is —$OCH_2$—; $Q^2$ is Ph(2-F,3-Cl); and $J^1$ is |
| 231 | $J^2$ is —$CH_2CH_2$—; A is —$OCH_2CH_2$—; $Q^2$ is Ph(2-F); and $J^1$ is |
| 232 | $J^2$ is —$CH_2CH_2$—; A is —$OCH_2CH_2$—; $Q^2$ is Ph(2,3-di-F); and $J^1$ is |
| 233 | $J^2$ is —$CH_2CH_2$—; A is —$OCH_2CH_2$—; $Q^2$ is Ph(2,4-di-F); and $J^1$ is |
| 234 | $J^2$ is —$CH_2CH_2$—; A is —$OCH_2CH_2$—; $Q^2$ is Ph(2,3,4-tri-F); and $J^1$ is |
| 235 | $J^2$ is —$CH_2CH_2$—; A is —$OCH_2CH_2$—; $Q^2$ is Ph(2-$CF_3$); and $J^1$ is |
| 236 | $J^2$ is —$CH_2CH_2$—; A is —$OCH_2CH_2$—; $Q^2$ is Ph(2-Me); and $J^1$ is |
| 237 | $J^2$ is —$CH_2CH_2$—; A is —$OCH_2CH_2$—; $Q^2$ is Ph(2-$NO_2$); and $J^1$ is |
| 238 | $J^2$ is —$CH_2CH_2$—; A is —$OCH_2CH_2$—; $Q^2$ is Ph(2-Cl); and $J^1$ is |
| 239 | $J^2$ is —$CH_2CH_2$—; A is —$OCH_2CH_2$—; $Q^2$ is Ph(2-$SO_2$Me); and $J^1$ is |
| 240 | $J^2$ is —$CH_2CH_2$—; A is —$OCH_2CH_2$—; $Q^2$ is Ph(2-F,3-Cl); and $J^1$ is |
| 241 | $J^2$ is —$CH_2CH_2$—; A is —$CH_2O$—; $Q^2$ is Ph(2-F); and $J^1$ is |
| 242 | $J^2$ is —$CH_2CH_2$—; A is —$CH_2O$—; $Q^2$ is Ph(2,3-di-F); and $J^1$ is |
| 243 | $J^2$ is —$CH_2CH_2$—; A is —$CH_2O$—; $Q^2$ is Ph(2,4-di-F); and $J^1$ is |
| 244 | $J^2$ is —$CH_2CH_2$—; A is —$CH_2O$—; $Q^2$ is Ph(2,3,4-tri-F); and $J^1$ is |
| 245 | $J^2$ is —$CH_2CH_2$—; A is —$CH_2O$—; $Q^2$ is Ph(2-$CF_3$); and $J^1$ is |
| 246 | $J^2$ is —$CH_2CH_2$—; A is —$CH_2O$—; $Q^2$ is Ph(2-Me); and $J^1$ is |
| 247 | $J^2$ is —$CH_2CH_2$—; A is —$CH_2O$—; $Q^2$ is Ph(2-$NO_2$); and $J^1$ is |
| 248 | $J^2$ is —$CH_2CH_2$—; A is —$CH_2O$—; $Q^2$ is Ph(2-Cl); and $J^1$ is |
| 249 | $J^2$ is —$CH_2CH_2$—; A is —$CH_2O$—; $Q^2$ is Ph(2-$SO_2$Me); and $J^1$ is |
| 250 | $J^2$ is —$CH_2CH_2$—; A is —$CH_2O$—; $Q^2$ is Ph(2-F,3-Cl); and $J^1$ is |
| 251 | $J^2$ is —$CH_2CH_2$—; A is —$CH_2CH_2O$—; $Q^2$ is Ph(2-F); and $J^1$ is |
| 252 | $J^2$ is —$CH_2CH_2$—; A is —$CH_2CH_2O$—; $Q^2$ is Ph(2,3-di-F); and $J^1$ is |
| 253 | $J^2$ is —$CH_2CH_2$—; A is —$CH_2CH_2O$—; $Q^2$ is Ph(2,4-di-F); and $J^1$ is |
| 254 | $J^2$ is —$CH_2CH_2$—; A is —$CH_2CH_2O$—; $Q^2$ is Ph(2,3,4-tri-F); and $J^1$ is |
| 255 | $J^2$ is —$CH_2CH_2$—; A is —$CH_2CH_2O$—; $Q^2$ is Ph(2-$CF_3$); and $J^1$ is |
| 256 | $J^2$ is —$CH_2CH_2$—; A is —$CH_2CH_2O$—; $Q^2$ is Ph(2-Me); and $J^1$ is |
| 257 | $J^2$ is —$CH_2CH_2$—; A is —$CH_2CH_2O$—; $Q^2$ is Ph(2-$NO_2$); and $J^1$ is |
| 258 | $J^2$ is —$CH_2CH_2$—; A is —$CH_2CH_2O$—; $Q^2$ is Ph(2-Cl); and $J^1$ is |
| 259 | $J^2$ is —$CH_2CH_2$—; A is —$CH_2CH_2O$—; $Q^2$ is Ph(2-$SO_2$Me); and $J^1$ is |
| 260 | $J^2$ is —$CH_2CH_2$—; A is —$CH_2CH_2O$—; $Q^2$ is Ph(2-F,3-Cl); and $J^1$ is |
| 261 | $J^2$ is —$CH_2CH_2$—; A is —S—; $Q^2$ is Ph(2-F); and $J^1$ is |
| 262 | $J^2$ is —$CH_2CH_2$—; A is —S—; $Q^2$ is Ph(2,3-di-F); and $J^1$ is |
| 263 | $J^2$ is —$CH_2CH_2$—; A is —S—; $Q^2$ is Ph(2,4-di-F); and $J^1$ is |
| 264 | $J^2$ is —$CH_2CH_2$—; A is —S—; $Q^2$ is Ph(2,3,4-tri-F); and $J^1$ is |
| 265 | $J^2$ is —$CH_2CH_2$—; A is —S—; $Q^2$ is Ph(2-$CF_3$); and $J^1$ is |
| 266 | $J^2$ is —$CH_2CH_2$—; A is —S—; $Q^2$ is Ph(2-Me); and $J^1$ is |
| 267 | $J^2$ is —$CH_2CH_2$—; A is —S—; $Q^2$ is Ph(2-$NO_2$); and $J^1$ is |
| 268 | $J^2$ is —$CH_2CH_2$—; A is —S—; $Q^2$ is Ph(2-Cl); and $J^1$ is |
| 269 | $J^2$ is —$CH_2CH_2$—; A is —S—; $Q^2$ is Ph(2-$SO_2$Me); and $J^1$ is |
| 270 | $J^2$ is —$CH_2CH_2$—; A is —S—; $Q^2$ is Ph(2-F,3-Cl); and $J^1$ is |
| 271 | $J^2$ is —$CH_2CH_2$—; A is —$SCH_2$—; $Q^2$ is Ph(2-F); and $J^1$ is |
| 272 | $J^2$ is —$CH_2CH_2$—; A is —$SCH_2$—; $Q^2$ is Ph(2,3-di-F); and $J^1$ is |
| 273 | $J^2$ is —$CH_2CH_2$—; A is —$SCH_2$—; $Q^2$ is Ph(2,4-di-F); and $J^1$ is |
| 274 | $J^2$ is —$CH_2CH_2$—; A is —$SCH_2$—; $Q^2$ is Ph(2,3,4-tri-F); and $J^1$ is |
| 275 | $J^2$ is —$CH_2CH_2$—; A is —$SCH_2$—; $Q^2$ is Ph(2-$CF_3$); and $J^1$ is |

-continued

| Table | Row Heading |
|---|---|
| 276 | J² is —CH₂CH₂—; A is —SCH₂—; Q² is Ph(2-Me); and J¹ is |
| 277 | J² is —CH₂CH₂—; A is —SCH₂—; Q² is Ph(2-NO₂); and J¹ is |
| 278 | J² is —CH₂CH₂—; A is —SCH₂—; Q² is Ph(2-Cl); and J¹ is |
| 279 | J² is —CH₂CH₂—; A is —SCH₂—; Q² is Ph(2-SO₂Me); and J¹ is |
| 280 | J² is —CH₂CH₂—; A is —SCH₂—; Q² is Ph(2-F,3-Cl); and J¹ is |
| 281 | J² is —CH₂CH₂—; A is —CH₂S—; Q² is Ph(2-F); and J¹ is |
| 282 | J² is —CH₂CH₂—; A is —CH₂S—; Q² is Ph(2,3-di-F); and J¹ is |
| 283 | J² is —CH₂CH₂—; A is —CH₂S—; Q² is Ph(2,4-di-F); and J¹ is |
| 284 | J² is —CH₂CH₂—; A is —CH₂S—; Q² is Ph(2,3,4-tri-F); and J¹ is |
| 285 | J² is —CH₂CH₂—; A is —CH₂S—; Q² is Ph(2-CF₃); and J¹ is |
| 286 | J² is —CH₂CH₂—; A is —CH₂S—; Q² is Ph(2-Me); and J¹ is |
| 287 | J² is —CH₂CH₂—; A is —CH₂S—; Q² is Ph(2-NO₂); and J¹ is |
| 288 | J² is —CH₂CH₂—; A is —CH₂S—; Q² is Ph(2-Cl); and J¹ is |
| 289 | J² is —CH₂CH₂—; A is —CH₂S—; Q² is Ph(2-SO₂Me); and J¹ is |
| 290 | J² is —CH₂CH₂—; A is —CH₂S—; Q² is Ph(2-F,3-Cl); and J¹ is |
| 291 | J² is —CH₂CH₂—; A is —NH—; Q² is Ph(2-F); and J¹ is |
| 292 | J² is —CH₂CH₂—; A is —NH—; Q² is Ph(2,3-di-F); and J¹ is |
| 293 | J² is —CH₂CH₂—; A is —NH—; Q² is Ph(2,4-di-F); and J¹ is |
| 294 | J² is —CH₂CH₂—; A is —NH—; Q² is Ph(2,3,4-tri-F); and J¹ is |
| 295 | J² is —CH₂CH₂—; A is —NH—; Q² is Ph(2-CF₃); and J¹ is |
| 296 | J² is —CH₂CH₂—; A is —NH—; Q² is Ph(2-Me); and J¹ is |
| 297 | J² is —CH₂CH₂—; A is —NH—; Q² is Ph(2-NO₂); and J¹ is |
| 298 | J² is —CH₂CH₂—; A is —NH—; Q² is Ph(2-Cl); and J¹ is |
| 299 | J² is —CH₂CH₂—; A is —NH—; Q² is Ph(2-SO₂Me); and J¹ is |
| 300 | J² is —CH₂CH₂—; A is —NH—; Q² is Ph(2-F,3-Cl); and J¹ is |
| 301 | J² is —CH₂CH₂—; A is —CH₂NH—; Q² is Ph(2-F); and J¹ is |
| 302 | J² is —CH₂CH₂—; A is —CH₂NH—; Q² is Ph(2,3-di-F); and J¹ is |
| 303 | J² is —CH₂CH₂—; A is —CH₂NH—; Q² is Ph(2,4-di-F); and J¹ is |
| 304 | J² is —CH₂CH₂—; A is —CH₂NH—; Q² is Ph(2,3,4-tri-F); and J¹ is |
| 305 | J² is —CH₂CH₂—; A is —CH₂NH—; Q² is Ph(2-CF₃); and J¹ is |
| 306 | J² is —CH₂CH₂—; A is —CH₂NH—; Q² is Ph(2-Me); and J¹ is |
| 307 | J² is —CH₂CH₂—; A is —CH₂NH—; Q² is Ph(2-NO₂); and J¹ is |
| 308 | J² is —CH₂CH₂—; A is —CH₂NH—; Q² is Ph(2-Cl); and J¹ is |
| 309 | J² is —CH₂CH₂—; A is —CH₂NH—; Q² is Ph(2-SO₂Me); and J¹ is |
| 310 | J² is —CH₂CH₂—; A is —CH₂NH—; Q² is Ph(2-F,3-Cl); and J¹ is |
| 311 | J² is —CH₂CH₂—; A is —NHCH₂—; Q² is Ph(2-F); and J¹ is |
| 312 | J² is —CH₂CH₂—; A is —NHCH₂—; Q² is Ph(2,3-di-F); and J¹ is |
| 313 | J² is —CH₂CH₂—; A is —NHCH₂—; Q² is Ph(2,4-di-F); and J¹ is |
| 314 | J² is —CH₂CH₂—; A is —NHCH₂—; Q² is Ph(2,3,4-tri-F); and J¹ is |
| 315 | J² is —CH₂CH₂—; A is —NHCH₂—; Q² is Ph(2-CF₃); and J¹ is |
| 316 | J² is —CH₂CH₂—; A is —NHCH₂—; Q² is Ph(2-Me); and J¹ is |
| 317 | J² is —CH₂CH₂—; A is —NHCH₂—; Q² is Ph(2-NO₂); and J¹ is |
| 318 | J² is —CH₂CH₂—; A is —NHCH₂—; Q² is Ph(2-Cl); and J¹ is |
| 319 | J² is —CH₂CH₂—; A is —NHCH₂—; Q² is Ph(2-SO₂Me); and J¹ is |
| 320 | J² is —CH₂CH₂—; A is —NHCH₂—; Q² is Ph(2-F,3-Cl); and J¹ is |
| 321 | J² is —CH₂CH₂—; A is —HC=CH—; Q² is Ph(2-F); and J¹ is |
| 322 | J² is —CH₂CH₂—; A is —HC=CH—; Q² is Ph(2,3-di-F); and J¹ is |
| 323 | J² is —CH₂CH₂—; A is —HC=CH—; Q² is Ph(2,4-di-F); and J¹ is |
| 324 | J² is —CH₂CH₂—; A is —HC=CH—; Q² is Ph(2,3,4-tri-F); and J¹ is |
| 325 | J² is —CH₂CH₂—; A is —HC=CH—; Q² is Ph(2-CF₃); and J¹ is |
| 326 | J² is —CH₂CH₂—; A is —HC=CH—; Q² is Ph(2-Me); and J¹ is |
| 327 | J² is —CH₂CH₂—; A is —HC=CH—; Q² is Ph(2-NO₂); and J¹ is |
| 328 | J² is —CH₂CH₂—; A is —HC=CH—; Q² is Ph(2-Cl); and J¹ is |
| 329 | J² is —CH₂CH₂—; A is —HC=CH—; Q² is Ph(2-SO₂Me); and J¹ is |
| 330 | J² is —CH₂CH₂—; A is —HC=CH—; Q² is Ph(2-F,3-Cl); and J¹ is |
| 331 | J² is —CH₂CH₂—; A is —HC≡CH—; Q² is Ph(2-F); and J¹ is |
| 332 | J² is —CH₂CH₂—; A is —HC≡CH—; Q² is Ph(2,3-di-F); and J¹ is |
| 333 | J² is —CH₂CH₂—; A is —HC≡CH—; Q² is Ph(2,4-di-F); and J¹ is |
| 334 | J² is —CH₂CH₂—; A is —HC≡CH—; Q² is Ph(2,3,4-tri-F); and J¹ is |
| 335 | J² is —CH₂CH₂—; A is —HC≡CH—; Q² is Ph(2-CF₃); and J¹ is |
| 336 | J² is —CH₂CH₂—; A is —HC≡CH—; Q² is Ph(2-Me); and J¹ is |
| 337 | J² is —CH₂CH₂—; A is —HC≡CH—; Q² is Ph(2-NO₂); and J¹ is |
| 338 | J² is —CH₂CH₂—; A is —HC≡CH—; Q² is Ph(2-Cl); and J¹ is |
| 339 | J² is —CH₂CH₂—; A is —HC≡CH—; Q² is Ph(2-SO₂Me); and J¹ is |
| 340 | J² is —CH₂CH₂—; A is —HC≡CH—; Q² is Ph(2-F,3-Cl); and J¹ is |
| 341 | J² is —CH₂CH₂—; A is —HNN=CH—; Q² is Ph(2-F); and J¹ is |
| 342 | J² is —CH₂CH₂—; A is —HNN=CH—; Q² is Ph(2,3-di-F); and J¹ is |
| 343 | J² is —CH₂CH₂—; A is —HNN=CH—; Q² is Ph(2,4-di-F); and J¹ is |
| 344 | J² is —CH₂CH₂—; A is —HNN=CH—; Q² is Ph(2,3,4-tri-F); and J¹ is |
| 345 | J² is —CH₂CH₂—; A is —HNN=CH—; Q² is Ph(2-CF₃); and J¹ is |
| 346 | J² is —CH₂CH₂—; A is —HNN=CH—; Q² is Ph(2-Me); and J¹ is |
| 347 | J² is —CH₂CH₂—; A is —HNN=CH—; Q² is Ph(2-NO₂); and J¹ is |
| 348 | J² is —CH₂CH₂—; A is —HNN=CH—; Q² is Ph(2-Cl); and J¹ is |
| 349 | J² is —CH₂CH₂—; A is —HNN=CH—; Q² is Ph(2-SO₂Me); and J¹ is |
| 350 | J² is —CH₂CH₂—; A is —HNN=CH—; Q² is Ph(2-F,3-Cl); and J¹ is |
| 351 | J² is —CH₂CH₂—; A is —CHN=NH—; Q² is Ph(2-F); and J¹ is |
| 352 | J² is —CH₂CH₂—; A is —CHN=NH—; Q² is Ph(2,3-di-F); and J¹ is |

| Table | Row Heading |
|---|---|
| 353 | J² is —CH₂CH₂—; A is —CHN=NH—; Q² is Ph(2,4-di-F); and J¹ is |
| 354 | J² is —CH₂CH₂—; A is —CHN=NH—; Q² is Ph(2,3,4-tri-F); and J¹ is |
| 355 | J² is —CH₂CH₂—; A is —CHN=NH—; Q² is Ph(2-CF₃); and J¹ is |
| 356 | J² is —CH₂CH₂—; A is —CHN=NH—; Q² is Ph(2-Me); and J¹ is |
| 357 | J² is —CH₂CH₂—; A is —CHN=NH—; Q² is Ph(2-NO₂); and J¹ is |
| 358 | J² is —CH₂CH₂—; A is —CHN=NH—; Q² is Ph(2-Cl); and J¹ is |
| 359 | J² is —CH₂CH₂—; A is —CHN=NH—; Q² is Ph(2-SO₂Me); and J¹ is |
| 360 | J² is —CH₂CH₂—; A is —CHN=NH—; Q² is Ph(2-F,3-Cl); and J¹ is |

Table 361

Table 361 is constructed the same way as Table 1 above, except the structure is replaced with the following:

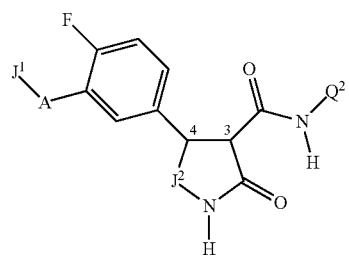

Tables 362 Through 720

This disclosure also includes Tables 362 through 720, each Table is constructed in the same fashion as Tables 2 through 360 above, except that the structure is replaced with the structure in Table 361 above.

Table 1081

Table 1081 is constructed the same way as Table 1 above, except the structure is replaced with the following:

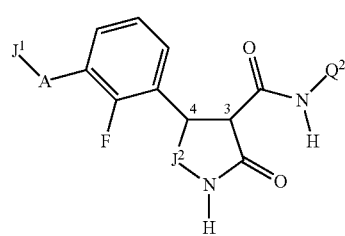

Tables 1082 Through 1440

This disclosure also includes Tables 1082 through 1440, each Table is constructed in the same fashion as Tables 2 through 360 above, except that the structure is replaced with the structure in Table 1081 above.

Table 1441

Table 1441 is constructed the same way as Table 1 above, except the structure is replaced with the following:

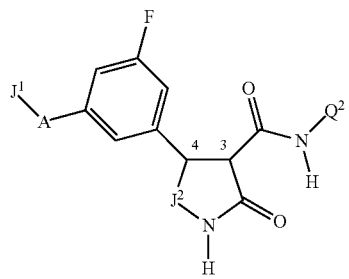

Tables 1442 Through 1800

This disclosure also includes Tables 1442 through 1800, each Table is constructed in the same fashion as Tables 2 through 360 above, except that the structure is replaced with the structure in Table 1441 above.

Table 1801

Table 1801 is constructed the same way as Table 1 above, except the structure is replaced with the following:

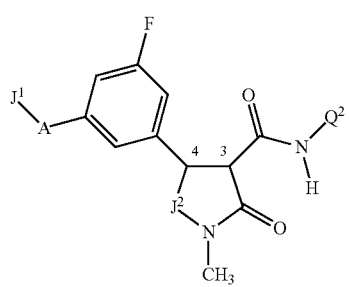

Tables 1802 Through 2160

This disclosure also includes Tables 1802 through 2160, each Table is constructed in the same fashion as Tables 2 through 360 above, except that the structure is replaced with the structure in Table 1801 above.

Table 2161

Table 2161 is constructed the same way as Table 1 above, except the structure is replaced with the following:

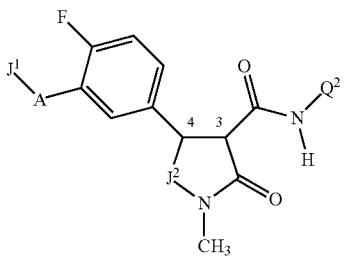

Tables 2162 Through 2520

This disclosure also includes Tables 2162 through 2520, each Table is constructed in the same fashion as Tables 2 through 360 above, except that the structure is replaced with the structure in Table 2161 above.

Table 2521

Table 2521 is constructed the same way as Table 1 above, except the structure is replaced with the following:

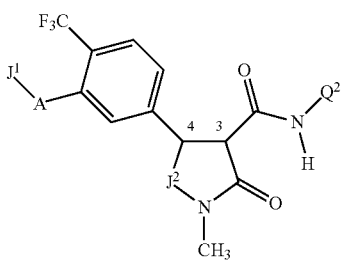

Tables 2522 Through 2880

This disclosure also includes Tables 2522 through 2880, each Table is constructed in the same fashion as Tables 2 through 360 above, except that the structure is replaced with the structure in Table 2521 above.

Table 2881

Table 2881 is constructed the same way as Table 1 above, except the structure is replaced with the following:

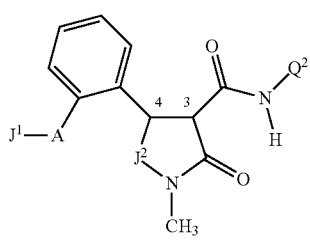

Tables 2882 Through 3240

This disclosure also includes Tables 2882 through 3240, each Table is constructed in the same fashion as Tables 2 through 360 above, except that the structure is replaced with the structure in Table 7561 above.

Table 3241

Table 3241 is constructed the same way as Table 1 above, except the structure is replaced with the following:

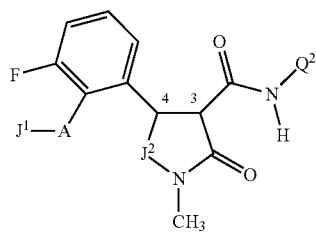

Tables 3242 Through 3600

This disclosure also includes Tables 3242 through 3600, each Table is constructed in the same fashion as Tables 2 through 360 above, except that the structure is replaced with the structure in Table 3241 above.

Table 3601

Table 3601 is constructed the same way as Table 1 above, except the structure is replaced with the following:

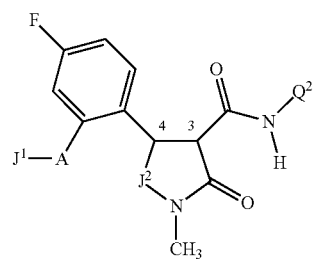

Tables 3602 Through 3960

This disclosure also includes Tables 3602 through 3960, each Table is constructed in the same fashion as Tables 2 through 360 above, except that the structure is replaced with the structure in Table 3601 above.

Table 3961

Table 3961 is constructed the same way as Table 1 above, except the structure is replaced with the following:

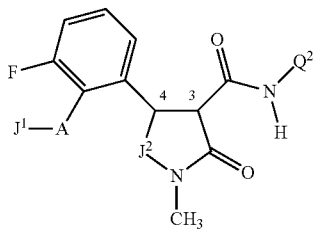

Tables 3962 Through 4320

This disclosure also includes Tables 3962 through 4320, each Table is constructed in the same fashion as Tables 2 through 360 above, except that the structure is replaced with the structure in Table 3961 above.

Table 4321

Table 4321 is constructed the same way as Table 1 above, except the structure is replaced with the following:

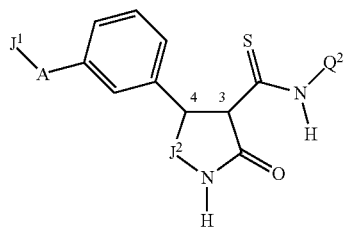

Tables 4322 Through 4680

This disclosure also includes Tables 4322 through 4680, each Table is constructed in the same fashion as Tables 2 through 360 above, except that the structure is replaced with the structure in Table 4321 above.

Table 4681

Table 4681 is constructed the same way as Table 1 above, except the structure is replaced with the following:

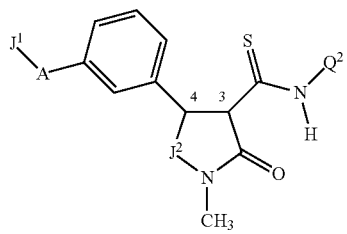

Tables 4682 Through 5040

This disclosure also includes Tables 4682 through 5040, each Table is constructed in the same fashion as Tables 2 through 360 above, except that the structure is replaced with the structure in Table 4681 above.

Table 5041

Table 5041 is constructed the same way as Table 1 above, except the structure is replaced with the following:

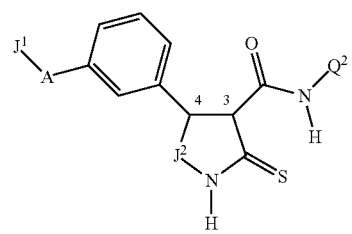

Tables 5042 Through 5400

This disclosure also includes Tables 5042 through 5400, each Table is constructed in the same fashion as Tables 2 through 360 above, except that the structure is replaced with the structure in Table 5041 above.

Table 5401

Table 5401 is constructed the same way as Table 1 above, except the structure is replaced with the following:

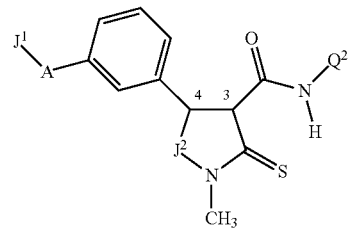

Tables 5402 Through 5760

This disclosure also includes Tables 5402 through 5760, each Table is constructed in the same fashion as Tables 2 through 360 above, except that the structure is replaced with the structure in Table 5401 above.

Table 5761

Table 5761 is constructed the same way as Table 1 above, except the structure is replaced with the following:

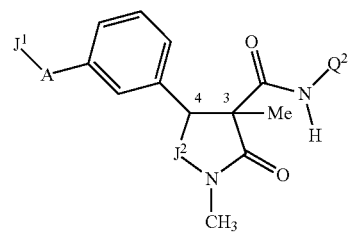

Tables 5762 Through 6120

This disclosure also includes Tables 5762 through 6120, each Table is constructed in the same fashion as Tables 2 through 360 above, except that the structure is replaced with the structure in Table 5761 above.

Formulation/Utility

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
|---|---|---|---|
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S.

Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 20 | 98.5% |
| silica aerogel | 0.5% |
| synthetic amorphous fine silica | 1.0% |

Example B

| Wettable Powder | |
|---|---|
| Compound 20 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 20 | 10.0% |
| attapulgite granules (low volatile matter, 0.71/0.30 mm; U.S.S. No. 25-50 sieves) | 90.0% |

Example D

| Extruded Pellet | |
|---|---|
| Compound 20 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 20 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 20 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Suspension Concentrate | |
|---|---|
| Compound 20 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

| Emulsion in Water | |
|---|---|
| Compound 20 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

| Oil Dispersion | |
|---|---|
| Compound 20 | 25% |
| polyoxyethylene sorbitol hexaoleate | 15% |
| organically modified bentonite clay | 2.5% |
| fatty acid methyl ester | 57.5% |

The present disclosure also includes Examples A through I above except the "Compound 20" is replaced with "Compound 1", "Compound 2", "Compound 3", "Compound 4", "Compound 5", "Compound 6", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 21", "Compound 22", "Compound 23", "Compound 24", "Compound 25", "Compound 26", "Compound 27", "Compound 28", "Compound 29", "Compound 30", "Compound 31", "Compound 32", "Compound 33", "Compound 34", "Compound 35", Compound 36, Compound 37, Compound 38, Compound 39, Compound 40, Compound 41, Compound 42, Compound 43, Compound 44, Compound 45, Compound 45, Compound 46, Compound 47, Compound 48, Compound 49, Compound 50, Compound 51, Compound 52, Compound 53, Compound 54, Compound 55, Compound 56, Compound 57, Compound 58, Compound 59, Compound 60, Compound 61, Compound 62, Compound 63, Compound 64, Compound 65, Compound 66, Compound 67, Compound 68, Compound 69, Compound 70, Compound 71, Compound 72, Compound 73, Compound 74, Compound 75, Compound 76, Compound 77, Compound 78, Compound 79, Compound 80, Compound 81, Compound 82, Compound 83, Compound 84, Compound 85, Compound 86, Compound 87, Compound 88, Compound 89 Compound 90, Compound 91, Compound 92, Compound 93 or Compound 94.

Test results indicate that the compounds of the present invention are highly active preemergent and/or postemergent herbicides and/or plant growth regulants. The compounds of the intention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

Compounds of this invention may show surprising selective activity controlling weed species growing in rice including, but not limited to, common waterplantain (*Alisma plantago-aquatica* L.), umbrella sedge (*Cyperus difformis* L.), rice flatsedge (*Cyperus iria* L.), junglerice (*Echinochloa colonum* (L.) LINK), barnyardgrass (*Echinochloa crus-galli* (L.) P.BEAUV.), early watergrass (2 Leaf Stage; *Echinochloa oryzoides* (ARD.) FRITSCH), late watergrass (2 Leaf Stage; *Echinochloa phyllopogon* (STAPF) KOSS./VASC.), Chinese waterchestnut (*Eleocharis dulcis* (BURM.f) TRIN. ex HENSCHEL), ducksalad (*Heteranthera limosa* (SW.) WILLD./VAHL), bearded sprangletop (*Leptochloa fascicularis* (LAM) GRAY), monochoria (*Monochoria vaginalis* (BURM.f) C.PRESL ex KUNTH), common arrowhead (*Sagittaria latifolia* WILLD.), California arrowhead (*Sagittaria montevidensis* CHAM. & SCHLECHT.), stiff arrowhead (*Sagittaria rigida* PURSH), Japanese bulrush (*Scirpus juncoides* ROXB.) and ricefield bulrush (*Scirpus mucronatus* L.).

Compounds of this invention also show particular activities (biological activity) controlling weed species growing in cereal crops including, but not limited to, blackgrass (*Alopecurus myosuroides* HUDS.), windgrass (*Apera spica-venti* (L.) BEAUV.), wild oats (*Avena fatua* L.), Italian ryegrass (*Lolium multiflorum* LAM.), littleseed canarygrass (*Phalaris minor* RETZ.), green foxtail (*Setaria viridis* (L.) P.BEAUV.).

As the compounds of the invention have (both preemergent and postemergent herbicidal) activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. A "-" means the entry is not available; "tol." means "tolerance" and "res." means resistance.

| Trait | Description |
|---|---|
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Modified flower color |
| T11 | ALS Herbicide tol. |
| T12 | Dicamba tol. |
| T13 | Anti-allergy |
| T14 | Salt tol. |
| T15 | Cold tol. |
| T16 | Imidazolinone herb. tol. |
| T17 | Modified alpha-amylase |
| T18 | Pollination control |
| T19 | 2,4-D tol. |
| T20 | Increased lysine |
| T21 | Drought tol. |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tol. |
| T31 | Modified oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Modified product |

Exhibit C

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |

-continued

| Crop | Event Name | Event Code | Trait(s) | Gene(s) |
| --- | --- | --- | --- | --- |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |

-continued

| Crop | Event Name | Event Code | Trait(s) | Gene(s) |
| --- | --- | --- | --- | --- |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |

-continued

| Crop | Event Name | Event Code | Trait(s) | Gene(s) |
| --- | --- | --- | --- | --- |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Although most typically, compounds of the invention are used to control undesired vegetation, contact of desired vegetation in the treated locus with compounds of the invention may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methyl sulfonyl)-N-(1-methyl-1H-tetrazol-5-yl)-4-(trifluoromethyl)benzamide and 2-methyl-N-(4-methyl-1,2,5-oxadiazol-3-yl)-3-(methyl sulfinyl)-4-(trifluoromethyl) benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th *Edition*, C. D. S. Tomlin, Ed., British Crop Protection Council, Farnham, Surrey, U. K., 2003 and *The BioPesticide Manual*, 2nd *Edition*, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention cans also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this invention with another herbicide. Table A1 lists particular combinations of Component (a) (i.e. a specific compound of the present invention) with another herbicide as Component (b) illustrative of the mixtures, compositions and methods of the present invention. Compound 20 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 17 in Index Table A) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
|---|---|---|---|---|
| 20 | 2,4-D | 1:192-6:1 | 1:64-2:1 | 1:24-1:3 |
| 20 | Acetochlor | 1:768-2:1 | 1:256-1:2 | 1:96-1:11 |
| 20 | Acifluorfen | 1:96-12:1 | 1:32-4:1 | 1:12-1:2 |
| 20 | Aclonifen | 1:857-2:1 | 1:285-1:3 | 1:107-1:12 |
| 20 | Alachlor | 1:768-2:1 | 1:256-1:2 | 1:96-1:11 |
| 20 | Ametryn | 1:384-3:1 | 1:128-1:1 | 1:48-1:6 |
| 20 | Amicarbazone | 1:192-6:1 | 1:64-2:1 | 1:24-1:3 |
| 20 | Amidosulfuron | 1:6-168:1 | 1:2-56:1 | 1:1-11:1 |
| 20 | Aminocyclopyrachlor | 1:48-24:1 | 1:16-8:1 | 1:6-2:1 |
| 20 | Aminopyralid | 1:20-56:1 | 1:6-19:1 | 1:2-4:1 |
| 20 | Amitrole | 1:768-2:1 | 1:256-1:2 | 1:96-1:11 |
| 20 | Anilofos | 1:96-12:1 | 1:32-4:1 | 1:12-1:2 |
| 20 | Asulam | 1:960-2:1 | 1:320-1:3 | 1:120-1:14 |
| 20 | Atrazine | 1:192-6:1 | 1:64-2:1 | 1:24-1:3 |
| 20 | Azimsulfuron | 1:6-168:1 | 1:2-56:1 | 1:1-11:1 |
| 20 | Beflubutamid | 1:342-4:1 | 1:114-2:1 | 1:42-1:5 |
| 20 | Benfuresate | 1:617-2:1 | 1:205-1:2 | 1:77-1:9 |
| 20 | Bensulfuron-methyl | 1:25-45:1 | 1:8-15:1 | 1:3-3:1 |
| 20 | Bentazone | 1:192-6:1 | 1:64-2:1 | 1:24-1:3 |
| 20 | Benzobicyclon | 1:85-14:1 | 1:28-5:1 | 1:10-1:2 |
| 20 | Benzofenap | 1:257-5:1 | 1:85-2:1 | 1:32-1:4 |
| 20 | Bicyclopyrone | 1:42-27:1 | 1:14-9:1 | 1:5-2:1 |
| 20 | Bifenox | 1:257-5:1 | 1:85-2:1 | 1:32-1:4 |
| 20 | Bispyribac-sodium | 1:10-112:1 | 1:3-38:1 | 1:1-7:1 |
| 20 | Bromacil | 1:384-3:1 | 1:128-1:1 | 1:48-1:6 |
| 20 | Bromobutide | 1:384-3:1 | 1:128-1:1 | 1:48-1:6 |
| 20 | Bromoxynil | 1:96-12:1 | 1:32-4:1 | 1:12-1:2 |
| 20 | Butachlor | 1:768-2:1 | 1:256-1:2 | 1:96-1:11 |
| 20 | Butafenacil | 1:42-27:1 | 1:14-9:1 | 1:5-2:1 |

TABLE A1-continued

| Component (a) (Compound #) | Component (b) | Typical Weight Ratio | More Typical Weight Ratio | Most Typical Weight Ratio |
|---|---|---|---|---|
| 20 | Butylate | 1:1542-1:2 | 1:514-1:5 | 1:192-1:22 |
| 20 | Carfenstrole | 1:192-6:1 | 1:64-2:1 | 1:24-1:3 |
| 20 | Carfentrazone-ethyl | 1:128-9:1 | 1:42-3:1 | 1:16-1:2 |
| 20 | Chlorimuron-ethyl | 1:8-135:1 | 1:2-45:1 | 1:1-9:1 |
| 20 | Chlorotoluron | 1:768-2:1 | 1:256-1:2 | 1:96-1:11 |
| 20 | Chlorsulfuron | 1:6-168:1 | 1:2-56:1 | 1:1-11:1 |
| 20 | Cincosulfuron | 1:17-68:1 | 1:5-23:1 | 1:2-5:1 |
| 20 | Cinidon-ethyl | 1:384-3:1 | 1:128-1:1 | 1:48-1:6 |
| 20 | Cinmethylin | 1:34-34:1 | 1:11-12:1 | 1:4-3:1 |
| 20 | Clacyfos | 1:34-34:1 | 1:11-12:1 | 1:4-3:1 |
| 20 | Clethodim | 1:48-24:1 | 1:16-8:1 | 1:6-2:1 |
| 20 | Clodinafop-propargyl | 1:20-56:1 | 1:6-19:1 | 1:2-4:1 |
| 20 | Clomazone | 1:384-3:1 | 1:128-1:1 | 1:48-1:6 |
| 20 | Clomeprop | 1:171-7:1 | 1:57-3:1 | 1:21-1:3 |
| 20 | Clopyralid | 1:192-6:1 | 1:64-2:1 | 1:24-1:3 |
| 20 | Cloransulam-methyl | 1:12-96:1 | 1:4-32:1 | 1:1-6:1 |
| 20 | Cumyluron | 1:384-3:1 | 1:128-1:1 | 1:48-1:6 |
| 20 | Cyanazine | 1:384-3:1 | 1:128-1:1 | 1:48-1:6 |
| 20 | Cyclopyrimorate | 1:17-68:1 | 1:5-23:1 | 1:2-5:1 |
| 20 | Cyclosulfamuron | 1:17-68:1 | 1:5-23:1 | 1:2-5:1 |
| 20 | Cycloxydim | 1:96-12:1 | 1:32-4:1 | 1:12-1:2 |
| 20 | Cyhalofop | 1:25-45:1 | 1:8-15:1 | 1:3-3:1 |
| 20 | Daimuron | 1:192-6:1 | 1:64-2:1 | 1:24-1:3 |
| 20 | Desmedipham | 1:322-4:1 | 1:107-2:1 | 1:40-1:5 |
| 20 | Dicamba | 1:192-6:1 | 1:64-2:1 | 1:24-1:3 |
| 20 | Dichlobenil | 1:1371-1:2 | 1:457-1:4 | 1:171-1:20 |
| 20 | Dichlorprop | 1:925-2:1 | 1:308-1:3 | 1:115-1:13 |
| 20 | Diclofop-methyl | 1:384-3:1 | 1:128-1:1 | 1:48-1:6 |
| 20 | Diclosulam | 1:10-112:1 | 1:3-38:1 | 1:1-7:1 |
| 20 | Difenzoquat | 1:288-4:1 | 1:96-2:1 | 1:36-1:4 |
| 20 | Diflufenican | 1:857-2:1 | 1:285-1:3 | 1:107-1:12 |
| 20 | Diflufenzopyr | 1:12-96:1 | 1:4-32:1 | 1:1-6:1 |
| 20 | Dimethachlor | 1:768-2:1 | 1:256-1:2 | 1:96-1:11 |
| 20 | Dimethametryn | 1:192-6:1 | 1:64-2:1 | 1:24-1:3 |
| 20 | Dimethenamid-P | 1:384-3:1 | 1:128-1:1 | 1:48-1:6 |
| 20 | Dithiopyr | 1:192-6:1 | 1:64-2:1 | 1:24-1:3 |
| 20 | Diuron | 1:384-3:1 | 1:128-1:1 | 1:48-1:6 |
| 20 | EPTC | 1:768-2:1 | 1:256-1:2 | 1:96-1:11 |
| 20 | Esprocarb | 1:1371-1:2 | 1:457-1:4 | 1:171-1:20 |
| 20 | Ethalfluralin | 1:384-3:1 | 1:128-1:1 | 1:48-1:6 |
| 20 | Ethametsulfuron-methyl | 1:17-68:1 | 1:5-23:1 | 1:2-5:1 |
| 20 | Ethoxyfen | 1:8-135:1 | 1:2-45:1 | 1:1-9:1 |
| 20 | Ethoxysulfuron | 1:20-56:1 | 1:6-19:1 | 1:2-4:1 |
| 20 | Etobenzanid | 1:257-5:1 | 1:85-2:1 | 1:32-1:4 |
| 20 | Fenoxaprop-ethyl | 1:120-10:1 | 1:40-4:1 | 1:15-1:2 |
| 20 | Fenoxasulfone | 1:85-14:1 | 1:28-5:1 | 1:10-1:2 |
| 20 | Fenquinotrione | 1:17-68:1 | 1:5-23:1 | 1:2-5:1 |
| 20 | Fentrazamide | 1:17-68:1 | 1:5-23:1 | 1:2-5:1 |
| 20 | Flazasulfuron | 1:17-68:1 | 1:5-23:1 | 1:2-5:1 |
| 20 | Florasulam | 1:2-420:1 | 1:1-140:1 | 2:1-27:1 |
| 20 | Fluazifop-butyl | 1:192-6:1 | 1:64-2:1 | 1:24-1:3 |
| 20 | Flucarbazone | 1:8-135:1 | 1:2-45:1 | 1:1-9:1 |
| 20 | Flucetosulfuron | 1:8-135:1 | 1:2-45:1 | 1:1-9:1 |
| 20 | Flufenacet | 1:257-5:1 | 1:85-2:1 | 1:32-1:4 |
| 20 | Flumetsulam | 1:24-48:1 | 1:8-16:1 | 1:3-3:1 |
| 20 | Flumiclorac-pentyl | 1:10-112:1 | 1:3-38:1 | 1:1-7:1 |
| 20 | Flumioxazin | 1:25-45:1 | 1:8-15:1 | 1:3-3:1 |
| 20 | Fluometuron | 1:384-3:1 | 1:128-1:1 | 1:48-1:6 |
| 20 | Flupyrsulfuron-methyl | 1:3-336:1 | 1:1-112:1 | 2:1-21:1 |
| 20 | Fluridone | 1:384-3:1 | 1:128-1:1 | 1:48-1:6 |
| 20 | Fluroxypyr | 1:96-12:1 | 1:32-4:1 | 1:12-1:2 |
| 20 | Flurtamone | 1:857-2:1 | 1:285-1:3 | 1:107-1:12 |
| 20 | Fluthiacet-methyl | 1:48-42:1 | 1:16-14:1 | 1:3-3:1 |
| 20 | Fomesafen | 1:96-12:1 | 1:32-4:1 | 1:12-1:2 |
| 20 | Foramsulfuron | 1:13-84:1 | 1:4-28:1 | 1:1-6:1 |
| 20 | Glufosinate | 1:288-4:1 | 1:96-2:1 | 1:36-1:4 |
| 20 | Glyphosate | 1:288-4:1 | 1:96-2:1 | 1:36-1:4 |
| 20 | Halosulfuron-methyl | 1:17-68:1 | 1:5-23:1 | 1:2-5:1 |
| 20 | Halauxifen | 1:20-56:1 | 1:6-19:1 | 1:2-4:1 |
| 20 | Halauxifen methyl | 1:20-56:1 | 1:6-19:1 | 1:2-4:1 |
| 20 | Haloxyfop-methyl | 1:34-34:1 | 1:11-12:1 | 1:4-3:1 |
| 20 | Hexazinone | 1:192-6:1 | 1:64-2:1 | 1:24-1:3 |
| 20 | Hydantocidin | 1:1100-16:1 | 1:385-8:1 | 1:144-4:1 |
| 20 | Imazamox | 1:13-84:1 | 1:4-28:1 | 1:1-6:1 |
| 20 | Imazapic | 1:20-56:1 | 1:6-19:1 | 1:2-4:1 |
| 20 | Imazapyr | 1:85-14:1 | 1:28-5:1 | 1:10-1:2 |
| 20 | Imazaquin | 1:34-34:1 | 1:11-12:1 | 1:4-3:1 |

TABLE A1-continued

| Component (a) (Compound #) | Component (b) | Typical Weight Ratio | More Typical Weight Ratio | Most Typical Weight Ratio |
|---|---|---|---|---|
| 20 | Imazethabenz-methyl | 1:171-7:1 | 1:57-3:1 | 1:21-1:3 |
| 20 | Imazethapyr | 1:24-48:1 | 1:8-16:1 | 1:3-3:1 |
| 20 | Imazosulfuron | 1:27-42:1 | 1:9-14:1 | 1:3-3:1 |
| 20 | Indanofan | 1:342-4:1 | 1:114-2:1 | 1:42-1:5 |
| 20 | Indaziflam | 1:25-45:1 | 1:8-15:1 | 1:3-3:1 |
| 20 | Iodosulfuron-methyl | 1:3-336:1 | 1:1-112:1 | 2:1-21:1 |
| 20 | Ioxynil | 1:192-6:1 | 1:64-2:1 | 1:24-1:3 |
| 20 | Ipfencarbazone | 1:85-14:1 | 1:28-5:1 | 1:10-1:2 |
| 20 | Isoproturon | 1:384-3:1 | 1:128-1:1 | 1:48-1:6 |
| 20 | Isoxaben | 1:288-4:1 | 1:96-2:1 | 1:36-1:4 |
| 20 | Isoxaflutole | 1:60-20:1 | 1:20-7:1 | 1:7-2:1 |
| 20 | Lactofen | 1:42-27:1 | 1:14-9:1 | 1:5-2:1 |
| 20 | Lenacil | 1:384-3:1 | 1:128-1:1 | 1:48-1:6 |
| 20 | Linuron | 1:384-3:1 | 1:128-1:1 | 1:48-1:6 |
| 20 | MCPA | 1:192-6:1 | 1:64-2:1 | 1:24-1:3 |
| 20 | MCPB | 1:288-4:1 | 1:96-2:1 | 1:36-1:4 |
| 20 | Mecoprop | 1:768-2:1 | 1:256-1:2 | 1:96-1:11 |
| 20 | Mefenacet | 1:384-3:1 | 1:128-1:1 | 1:48-1:6 |
| 20 | Mefluidide | 1:192-6:1 | 1:64-2:1 | 1:24-1:3 |
| 20 | Mesosulfuron-methyl | 1:5-224:1 | 1:1-75:1 | 1:1-14:1 |
| 20 | Mesotrione | 1:42-27:1 | 1:14-9:1 | 1:5-2:1 |
| 20 | Metamifop | 1:42-27:1 | 1:14-9:1 | 1:5-2:1 |
| 20 | Metazachlor | 1:384-3:1 | 1:128-1:1 | 1:48-1:6 |
| 20 | Metazosulfuron | 1:25-45:1 | 1:8-15:1 | 1:3-3:1 |
| 20 | Methabenzthiazuron | 1:768-2:1 | 1:256-1:2 | 1:96-1:11 |
| 20 | Metolachlor | 1:768-2:1 | 1:256-1:2 | 1:96-1:11 |
| 20 | Metosulam | 1:8-135:1 | 1:2-45:1 | 1:1-9:1 |
| 20 | Metribuzin | 1:192-6:1 | 1:64-2:1 | 1:24-1:3 |
| 20 | Metsulfuron-methyl | 1:2-560:1 | 1:1-187:1 | 3:1-35:1 |
| 20 | Molinate | 1:1028-2:1 | 1:342-1:3 | 1:128-1:15 |
| 20 | Napropamide | 1:384-3:1 | 1:128-1:1 | 1:48-1:6 |
| 20 | Napropamide-M | 1:192-6:1 | 1:64-2:1 | 1:24-1:3 |
| 20 | Naptalam | 1:192-6:1 | 1:64-2:1 | 1:24-1:3 |
| 20 | Nicosulfuron | 1:12-96:1 | 1:4-32:1 | 1:1-6:1 |
| 20 | Norflurazon | 1:1152-1:1 | 1:384-1:3 | 1:144-1:16 |
| 20 | Orbencarb | 1:1371-1:2 | 1:457-1:4 | 1:171-1:20 |
| 20 | Orthosulfamuron | 1:20-56:1 | 1:6-19:1 | 1:2-4:1 |
| 20 | Oryzalin | 1:514-3:1 | 1:171-1:2 | 1:64-1:8 |
| 20 | Oxadiargyl | 1:384-3:1 | 1:128-1:1 | 1:48-1:6 |
| 20 | Oxadiazon | 1:548-3:1 | 1:182-1:2 | 1:68-1:8 |
| 20 | Oxasulfuron | 1:27-42:1 | 1:9-14:1 | 1:3-3:1 |
| 20 | Oxaziclomefone | 1:42-27:1 | 1:14-9:1 | 1:5-2:1 |
| 20 | Oxyfluorfen | 1:384-3:1 | 1:128-1:1 | 1:48-1:6 |
| 20 | Paraquat | 1:192-6:1 | 1:64-2:1 | 1:24-1:3 |
| 20 | Pendimethalin | 1:384-3:1 | 1:128-1:1 | 1:48-1:6 |
| 20 | Penoxsulam | 1:10-112:1 | 1:3-38:1 | 1:1-7:1 |
| 20 | Penthoxamid | 1:384-3:1 | 1:128-1:1 | 1:48-1:6 |
| 20 | Pentoxazone | 1:102-12:1 | 1:34-4:1 | 1:12-1:2 |
| 20 | Phenmedipham | 1:102-12:1 | 1:34-4:1 | 1:12-1:2 |
| 20 | Picloram | 1:96-12:1 | 1:32-4:1 | 1:12-1:2 |
| 20 | Picolinafen | 1:34-34:1 | 1:11-12:1 | 1:4-3:1 |
| 20 | Pinoxaden | 1:25-45:1 | 1:8-15:1 | 1:3-3:1 |
| 20 | Pretilachlor | 1:192-6:1 | 1:64-2:1 | 1:24-1:3 |
| 20 | Primisulfuron-methyl | 1:8-135:1 | 1:2-45:1 | 1:1-9:1 |
| 20 | Prodiamine | 1:384-3:1 | 1:128-1:1 | 1:48-1:6 |
| 20 | Profoxydim | 1:42-27:1 | 1:14-9:1 | 1:5-2:1 |
| 20 | Prometryn | 1:384-3:1 | 1:128-1:1 | 1:48-1:6 |
| 20 | Propachlor | 1:1152-1:1 | 1:384-1:3 | 1:144-1:16 |
| 20 | Propanil | 1:384-3:1 | 1:128-1:1 | 1:48-1:6 |
| 20 | Propaquizafop | 1:48-24:1 | 1:16-8:1 | 1:6-2:1 |
| 20 | Propoxycarbazone | 1:17-68:1 | 1:5-23:1 | 1:2-5:1 |
| 20 | Propyrisulfuron | 1:17-68:1 | 1:5-23:1 | 1:2-5:1 |
| 20 | Propyzamide | 1:384-3:1 | 1:128-1:1 | 1:48-1:6 |
| 20 | Prosulfocarb | 1:1200-1:2 | 1:400-1:4 | 1:150-1:17 |
| 20 | Prosulfuron | 1:6-168:1 | 1:2-56:1 | 1:1-11:1 |
| 20 | Pyraclonil | 1:42-27:1 | 1:14-9:1 | 1:5-2:1 |
| 20 | Pyraflufen-ethyl | 1:5-224:1 | 1:1-75:1 | 1:1-14:1 |
| 20 | Pyrasulfotole | 1:13-84:1 | 1:4-28:1 | 1:1-6:1 |
| 20 | Pyrazolynate | 1:857-2:1 | 1:285-1:3 | 1:107-1:12 |
| 20 | Pyrazosulfuron-ethyl | 1:10-112:1 | 1:3-38:1 | 1:1-7:1 |
| 20 | Pyrazoxyfen | 1:5-224:1 | 1:1-75:1 | 1:1-14:1 |
| 20 | Pyribenzoxim | 1:10-112:1 | 1:3-38:1 | 1:1-7:1 |
| 20 | Pyributicarb | 1:384-3:1 | 1:128-1:1 | 1:48-1:6 |
| 20 | Pyridate | 1:288-4:1 | 1:96-2:1 | 1:36-1:4 |
| 20 | Pyriftalid | 1:10-112:1 | 1:3-38:1 | 1:1-7:1 |
| 20 | Pyriminobac-methyl | 1:20-56:1 | 1:6-19:1 | 1:2-4:1 |
| 20 | Pyrimisulfan | 1:17-68:1 | 1:5-23:1 | 1:2-5:1 |

TABLE A1-continued

| Component (a) (Compound #) | Component (b) | Typical Weight Ratio | More Typical Weight Ratio | Most Typical Weight Ratio |
|---|---|---|---|---|
| 20 | Pyrithiobac | 1:24-48:1 | 1:8-16:1 | 1:3-3:1 |
| 20 | Pyroxasulfone | 1:85-14:1 | 1:28-5:1 | 1:10-1:2 |
| 20 | Pyroxsulam | 1:5-224:1 | 1:1-75:1 | 1:1-14:1 |
| 20 | Quinclorac | 1:192-6:1 | 1:64-2:1 | 1:24-1:3 |
| 20 | Quizalofop-ethyl | 1:42-27:1 | 1:14-9:1 | 1:5-2:1 |
| 20 | Rimsulfuron | 1:13-84:1 | 1:4-28:1 | 1:1-6:1 |
| 20 | Saflufenacil | 1:25-45:1 | 1:8-15:1 | 1:3-3:1 |
| 20 | Sethoxydim | 1:96-12:1 | 1:32-4:1 | 1:12-1:2 |
| 20 | Simazine | 1:384-3:1 | 1:128-1:1 | 1:48-1:6 |
| 20 | Sulcotrione | 1:120-10:1 | 1:40-4:1 | 1:15-1:2 |
| 20 | Sulfentrazone | 1:147-8:1 | 1:49-3:1 | 1:18-1:3 |
| 20 | Sulfometuron-methyl | 1:34-34:1 | 1:11-12:1 | 1:4-3:1 |
| 20 | Sulfosulfuron | 1:8-135:1 | 1:2-45:1 | 1:1-9:1 |
| 20 | Tebuthiuron | 1:384-3:1 | 1:128-1:1 | 1:48-1:6 |
| 20 | Tefuryltrione | 1:42-27:1 | 1:14-9:1 | 1:5-2:1 |
| 20 | Tembotrione | 1:31-37:1 | 1:10-13:1 | 1:3-3:1 |
| 20 | Tepraloxydim | 1:25-45:1 | 1:8-15:1 | 1:3-3:1 |
| 20 | Terbacil | 1:288-4:1 | 1:96-2:1 | 1:36-1:4 |
| 20 | Terbuthylazine | 1:857-2:1 | 1:285-1:3 | 1:107-1:12 |
| 20 | Terbutryn | 1:192-6:1 | 1:64-2:1 | 1:24-1:3 |
| 20 | Thenylchlor | 1:85-14:1 | 1:28-5:1 | 1:10-1:2 |
| 20 | Thiazopyr | 1:384-3:1 | 1:128-1:1 | 1:48-1:6 |
| 20 | Thiencarbazone | 1:3-336:1 | 1:1-112:1 | 2:1-21:1 |
| 20 | Thifensulfuron-methyl | 1:5-224:1 | 1:1-75:1 | 1:1-14:1 |
| 20 | Tiafenacil | 1:17-68:1 | 1:5-23:1 | 1:2-5:1 |
| 20 | Thiobencarb | 1:768-2:1 | 1:256-1:2 | 1:96-1:11 |
| 20 | Tolpyralate | 1:31-37:1 | 1:10-13:1 | 1:3-3:1 |
| 20 | Topramzone | 1:6-168:1 | 1:2-56:1 | 1:1-11:1 |
| 20 | Tralkoxydim | 1:68-17:1 | 1:22-6:1 | 1:8-2:1 |
| 20 | Triafamone | 1:2-420:1 | 1:1-140:1 | 2:1-27:1 |
| 20 | Triallate | 1:768-2:1 | 1:256-1:2 | 1:96-1:11 |
| 20 | Triasulfuron | 1:5-224:1 | 1:1-75:1 | 1:1-14:1 |
| 20 | Triaziflam | 1:171-7:1 | 1:57-3:1 | 1:21-1:3 |
| 20 | Tribenuron-methyl | 1:3-336:1 | 1:1-112:1 | 2:1-21:1 |
| 20 | Triclopyr | 1:192-6:1 | 1:64-2:1 | 1:24-1:3 |
| 20 | Trifloxysulfuron | 1:2-420:1 | 1:1-140:1 | 2:1-27:1 |
| 20 | Trifludimoxazin | 1:25-45:1 | 1:8-15:1 | 1:3-3:1 |
| 20 | Trifluralin | 1:288-4:1 | 1:96-2:1 | 1:36-1:4 |
| 20 | Triflusulfuron-methyl | 1:17-68:1 | 1:5-23:1 | 1:2-5:1 |
| 20 | Tritosulfuron | 1:13-84:1 | 1:4-28:1 | 1:1-6:1 |

Table A2 is constructed the same as Table A1 above except that entries below the "Component (a)" column heading (i.e. "20") are replaced with the respective Component (a) Column Entries shown below. Compound # in the Component (a) column is identified in Index Table A. Thus, for example, in Table A2 the entries below the "Component (a)" column heading all recite "Compound 1" (i.e. Compound 1 identified in Index Table A), and the first line below the column headings in Table A2 specifically discloses a mixture of Compound 1 with 2,4-D. Tables A3 through A94 are constructed similarly.

| Table Number | Component (a) Column Entries |
|---|---|
| A2 | Compound 1 |
| A3 | Compound 2 |
| A4 | Compound 3 |
| A5 | Compound 4 |
| A6 | Compound 5 |
| A7 | Compound 6 |
| A8 | Compound 7 |
| A9 | Compound 8 |
| A10 | Compound 9 |
| A11 | Compound 10 |
| A12 | Compound 11 |
| A13 | Compound 12 |
| A14 | Compound 13 |
| A15 | Compound 14 |
| A16 | Compound 15 |
| A17 | Compound 16 |

-continued

| Table Number | Component (a) Column Entries |
|---|---|
| A18 | Compound 17 |
| A19 | Compound 18 |
| A20 | Compound 19 |
| A21 | Compound 21 |
| A22 | Compound 22 |
| A23 | Compound 23 |
| A24 | Compound 24 |
| A25 | Compound 25 |
| A26 | Compound 26 |
| A27 | Compound 27 |
| A28 | Compound 28 |
| A29 | Compound 29 |
| A30 | Compound 30 |
| A31 | Compound 31 |
| A32 | Compound 32 |
| A33 | Compound 33 |
| A34 | Compound 34 |
| A35 | Compound 35 |
| A36 | Compound 36 |
| A37 | Compound 37 |
| A38 | Compound 38 |
| A39 | Compound 39 |
| A40 | Compound 40 |
| A41 | Compound 41 |
| A42 | Compound 42 |
| A43 | Compound 43 |
| A44 | Compound 44 |
| A45 | Compound 45 |
| A46 | Compound 46 |

-continued

| Table Number | Component (a) Column Entries |
|---|---|
| A47 | Compound 47 |
| A48 | Compound 48 |
| A49 | Compound 49 |
| A50 | Compound 50 |
| A51 | Compound 51 |
| A52 | Compound 52 |
| A53 | Compound 53 |
| A54 | Compound 54 |
| A55 | Compound 55 |
| A56 | Compound 56 |
| A57 | Compound 57 |
| A58 | Compound 58 |
| A59 | Compound 59 |
| A60 | Compound 60 |
| A61 | Compound 61 |
| A62 | Compound 62 |
| A63 | Compound 63 |
| A64 | Compound 64 |
| A65 | Compound 65 |
| A66 | Compound 66 |
| A67 | Compound 67 |
| A68 | Compound 68 |
| A69 | Compound 69 |
| A70 | Compound 70 |
| A70 | Compound 70 |
| A71 | Compound 71 |
| A72 | Compound 72 |
| A73 | Compound 73 |
| A74 | Compound 74 |
| A75 | Compound 75 |
| A76 | Compound 76 |
| A77 | Compound 77 |
| A78 | Compound 78 |
| A79 | Compound 79 |
| A80 | Compound 80 |
| A81 | Compound 81 |
| A82 | Compound 82 |
| A83 | Compound 83 |
| A84 | Compound 84 |
| A85 | Compound 85 |
| A86 | Compound 86 |
| A87 | Compound 87 |
| A88 | Compound 88 |
| A89 | Compound 89 |
| A90 | Compound 90 |
| A91 | Compound 91 |
| A92 | Compound 92 |
| A93 | Compound 93 |
| A94 | Compound 94 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this invention against specific weeds. The weed control afforded by the compounds is not limited, however, to these species. See Index Tables A for compound descriptions. The following abbreviations are used in the Index Tables which follow: t is tertiary, s is secondary, n is normal, i is iso, c is cyclo, Me is methyl, Et is ethyl, Pr is propyl, i-Pr is isopropyl, Bu is butyl, c-Pr is cyclopropyl, t-Bu is tert-butyl, Ph is phenyl, OMe is methoxy, OEt is ethoxy, SMe is methylthio, SEt is ethylthio, —CN is cyano, —NO$_2$ is nitro, TMS is trimethylsilyl,

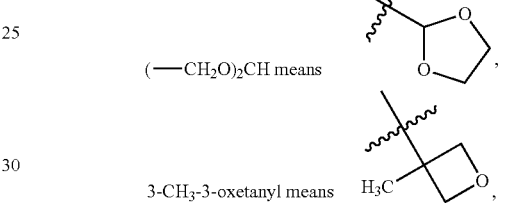

(—CH$_2$O)$_2$CH means

3-CH$_3$-3-oxetanyl means and naphthyl means naphthalenyl. (R) or (S) denotes the absolute chirality of the asymmetric carbon center. The abbreviation "(d)" indicates that the compound appeared to decompose on melting. The abbreviation "Cmpd. No." stands for "Compound Number". The abbreviation "Ex." stands for "Example" and is followed by a number indicating in which example the compound is prepared. Mass spectra are reported with an estimated precision within ±0.5 Da as the molecular weight of the highest isotopic abundance parent ion (M+1) formed by addition of H$^+$ (molecular weight of 1) to the molecule observed by using atmospheric pressure chemical ionization (AP+).

INDEX TABLE A

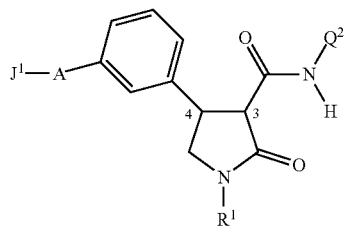

| Cmpd. No. | J$^1$ | A*** | Q$^2$ | R$^1$ | m.p. (° C.) | M − 1 | M + 1 |
|---|---|---|---|---|---|---|---|
| 1 | 2-furanyl | —CH$_2$O— | Ph(2-Cl) | H | | | 411 |
| 2 | 2-furanyl | —CH$_2$O— | Ph(2-CF$_3$) | H | | | 445 |
| 3 | c-Pr—CH$_2$ | —O— | Ph(2,4-di-F) | H | | | 387 |
| 4 | c-Pr—CH$_2$ | —O— | Ph(2-Cl) | H | | | 385 |
| 5 | (—CH$_2$O)$_2$CH | —CH$_2$O— | Ph(2-CF$_3$) | H | 60-64 | | 451 |
| 6 | (—CH$_2$O)$_2$CH | —CH$_2$O— | Ph(2-Cl) | H | 122-126 | | 417 |
| 7 | (—CH$_2$O)$_2$CH | —CH$_2$O— | Ph(2,3-di-F) | H | 140-146 | | 419 |
| 8 | (—CH$_2$O)$_2$CH | —CH$_2$O— | Ph(2-F) | H | 113-116 | | 401 |
| 9 | 2-furanyl | —CH$_2$O— | Ph(2,3-di-F) | H | 138-142 | | 413 |
| 10 | 2-furanyl | —CH$_2$O— | Ph(2-F) | H | | | 395 |

INDEX TABLE A-continued

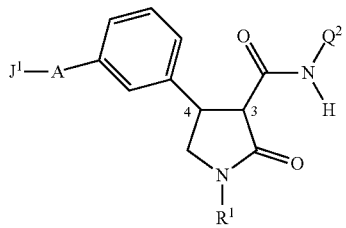

| Cmpd. No. | J[1] | A*** | Q[2] | R[1] | m.p. (° C.) | M − 1 | M + 1 |
|---|---|---|---|---|---|---|---|
| 11 | c-Pr—CH$_2$ | —O— | Ph(2-F) | H | | | 369 |
| 12 | c-Pr—CH$_2$ | —O— | Ph(2,3-di-F) | H | | | 387 |
| 13 | 3-CH$_3$-3-oxetanyl | —CH$_2$O— | Ph(2,3-di-F) | H | | | 415 |
| 14 | 3-CH$_3$-3-oxetanyl | —CH$_2$O— | Ph(2-F) | H | | | 397 |
| 15 | 3-CH$_3$-3-oxetanyl | —CH$_2$O— | Ph(2-CF$_3$) | H | | | 449 |
| 16 | 3-CH$_3$-3-oxetanyl | —CH$_2$O— | Ph(2-Cl) | H | | | 415 |
| 17 | Phenyl | —OCH$_2$— | Ph(2,3,4-tri-F) | H | | | 441 |
| 18 | Phenyl | —OCH$_2$— | Ph(2-Cl) | H | | | 421 |
| 19 | Phenyl | —OCH$_2$— | Ph(2-F) | H | | | 405 |
| 20 | Phenyl | —OCH$_2$— | Ph(2,4-di-F) | H | | | 423 |
| 21 | Phenyl | —OCH$_2$— | Ph(2,3-di-F) | H | | | 423 |
| 22 | 3-CF$_3$-1H-pyrazol-1-yl | —CH$_2$— | Ph(2,3,4-tri-F) | H | | | 483 |
| 23 | 3-CF$_3$-1H-pyrazol-1-yl | —CH$_2$— | Ph(2-F) | H | | | 447 |
| 24 | 3-CF$_3$-1H-pyrazol-1-yl | —CH$_2$— | Ph(2,4-di-F) | H | | | 465 |
| 25 (Ex. 2) | 3-CF$_3$-1H-pyrazol-1-yl | —CH$_2$— | Ph(2,3-di-F) | H | ** | | 465 |
| 26 | 1H-pyrazol-1-yl | —CH$_2$— | Ph(2,3,4-tri-F) | H | | | 415 |
| 27 | 1H-pyrazol-1-yl | —CH$_2$— | Ph(2-F) | H | | | 379 |
| 28 | 1H-pyrazol-1-yl | —CH$_2$— | Ph(2,4-di-F) | H | | | 397 |
| 29 | 1H-pyrazol-1-yl | —CH$_2$— | Ph(2-Cl) | H | | | 395 |
| 30 | 1H-pyrazol-1-yl | —CH$_2$— | Ph(2,3-di-F) | H | | | 397 |
| 31 | 1H-1,2,4-triazol-1-yl | —CH$_2$— | Ph(2-F) | H | | | 380 |
| 32 | 1H-1,2,4-triazol-1-yl | —CH$_2$— | Ph(2,3-di-F) | H | | | 398 |
| 33 | TMS | —C≡C— | Ph(2,3-di-F) | H | | 411 | |
| 34 (Ex. 1) | pyridin-2-yl | —O— | Ph(2-F) | H | * | | |
| 35 | pyridin-2-yl | —O— | Ph(2,4-di-F) | H | | | 428 |
| 36[a] | pyrimidin-2-yl(5-F) | —O— | Ph(2-F) | CH$_3$ | 61-65 | | |
| 37[a] | pyrimidin-2-yl(5-F) | —O— | Ph(2,3-di-F) | H | 174-178 | | |
| 38[a] | pyrimidin-2-yl(5-F) | —O— | Ph(2,3-di-F) | CH$_3$ | 71-75 | | |
| 39[a] | pyrimidin-2-yl(5-F) | —O— | Ph(2-F) | H | 76-79 | | |
| 40 | CF$_3$OCHF— | —CF$_2$O— | Ph(2-F) | H | 129-131 | | |
| 41 | CF$_3$OCHF— | —CF$_2$O— | Ph(2-F) | CH$_3$ | 110-113 | | |
| 42 | pyridin-2-yl | —O— | Ph(2,3,4-tri-F) | H | | | 428 |
| 43[a] | pyridin-2-yl(5-CF$_3$) | —O— | Ph(2-F) | CH$_3$ | 56-60 | | |
| 44[a] | pyridin-2-yl(5-CF$_3$) | —O— | Ph(2,3-di-F) | CH$_3$ | 64-68 | | |
| 45[a] | Ph(4-F) | —O— | Ph(2-F) | CH$_3$ | | | 423 |
| 46[a] | Ph(4-F) | —O— | Ph(2,3-di-F) | CH$_3$ | | | 441 |
| 47[a] | pyridin-2-yl(5-CF$_3$) | —O— | Ph(2,3-di-F) | H | 76-79 | | |
| 48 | CF$_3$OCHF— | —CF$_2$O— | Ph(2,3-di-F) | CH$_3$ | | | 513 |
| 49[a] | pyridin-2-yl(5-F) | —O— | Ph(2-F) | H | 140-144 | | |
| 50[a] | Phenyl | —S— | Ph(2-F) | CH$_3$ | | | 421 |
| 51[a] | Phenyl | —S— | Ph(2,3-di-F) | CH$_3$ | | | 439 |
| 52[a] | pyridin-2-yl(5-F) | —O— | Ph(2,3-di-F) | H | 185-190 | | |
| 55 | pyrimidin-2-yl(5-Cl) | —O— | Ph(2-F) | H | | | 427 |
| 56 | pyrimidin-2-yl(5-Cl) | —O— | Ph(2,3-di-F) | H | | | 445 |
| 60[a] | pyridin-2-yl(5-F) | —O— | Ph(2-F) | CH$_3$ | | | 424 |
| 61[a] | pyridin-2-yl(5-F) | —O— | Ph(2,3-di-F) | CH$_3$ | | | 442 |
| 62[a] | pyridin-2-yl(5-CF$_3$) | —O— | Ph(2-F) | H | 67-70 | | |
| 63 | Phenyl | —CH$_2$O— | Ph(2-F) | H | | | 405 |
| 64 | Phenyl | —CH$_2$O— | Ph(2,4-di-F) | H | | | 423 |
| 65 | Phenyl | —CH$_2$O— | Ph(2,3-di-F) | H | | | 423 |
| 66 | Phenyl | —CH$_2$O— | Ph(2,3,4-tri-F) | H | | | 441 |
| 67 | Phenyl | —CH$_2$O— | Ph(2-Cl) | H | | | 421 |
| 68 | pyridin-2-yl | —O— | Ph(2,3-di-F) | H | | 408 | |
| 69 | pyridin-2-yl | —O— | Ph(2-Cl) | H | | | 408 |
| 70[a] | Phenyl | —CH=CH— | Ph(2,3-di-F) | H | 150-153 | | |
| 71[a] | pyridin-2-yl(3,5-di-F) | —O— | Ph(2,3-di-F) | H | | | 446 |
| 72[a] | pyridin-2-yl(3,5-di-F) | —O— | Ph(2-F) | CH$_3$ | | | 442 |
| 73[a] | pyridin-2-yl(3,5-di-F) | —O— | Ph(2,3-di-F) | CH$_3$ | | | 460 |
| 74[a] | pyridin-2-yl(3,5-di-F) | —O— | Ph(2,3,4-tri-F) | CH$_3$ | | | 478 |
| 75[a] | Phenyl | —CH=CH— | Ph(2-F) | CH$_3$ | | | 415 |
| 76[a] | Phenyl | —CH=CH— | Ph(2,3-di-F) | CH$_3$ | | | 433 |
| 77[a] | Phenyl | —CH$_2$CH$_2$— | Ph(2,3-di-F) | CH$_3$ | | | 435 |
| 78[a] | Phenyl | —CH$_2$CH$_2$— | Ph(2,3-di-F) | H | | | 421 |
| 79[a] | Phenyl | —CH=CH— | Ph(2-SCH$_3$) | CH$_3$ | 171-175 | | |
| 80[a] | pyrimidin-2-yl(5-CH$_3$) | —O— | Ph(2,3-di-F) | H | | | 425 |
| 81[a] | pyrimidin-2-yl(5-CH$_3$) | —O— | Ph(2-F) | CH$_3$ | 71-72 | | |

INDEX TABLE A-continued

| Cmpd. No. | J¹ | A*** | Q² | R¹ | m.p. (° C.) | M − 1 | M + 1 |
|---|---|---|---|---|---|---|---|
| 82[a] | pyrimidin-2-yl(5-CH₃) | —O— | Ph(2,3-di-F) | CH₃ | 70-71 | | |
| 83[a] | pyrimidin-2-yl(5-CH₃) | —O— | Ph(2,3,4-tri-F) | CH₃ | | | 457 |
| 87[a] (Ex. 4) | pyridin-2-yl(5-F) | —O— | Ph(2,3,4-tri-F) | CH₃ | | | 460 |
| 88[a] | pyridin-2-yl(5-F) | —O— | Ph(3-CN,2-F) | CH₃ | | | 449 |
| 89[a] | pyridin-2-yl(5-F) | —O— | Ph(2-CN,3-F) | CH₃ | | | 449 |
| 90[a] | N-morpholinyl | —CH₂— | Ph(2,3-di-F) | H | | | 416 |
| 91[a] | Phenyl | —NH— | Ph(2,3,4-tri-F) | CH₃ | | | 440 |
| 92[a] | thiazol-2-yl | —O— | Ph(2-F) | CH₃ | | | 412 |
| 93[a] | thiazol-2-yl | —O— | Ph(2,3-di-F) | CH₃ | | | 430 |
| 94[a] | thiazol-2-yl | —O— | Ph(2,3,4-tri-F) | CH₃ | | | 448 |

\* See Synthesis Example 1 for ¹H NMR data.
\*\* See Synthesis Example 2 for ¹H NMR data.
\*\*\* The free bond projecting to the right indicates the connecting point of A to Q¹ (i.e. phenyl) and the free bond projecting to the left indicates the connecting point of A to J¹.
[a] Indicates the compound is prepared enantio-enriched at the 3- and 4-positions.

INDEX TABLE B

| Cmpd. No. | T | Q² | R¹ | m.p. (° C.) |
|---|---|---|---|---|
| 53 (Ex. 3) | —CH=N—OCH₃ | Ph(2-F) | CH₃ | 113-117 |
| 54 | —CH=N—N(CH₃)₂ | Ph(2-F) | CH₃ | 107-110 |

INDEX TABLE C

| Cmpd. No. | J¹ | A | Q² | m.p. (° C.) |
|---|---|---|---|---|
| 57 | 3-CF₃-1H-pyrazol-1-yl | —CH₂— | Ph(2,3-di-F) | 170-174 |
| 58 | 3-CF₃-1H-pyrazol-1-yl | —CH₂— | Ph(2,3,4-tri-F) | 127-130 |
| 59 | 3-CF₃-1H-pyrazol-1-yl | —CH₂— | Ph(2-F) | 130-134 |

INDEX TABLE D

| Cmpd. No. | J¹ | A | Q² | m.p. (° C.) |
|---|---|---|---|---|
| 84[a] | pyrimidin-2-yl(5-F) | —O— | Ph(2-F) | 71-72 |
| 85[a] | pyrimidin-2-yl(5-F) | —O— | Ph(2,3-di-F) | 70-71 |
| 86[a] | pyrimidin-2-yl(5-F) | —O— | Ph(3-Cl,2-F) | 65-66 |

[a] Indicates the compound is prepared enantio-enriched at the 3- and 4-positions.

BIOLOGICAL EXAMPLES OF THE INVENTION

Test A Seeds of plant species selected from barnyardgrass (*Echinochloa crus-galli*), kochia (*Kochia scoparia*), ragweed (common ragweed, *Ambrosia elatior*), ryegrass, Italian (*Lolium multiflorum*), foxtail, giant (*Setaria faberii*), and pigweed (*Amaranthus retroflexus*), were planted into a blend of loam soil and sand and treated preemergence with a directed soil spray using test chemicals formulated in a non-phytotoxic solvent mixture which included a surfactant.

At the same time, plants selected from these weed species and also blackgrass (*Alopecurus myosuroides*), galium (catchweed bedstraw, *Galium aparine*), wheat (*Triticum aestivum*), and corn (*Zea mays*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 500 g ai/ha | Compounds ||||||||||||||
| --- | --- | --- | --- | --- | --- | --- | --- | --- | --- | --- | --- | --- | --- | --- |
| | 1 | 2 | 3 | 4 | 5 | 6 | 7 | 8 | 9 | 10 | 11 | 12 | 13 | 14 |
| Postemergence |||||||||||||||
| Barnyardgrass | 0 | 0 | 60 | 80 | 20 | 70 | 70 | 70 | 60 | 60 | 90 | 90 | 60 | 60 |
| Blackgrass | 0 | 0 | 30 | 40 | 0 | 20 | 40 | 20 | 0 | 0 | 40 | 60 | 20 | 0 |
| Corn | 0 | 0 | 20 | 0 | 0 | 20 | 20 | 20 | 20 | 0 | 20 | 60 | 0 | 0 |
| Foxtail, Giant | 0 | 10 | 70 | 80 | 50 | 70 | 70 | 70 | 50 | 30 | 90 | 90 | 70 | 70 |
| Galium | 0 | 0 | 40 | 0 | 0 | 0 | 40 | 0 | 0 | 0 | 30 | 50 | 40 | 0 |
| Kochia | 0 | 0 | 40 | 0 | 0 | 0 | 0 | 0 | 0 | 0 | 0 | 20 | 20 | 0 |
| Pigweed | 0 | 0 | 0 | 30 | 0 | 0 | 0 | 0 | 0 | 0 | 20 | 20 | 0 | 0 |
| Ragweed | 30 | 0 | 0 | 40 | 0 | 0 | 20 | 10 | 0 | 0 | 40 | 30 | 0 | 0 |
| Ryegrass, Italian | 0 | 10 | 30 | 40 | 20 | 0 | 20 | 0 | 0 | 0 | 20 | 50 | 30 | 0 |
| Wheat | 0 | 0 | 20 | 0 | 0 | 20 | 40 | 0 | 0 | 0 | 20 | 50 | 0 | 0 |

| 500 g ai/ha | Compounds ||||||||||||||
| --- | --- | --- | --- | --- | --- | --- | --- | --- | --- | --- | --- | --- | --- |
| | 15 | 16 | 17 | 18 | 19 | 20 | 21 | 22 | 23 | 24 | 25 | 26 | 27 | 28 |
| Postemergence ||||||||||||||
| Barnyardgrass | 0 | 50 | 40 | 20 | 50 | 70 | 20 | 60 | 30 | 0 | 60 | 70 | 70 | 20 |
| Blackgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Foxtail, Giant | 20 | 20 | 40 | 0 | 40 | 60 | 30 | 60 | 20 | 0 | 60 | 60 | 50 | 20 |
| Galium | 0 | 0 | 30 | 0 | 0 | 0 | 0 | 0 | 0 | 0 | 0 | 0 | 0 | 0 |
| Kochia | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 |
| Ragweed | 30 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 |

| 500 g ai/ha | Compounds |||||||||||||
| --- | --- | --- | --- | --- | --- | --- | --- | --- | --- | --- | --- | --- | --- |
| | 29 | 30 | 31 | 32 | 33 | 34 | 35 | 36 | 37 | 38 | 39 | 40 | 41 | 42 |
| Postemergence |||||||||||||
| Barnyardgrass | 20 | 60 | 0 | 10 | 50 | 60 | 60 | 90 | 100 | 100 | 100 | 40 | 50 | 60 |
| Blackgrass | 0 | 0 | 0 | 0 | 0 | 20 | 0 | 50 | 70 | 70 | 40 | 30 | 30 | 0 |
| Corn | 0 | 0 | 0 | 0 | 0 | 0 | 0 | 90 | 90 | 100 | 70 | 0 | 40 | 0 |
| Foxtail, Giant | 20 | 50 | 0 | 20 | 50 | 80 | 70 | 80 | 90 | 90 | 80 | 60 | 70 | 70 |
| Galium | 0 | 0 | 20 | 40 | 20 | 50 | 0 | 70 | 70 | 70 | 30 | 40 | 60 | 30 |
| Kochia | 0 | 0 | 0 | 0 | 40 | 0 | 0 | 50 | 50 | 60 | 0 | 0 | 60 | 0 |
| Pigweed | 0 | 0 | 0 | 0 | 0 | 0 | 0 | 50 | 70 | 70 | 20 | 0 | 80 | 0 |
| Ragweed | 0 | 0 | 0 | 0 | 0 | 0 | 0 | 40 | 70 | 80 | 30 | 0 | 0 | 0 |
| Ryegrass, Italian | 0 | 0 | 0 | 0 | 0 | 30 | 30 | 50 | 60 | 80 | 20 | 0 | 20 | 0 |
| Wheat | 0 | 0 | 0 | 0 | 0 | 0 | 0 | 60 | 70 | 70 | 60 | 20 | 40 | 0 |

| 500 g ai/ha | Compounds ||||||||||||
| --- | --- | --- | --- | --- | --- | --- | --- | --- | --- | --- | --- | --- |
| | 43 | 44 | 45 | 46 | 47 | 48 | 49 | 50 | 51 | 52 | 53 | 54 | 55 | 56 |
| Postemergence ||||||||||||
| Barnyardgrass | 90 | 90 | 90 | 90 | 90 | 50 | 90 | 30 | 30 | 80 | 90 | 30 | 80 | 30 |
| Blackgrass | 50 | 50 | 30 | 30 | 20 | 0 | 40 | 0 | 0 | 40 | 20 | 0 | 0 | 0 |
| Corn | 80 | 80 | 50 | 50 | 80 | 40 | 40 | 20 | 30 | 70 | 0 | 0 | 0 | 0 |
| Foxtail, Giant | 80 | 80 | 80 | 80 | 80 | 80 | 90 | 70 | 40 | 90 | 90 | 20 | 80 | 60 |
| Galium | 80 | 80 | 60 | 70 | 70 | 60 | 70 | 40 | 50 | 60 | 30 | 0 | 30 | 20 |
| Kochia | 60 | 60 | 60 | 60 | 60 | 70 | 0 | — | 30 | — | 0 | 0 | 0 | 0 |
| Pigweed | 50 | 80 | 60 | 70 | 70 | 90 | 20 | 30 | 0 | 60 | 0 | 0 | 0 | 0 |
| Ragweed | 0 | 0 | 0 | 0 | 0 | 0 | 40 | 0 | 20 | 60 | 0 | 0 | 0 | 0 |
| Ryegrass, Italian | 30 | 30 | 30 | 30 | 30 | 40 | 50 | 0 | 30 | 60 | 0 | 0 | 30 | 0 |
| Wheat | 50 | 50 | 20 | 20 | 30 | 30 | 40 | 0 | 20 | 40 | 0 | 0 | 0 | 0 |

TABLE A-continued

| 500 g ai/ha | Compounds | | | | | | | | | | | | |
|---|---|---|---|---|---|---|---|---|---|---|---|---|---|
| | 57 | 58 | 59 | 60 | 61 | 62 | 63 | 64 | 65 | 66 | 67 | 68 | 69 |
| | Postemergence | | | | | | | | | | | | |
| Barnyardgrass | 60 | 60 | 30 | 90 | 80 | 90 | 0 | 0 | 0 | 0 | 0 | 40 | 20 |
| Blackgrass | 30 | 0 | 0 | 30 | 50 | 30 | 0 | 0 | 0 | 0 | 0 | 20 | 0 |
| Corn | 30 | 0 | 0 | 50 | 90 | 30 | 0 | 0 | 0 | 0 | 0 | 0 | 0 |
| Foxtail, Giant | 70 | 60 | 20 | 90 | 90 | 90 | 0 | 0 | 0 | 0 | 0 | 60 | 30 |
| Galium | 20 | 20 | 0 | 60 | 70 | 60 | 0 | 0 | 0 | 0 | 0 | 0 | 0 |
| Kochia | 20 | 20 | 0 | — | — | — | 0 | 0 | 0 | 0 | 0 | 0 | 0 |
| Pigweed | 20 | 0 | 0 | 40 | 70 | 30 | 0 | 0 | 0 | 0 | 0 | 0 | 0 |
| Ragweed | 30 | 0 | 0 | 40 | 50 | 40 | 0 | 0 | 0 | 0 | 0 | 0 | 0 |
| Ryegrass, Italian | 0 | 0 | 0 | 50 | 70 | 30 | 0 | 0 | 0 | 0 | 0 | 0 | 0 |
| Wheat | 0 | 0 | 0 | 70 | 80 | 30 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| | Postemergence | | | | | | | | | | | | |
| Barnyardgrass | 0 | 0 | 10 | 40 | 0 | 0 | 40 | 0 | 30 | 10 | 50 | 70 | 0 | 10 |
| Blackgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Foxtail, Giant | 0 | 0 | 20 | 40 | 20 | 0 | 20 | 0 | 0 | 0 | 50 | 70 | 40 | 10 |
| Galium | 0 | 0 | 20 | 0 | 0 | 0 | 20 | 0 | 0 | 0 | 0 | 0 | 0 | 0 |
| Kochia | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 30 | 30 | 0 | 0 | 0 |
| Ryegrass, Italian | 0 | 0 | 0 | 0 | 20 | 0 | 0 | 0 | 0 | 0 | 0 | 20 | 0 | 0 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| | Postemergence | | | | | | | | | | | | |
| Barnyardgrass | 0 | 0 | 30 | 0 | 20 | 40 | 20 | 40 | 0 | 0 | 20 | 30 | 40 | 0 |
| Blackgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Foxtail, Giant | 10 | 0 | 30 | 0 | 20 | 40 | 30 | 20 | 0 | 0 | 20 | 30 | 40 | 0 |
| Galium | 0 | 0 | 50 | 0 | 0 | 0 | 0 | 0 | 0 | 0 | 0 | 0 | 0 | 0 |
| Kochia | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| | 29 | 30 | 31 | 32 | 33 | 34 | 35 | 36 | 37 | 38 | 39 | 40 | 41 | 42 |
| | Postemergence | | | | | | | | | | | | |
| Barnyardgrass | 0 | 20 | 0 | 0 | 0 | 30 | 30 | 90 | 90 | 100 | 70 | 50 | 50 | 40 |
| Blackgrass | 0 | 0 | 0 | 0 | 0 | 0 | 0 | 20 | 40 | 70 | 0 | 0 | 0 | 0 |
| Corn | 0 | 0 | 0 | 0 | 0 | 0 | 0 | 40 | 70 | 90 | 30 | 0 | 0 | 0 |
| Foxtail, Giant | 0 | 30 | 0 | 0 | 0 | 30 | 30 | 80 | 70 | 90 | 70 | 40 | 50 | 50 |
| Galium | 0 | 0 | 0 | 0 | 0 | 20 | 0 | 40 | 50 | 50 | 0 | 40 | 40 | 0 |
| Kochia | 0 | 0 | 0 | 0 | 0 | 0 | 0 | 0 | 0 | 30 | 0 | 0 | 20 | 0 |
| Pigweed | 0 | 0 | 0 | 0 | 0 | 0 | 0 | 30 | 40 | 50 | 0 | 0 | 40 | 0 |
| Ragweed | 0 | 0 | 0 | 0 | 0 | 0 | 0 | 0 | 20 | 20 | 0 | 0 | 0 | 0 |
| Ryegrass, Italian | 0 | 0 | 0 | 0 | 0 | 0 | 0 | 0 | 0 | 70 | 0 | 0 | 0 | 0 |
| Wheat | 0 | 0 | 0 | 0 | 0 | 0 | 0 | 0 | 20 | 50 | 0 | 0 | 0 | 0 |

| 125 g ai/ha | Compounds | | | | | | | | | | | | |
|---|---|---|---|---|---|---|---|---|---|---|---|---|---|
| | 43 | 44 | 45 | 46 | 47 | 48 | 49 | 50 | 51 | 52 | 53 | 54 | 55 | 56 |
| | Postemergence | | | | | | | | | | | | |
| Barnyardgrass | 90 | 90 | 90 | 90 | 70 | 20 | 80 | 0 | 0 | 70 | 70 | 0 | 30 | 0 |
| Blackgrass | 30 | 30 | 30 | 0 | 0 | 0 | 0 | 0 | 0 | 30 | 0 | 0 | 0 | 0 |
| Corn | 40 | 40 | 0 | 40 | 20 | 0 | 30 | 0 | 0 | 50 | 0 | 0 | 0 | 0 |
| Foxtail, Giant | 80 | 70 | 80 | 70 | 60 | 60 | 70 | 50 | 10 | 70 | 80 | 0 | 70 | 0 |
| Galium | 70 | 70 | 60 | 60 | 60 | 60 | 20 | 0 | 40 | 40 | 0 | 0 | 0 | 0 |
| Kochia | 40 | 30 | 40 | 40 | 0 | 30 | 0 | — | 0 | — | 0 | 0 | 0 | 0 |

TABLE A-continued

| | | | | | | | | | | | | | | |
|---|---|---|---|---|---|---|---|---|---|---|---|---|---|---|
| Pigweed | 30 | 50 | 30 | 50 | 60 | 60 | 0 | 0 | 0 | 40 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 20 | 30 | 0 | 0 | 0 | 0 |
| Wheat | 30 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 57 | 58 | 59 | 60 | 61 | 62 | 63 | 64 | 65 | 66 | 67 | 68 | 69 | 71 |

Postemergence

| | | | | | | | | | | | | | | |
|---|---|---|---|---|---|---|---|---|---|---|---|---|---|---|
| Barnyardgrass | 0 | 0 | 0 | 70 | 70 | 70 | 0 | 0 | 0 | 0 | 0 | 10 | 0 | 70 |
| Blackgrass | 0 | 0 | 0 | 0 | 40 | 0 | 0 | 0 | 0 | 0 | 0 | 0 | 0 | 0 |
| Corn | 30 | 0 | 0 | 30 | 70 | 30 | 0 | 0 | 0 | 0 | 0 | 0 | 0 | 20 |
| Foxtail, Giant | 40 | 30 | 0 | 80 | 90 | 80 | 0 | 0 | 0 | 0 | 0 | 0 | 0 | 70 |
| Galium | 0 | 0 | 0 | 30 | 60 | 30 | 0 | 0 | 0 | 0 | 0 | 0 | 0 | 50 |
| Kochia | 0 | 0 | 0 | — | — | — | 0 | 0 | 0 | 0 | 0 | 0 | 0 | 20 |
| Pigweed | 0 | 0 | 0 | 0 | 40 | 0 | 0 | 0 | 0 | 0 | 0 | 0 | 0 | 50 |
| Ragweed | 0 | 0 | 0 | 0 | 40 | 0 | 0 | 0 | 0 | 0 | 0 | 0 | 0 | 30 |
| Ryegrass, Italian | 0 | 0 | 0 | 30 | 70 | 0 | 0 | 0 | 0 | 0 | 0 | 0 | 0 | 0 |
| Wheat | 0 | 0 | 0 | 0 | 50 | 0 | 0 | 0 | 0 | 0 | 0 | 0 | 0 | 0 |

| | Compounds | | | | | | |
|---|---|---|---|---|---|---|---|
| 125 g ai/ha | 72 | 73 | 74 | 87 | 88 | 89 | 90 |

Postemergence

| | | | | | | | |
|---|---|---|---|---|---|---|---|
| Barnyardgrass | 90 | 70 | 90 | 80 | 80 | 70 | 0 |
| Blackgrass | 60 | 40 | 20 | 60 | 0 | 20 | 0 |
| Corn | 20 | 20 | 20 | 90 | 20 | 0 | 0 |
| Foxtail, Giant | 90 | 90 | 80 | 80 | 70 | 70 | 0 |
| Galium | 60 | 60 | 70 | 60 | 40 | 40 | 0 |
| Kochia | 20 | 20 | 50 | 30 | 30 | 0 | 0 |
| Pigweed | 30 | 60 | 60 | 70 | 20 | 50 | 0 |
| Ragweed | 30 | 30 | 20 | 0 | 0 | 0 | 0 |
| Ryegrass, Italian | 50 | 40 | 30 | 70 | 0 | 20 | 0 |
| Wheat | 20 | 20 | 20 | 40 | 60 | 0 | 0 |

| | Compounds | | | | | | | |
|---|---|---|---|---|---|---|---|---|
| 31 g ai/ha | 71 | 72 | 73 | 74 | 87 | 88 | 89 | 90 |

Postemergence

| | | | | | | | | |
|---|---|---|---|---|---|---|---|---|
| Barnyardgrass | 30 | 60 | 60 | 60 | 50 | 30 | 30 | 0 |
| Blackgrass | 0 | 20 | 0 | 0 | 30 | 0 | 0 | 0 |
| Corn | 0 | 0 | 20 | 0 | 60 | 0 | 0 | 0 |
| Foxtail, Giant | 20 | 80 | 60 | 70 | 70 | 30 | 30 | 0 |
| Galium | 30 | 40 | 50 | 40 | 30 | 30 | 30 | 0 |
| Kochia | 0 | 0 | 0 | 20 | 0 | 0 | 0 | 0 |
| Pigweed | 0 | 0 | 50 | 0 | 0 | 0 | 0 | 0 |
| Ragweed | 0 | 0 | 0 | 0 | 0 | 0 | 0 | 0 |
| Ryegrass, Italian | 0 | 20 | 0 | 0 | 40 | 0 | 0 | 0 |
| Wheat | 0 | 0 | 20 | 0 | 0 | 0 | 0 | 0 |

| | Compounds | | | | | | | | | | | | | |
|---|---|---|---|---|---|---|---|---|---|---|---|---|---|---|
| 500 g ai/ha | 1 | 2 | 3 | 4 | 5 | 6 | 7 | 8 | 9 | 10 | 11 | 12 | 13 | 14 |

Preemergence

| | | | | | | | | | | | | | | |
|---|---|---|---|---|---|---|---|---|---|---|---|---|---|---|
| Barnyardgrass | 0 | 30 | 70 | 90 | 50 | 80 | 90 | 80 | 70 | 0 | 90 | 90 | 80 | 80 |
| Foxtail, Giant | 0 | 20 | 80 | 90 | 90 | 90 | 90 | 90 | 70 | 0 | 90 | 90 | 90 | 90 |
| Kochia | 0 | 0 | 20 | 30 | 0 | 0 | 0 | 0 | 0 | 0 | 40 | 40 | 0 | 0 |
| Pigweed | 0 | 0 | 0 | 20 | 30 | 50 | 60 | 0 | 0 | 0 | 30 | 30 | 0 | 0 |
| Ragweed | 0 | 0 | 0 | 0 | 0 | 20 | 0 | 0 | 0 | 0 | 0 | 0 | 0 | 0 |
| Ryegrass, Italian | 0 | 0 | 20 | 20 | 0 | 0 | 30 | 0 | 0 | 0 | 20 | 20 | 0 | 0 |

| | Compounds | | | | | | | | | | | | | |
|---|---|---|---|---|---|---|---|---|---|---|---|---|---|---|
| 500 g ai/ha | 15 | 16 | 17 | 18 | 19 | 20 | 21 | 22 | 23 | 24 | 25 | 26 | 27 | 28 |

Preemergence

| | | | | | | | | | | | | | | |
|---|---|---|---|---|---|---|---|---|---|---|---|---|---|---|
| Barnyardgrass | 60 | 60 | 70 | 0 | 70 | 70 | 40 | 30 | 20 | 0 | 40 | 90 | 20 | 30 |
| Foxtail, Giant | 40 | 70 | 80 | 20 | 80 | 80 | 60 | 80 | 50 | 0 | 80 | 90 | 30 | 30 |
| Kochia | 0 | 0 | 30 | 0 | 40 | 30 | 20 | 0 | 20 | 0 | 20 | 0 | 0 | 0 |
| Pigweed | 0 | 0 | 0 | 0 | 0 | 0 | 0 | 0 | 0 | 0 | 0 | 0 | 0 | 0 |

TABLE A-continued

| | | | | | | | | | | | | | | |
|---|---|---|---|---|---|---|---|---|---|---|---|---|---|---|
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 500 g ai/ha | 29 | 30 | 31 | 32 | 33 | 34 | 35 | 36 | 37 | 38 | 39 | 40 | 41 | 42 |
| | Preemergence | | | | | | | | | | | | | |
| Barnyardgrass | 40 | 50 | 0 | 0 | 80 | 90 | 60 | 90 | 90 | 100 | 90 | 90 | 90 | 80 |
| Foxtail, Giant | 40 | 90 | 0 | 40 | 80 | 90 | 90 | 90 | 100 | 100 | 100 | 90 | 90 | 90 |
| Kochia | 0 | 0 | 0 | 0 | 0 | 0 | 0 | 40 | 70 | 70 | 50 | 90 | 60 | 0 |
| Pigweed | 0 | 0 | 0 | 0 | 0 | 0 | 0 | 40 | 80 | 100 | 0 | 0 | 90 | 10 |
| Ragweed | 0 | 0 | 0 | 0 | 0 | 0 | 0 | 50 | 80 | 80 | 50 | 20 | 70 | 0 |
| Ryegrass, Italian | 0 | 0 | 0 | 0 | 0 | 0 | 0 | 90 | 50 | 100 | 60 | 0 | 60 | 0 |

| | Compounds | | | | | | | | | | | | | |
|---|---|---|---|---|---|---|---|---|---|---|---|---|---|---|
| 500 g ai/ha | 43 | 44 | 45 | 46 | 47 | 48 | 49 | 50 | 51 | 52 | 53 | 54 | 55 | 56 |
| | Preemergence | | | | | | | | | | | | | |
| Barnyardgrass | 80 | 80 | 80 | 80 | 80 | 90 | 90 | 40 | — | 90 | 90 | 20 | 80 | 70 |
| Foxtail, Giant | 90 | 90 | 90 | 90 | 90 | 90 | 90 | 90 | 90 | 90 | 90 | 70 | 90 | 0 |
| Kochia | 30 | 0 | 20 | 20 | 0 | 20 | 70 | 30 | 50 | 80 | 70 | 0 | 20 | 0 |
| Pigweed | 80 | 80 | 70 | 70 | 50 | 70 | 20 | 20 | 0 | 70 | 0 | 0 | 0 | 0 |
| Ragweed | 80 | 60 | 30 | 30 | 60 | 0 | 40 | 30 | 0 | 80 | 0 | 0 | 0 | 0 |
| Ryegrass, Italian | 80 | 90 | 80 | 80 | 70 | 30 | 70 | 0 | 20 | 40 | 0 | 0 | 20 | 0 |

| | Compounds | | | | | | | | | | | | |
|---|---|---|---|---|---|---|---|---|---|---|---|---|---|
| 500 g ai/ha | 57 | 58 | 59 | 60 | 61 | 62 | 63 | 64 | 65 | 66 | 67 | 68 | 69 |
| | Preemergence | | | | | | | | | | | | |
| Barnyardgrass | 90 | 90 | 40 | 90 | 90 | 90 | 0 | 0 | 0 | 0 | 0 | 50 | 0 |
| Foxtail, Giant | 90 | 90 | 50 | 90 | 90 | 90 | 0 | 0 | 0 | 0 | 0 | 90 | 50 |
| Kochia | 0 | — | 0 | 80 | 80 | 60 | 0 | 0 | 0 | 0 | 0 | 0 | 0 |
| Pigweed | 0 | 0 | 0 | 50 | 90 | 50 | 0 | 0 | 0 | 0 | 0 | 0 | 0 |
| Ragweed | 0 | 0 | 0 | 50 | 60 | 50 | 0 | 0 | 0 | 0 | 0 | 0 | 0 |
| Ryegrass, Italian | 0 | 20 | 0 | 70 | 90 | 20 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 1 | 2 | 3 | 4 | 5 | 6 | 7 | 8 | 9 | 10 | 11 | 12 | 13 | 14 |
| | Preemergence | | | | | | | | | | | | | |
| Barnyardgrass | 0 | 0 | 40 | 60 | 0 | 20 | 60 | 50 | 10 | 0 | 60 | 90 | 0 | 10 |
| Foxtail, Giant | 0 | 0 | 60 | 70 | 30 | 70 | 90 | 80 | 10 | 0 | 80 | 90 | 80 | 30 |
| Kochia | 0 | 0 | 0 | 0 | 0 | 0 | 0 | 0 | 0 | 0 | 0 | 0 | 0 | 0 |
| Pigweed | 0 | 0 | 0 | 0 | 0 | 60 | 60 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 30 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 15 | 16 | 17 | 18 | 19 | 20 | 21 | 22 | 23 | 24 | 25 | 26 | 27 | 28 |
| | Preemergence | | | | | | | | | | | | | |
| Barnyardgrass | 0 | 0 | 20 | 0 | 30 | 20 | 0 | 0 | 0 | 0 | 20 | 40 | 0 | 0 |
| Foxtail, Giant | 10 | 10 | 50 | 0 | 30 | 30 | 20 | 40 | 20 | 0 | 50 | 40 | 20 | 0 |
| Kochia | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 29 | 30 | 31 | 32 | 33 | 34 | 35 | 36 | 37 | 38 | 39 | 40 | 41 | 42 |
| | Preemergence | | | | | | | | | | | | | |
| Barnyardgrass | 0 | 0 | 0 | 0 | 60 | 20 | 20 | 90 | 90 | 90 | 70 | 50 | 20 | 40 |
| Foxtail, Giant | 0 | 20 | 0 | 0 | 60 | 70 | 70 | 90 | 90 | 100 | 90 | 90 | 80 | 80 |
| Kochia | 0 | 0 | 0 | 0 | 0 | 0 | 0 | 0 | 30 | 30 | 0 | 30 | 0 | 0 |
| Pigweed | 0 | 0 | 0 | 0 | 0 | 0 | 0 | 0 | 60 | 80 | 0 | 0 | 70 | 0 |
| Ragweed | 0 | 0 | 0 | 0 | 0 | 0 | 0 | 0 | 0 | 40 | 0 | 0 | 20 | 0 |
| Ryegrass, Italian | 0 | 0 | 0 | 0 | 0 | 0 | 0 | 0 | 20 | 80 | 0 | 0 | 20 | 0 |

TABLE A-continued

| 125 g ai/ha | Compounds | | | | | | | | | | | | | |
|---|---|---|---|---|---|---|---|---|---|---|---|---|---|---|
| | 43 | 44 | 45 | 46 | 47 | 48 | 49 | 50 | 51 | 52 | 53 | 54 | 55 | 56 |
| Preemergence | | | | | | | | | | | | | | |
| Barnyardgrass | 80 | 80 | 80 | 70 | 50 | 80 | 90 | 0 | 20 | 70 | 90 | 0 | 0 | 30 |
| Foxtail, Giant | 90 | 90 | 90 | 90 | 90 | 80 | 90 | 90 | 90 | 90 | 90 | 0 | 80 | 0 |
| Kochia | 30 | 0 | 0 | 0 | 0 | 0 | 20 | 0 | 20 | 70 | 60 | 0 | 0 | 0 |
| Pigweed | 40 | 30 | 40 | 40 | 0 | 70 | 0 | 20 | 0 | 60 | 0 | 0 | 0 | 0 |
| Ragweed | 0 | 0 | 0 | 0 | 0 | 0 | 0 | 0 | 0 | 40 | 0 | 0 | 0 | 0 |
| Ryegrass, Italian | 30 | 30 | 30 | 20 | 0 | 30 | 40 | 0 | 0 | 30 | 0 | 0 | 0 | 0 |

| 125 g ai/ha | Compounds | | | | | | | | | | | | | |
|---|---|---|---|---|---|---|---|---|---|---|---|---|---|---|
| | 57 | 58 | 59 | 60 | 61 | 62 | 63 | 64 | 65 | 66 | 67 | 68 | 69 | 71 |
| Preemergence | | | | | | | | | | | | | | |
| Barnyardgrass | 40 | 30 | 0 | 90 | 90 | 90 | 0 | 0 | 0 | 0 | 0 | 20 | 0 | 70 |
| Foxtail, Giant | 60 | 60 | 0 | 90 | 90 | 90 | 0 | 0 | 0 | 0 | 0 | 60 | 0 | 90 |
| Kochia | — | 0 | 0 | 70 | 60 | 30 | 0 | 0 | 0 | 0 | 0 | 0 | 0 | 30 |
| Pigweed | 0 | 0 | 0 | 60 | 70 | 30 | 0 | 0 | 0 | 0 | 0 | 0 | 0 | 80 |
| Ragweed | 0 | 0 | 0 | 40 | 30 | 0 | 0 | 0 | 0 | 0 | 0 | 0 | 0 | 0 |
| Ryegrass, Italian | 0 | 0 | 0 | 20 | 80 | 0 | 0 | 0 | 0 | 0 | 0 | 0 | 0 | 0 |

| 125 g ai/ha | Compounds | | | | | | |
|---|---|---|---|---|---|---|---|
| | 72 | 73 | 74 | 87 | 88 | 89 | 90 |
| Preemergence | | | | | | | |
| Barnyardgrass | 90 | 90 | 90 | 90 | 30 | 70 | 0 |
| Foxtail, Giant | 90 | 90 | 100 | 90 | 90 | 90 | 0 |
| Kochia | 0 | 20 | 40 | 60 | 30 | 0 | 0 |
| Pigweed | 0 | 0 | 80 | 70 | 20 | 60 | 0 |
| Ragweed | 0 | 0 | 0 | 0 | 0 | 0 | 0 |
| Ryegrass, Italian | 50 | 40 | 80 | 80 | 20 | 40 | 0 |

| 31 g ai/ha | Compounds | | | | | | |
|---|---|---|---|---|---|---|---|
| | 71 | 72 | 73 | 74 | 87 | 88 | 89 | 90 |
| Preemergence | | | | | | | |
| Barnyardgrass | 0 | 90 | 50 | 70 | 60 | 0 | 30 | 0 |
| Foxtail, Giant | 70 | 90 | 80 | 90 | 90 | 30 | 40 | 0 |
| Kochia | 0 | 0 | 0 | 0 | 0 | 0 | 0 | 0 |
| Pigweed | 20 | 0 | 0 | 0 | 70 | 0 | 0 | 0 |
| Ragweed | 0 | 0 | 0 | 0 | 0 | 0 | 0 | 0 |
| Ryegrass, Italian | 0 | 0 | 0 | 30 | 0 | 0 | 0 | 0 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| 500 g ai/ha | Compounds | | | | | | | | | | | | | |
|---|---|---|---|---|---|---|---|---|---|---|---|---|---|---|
| | 22 | 23 | 24 | 25 | 34 | 35 | 42 | 63 | 64 | 65 | 66 | 67 | 68 | 69 |
| Flood | | | | | | | | | | | | | | |
| Barnyardgrass | 30 | 0 | 0 | 0 | 20 | 0 | 0 | 0 | 0 | 0 | 0 | 0 | 20 | 0 |
| Ducksalad | 0 | 0 | 0 | 60 | 85 | 90 | 80 | 35 | 35 | 0 | 0 | 0 | 80 | 70 |
| Rice | 0 | 0 | 0 | 15 | 0 | 15 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

TABLE B-continued

| 250 g ai/ha | Compounds |||||||||||||
| --- | --- | --- | --- | --- | --- | --- | --- | --- | --- | --- | --- | --- | --- |
|  | 1 | 2 | 4 | 5 | 6 | 7 | 8 | 9 | 10 | 11 | 12 | 14 | 15 | 16 |
|  | Flood |||||||||||||
| Barnyardgrass | 0 | 0 | 0 | 0 | 0 | 0 | 0 | 0 | 0 | 0 | 0 | 0 | 0 | 0 |
| Ducksalad | 65 | 0 | 0 | 65 | 0 | 75 | 35 | 30 | 60 | 0 | 20 | 70 | 50 | 30 |
| Rice | 0 | 0 | 0 | 0 | 0 | 0 | 0 | 0 | 0 | 0 | 0 | 0 | 0 | 0 |
| Sedge, Umbrella | 30 | 0 | 0 | 0 | 0 | 0 | 0 | 30 | 40 | 0 | 0 | 20 | 0 | 30 |

| 250 g ai/ha | Compounds |||||||||||||
| --- | --- | --- | --- | --- | --- | --- | --- | --- | --- | --- | --- | --- | --- |
|  | 33 | 36 | 37 | 38 | 39 | 40 | 41 | 43 | 44 | 45 | 46 | 47 | 48 | 49 |
|  | Flood |||||||||||||
| Barnyardgrass | 0 | 60 | 30 | 60 | 0 | 20 | 0 | 50 | 40 | 40 | 0 | 0 | 0 | 0 |
| Ducksalad | 50 | 0 | 100 | 80 | 75 | 70 | 100 | 98 | 90 | 70 | 30 | 0 | 80 | 100 |
| Rice | 0 | 30 | 20 | 0 | 0 | 0 | 20 | 15 | 0 | 15 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds |||||||||||||
| --- | --- | --- | --- | --- | --- | --- | --- | --- | --- | --- | --- | --- | --- |
|  | 50 | 51 | 52 | 53 | 54 | 57 | 58 | 59 | 60 | 61 | 62 | 87 | 88 | 89 |
|  | Flood |||||||||||||
| Barnyardgrass | 0 | 0 | 40 | 30 | 0 | 0 | 0 | 0 | 65 | 40 | 40 | 60 | 0 | 0 |
| Ducksalad | 70 | 40 | 100 | 70 | 0 | 0 | 0 | 0 | 100 | 100 | 100 | 85 | 50 | 70 |
| Rice | 0 | 0 | 0 | 0 | 0 | 0 | 0 | 0 | 0 | 0 | 20 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compound 90 |
| --- | --- |
|  | Flood |
| Barnyardgrass | 0 |
| Ducksalad | 0 |
| Rice | 0 |
| Sedge, Umbrella | 0 |

What is claimed is:

1. A compound selected from Formula 1, N-oxides and salts thereof,

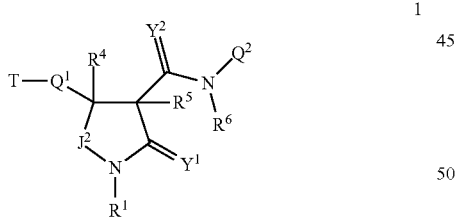

wherein

Q$^1$ is a phenyl ring or a naphthalenyl ring system, each ring or ring system optionally substituted with 1 to 4 substituents independently selected from R$^7$; or a 5- to 6-membered heteroaromatic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from S(=O)$_u$(=NR$^8$)$_v$, each ring or ring system optionally substituted with up to 4 substituents independently selected from R$^7$ on carbon atom ring members and selected from R$^9$ on nitrogen atom ring members;

Q$^2$ is a phenyl ring or a naphthalenyl ring system, each ring or ring system optionally substituted with up to 5 substituents independently selected from R$^{10}$; or a 5- to 6-membered heteroaromatic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from S(=O)$_u$(=NR$^8$)$_v$, each ring or ring system optionally substituted with up to 5 substituents independently selected from R$^{10}$ on carbon atom ring members and selected from R$^{11}$ on nitrogen atom ring members;

T is J$^1$-A-, wherein the free bond projecting to the right next to A indicates the connecting point of J$^1$-A- to Q$^1$; or T is R$^{17}$ON=CR$^{17a}$—, (R$^{18}$)$_2$C=NO—, (R$^{19}$)$_2$NN=CR$^{17a}$—, (R$^{18}$)$_2$C=NNR$^{20a}$—, R$^{20}$N=CR$^{17a}$—, (R$^{18}$)$_2$C=N—, R$^{17}$ON=CR$^{17a}$C(R$^{23b}$)$_2$— or (R$^{18}$)$_2$C=NOC(R$^{24a}$)$_2$—, wherein the free bond projecting to the right indicates the connecting point to Q$^1$;

A is a saturated, partially unsaturated or fully unsaturated chain containing 1 to 3 atoms selected from up to 3 carbon, up to 1 O , up to 1 S and up to 2 N atoms, the chain optionally substituted with up to 2 substituents independently selected from $R^{15}$ on carbon atoms and $R^{16}$ on nitrogen atoms;

$Y^1$ and $Y^2$ are each independently O, S or $NR^{12}$;

$J^1$ is a phenyl ring or a naphthalenyl ring system, each ring or ring system optionally substituted with up to 5 substituents independently selected from $R^{7'}$; or a 4- to 6-membered heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u$ $(=NR^8)_v$, each ring or ring system optionally substituted with up to 5 substituents independently selected from $R^{7'}$ on carbon atom ring members and selected from $R^{9'}$ on nitrogen atom ring members; or $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ haloalkylsulfonyl, $C_2$-$C_8$ alkoxyalkyl, $C_2$-$C_8$ haloalkoxyalkyl, $C_3$-$C_8$ haloalkoxyalkoxy, $C_2$-$C_8$ haloalkoxyhaloalkyl, $C_3$-$C_8$ halocycloalkyl, $C_2$-$C_8$ alkylcarbonyloxy or $C_2$-$C_8$ haloalkylcarbonyloxy;

$J^2$ is —$CR^2R^3$— or —$CR^2R^3$—$CR^{2a}R^{3a}$— wherein —$CR^2R^3$— moiety is connected to N;

$R^1$ is H, hydroxy, amino, cyano, formyl, $C_3$-$C_8$ alkylcarbonylalkyl, —CPh=N—O($C_1$-$C_4$ alkyl), —C($C_1$-$C_4$ alkyl)=N—O($C_1$-$C_4$ alkyl), —C(O)$NH_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl, phenylcarbonyl or $G^1$;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^{2a}$ and $R^{3a}$ are each independently H, halogen or $C_1$-$C_4$ alkyl; or $R^{2a}$ and $R^{3a}$ are taken together with the carbon atom to which they are bonded to form a $C_3$-$C_7$ cycloalkyl ring;

$R^4$ and $R^5$ are each independently H, halogen, hydroxy, $C_1$-$C_4$ alkoxy or $C_1$-$C_4$ alkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^7$ is independently halogen, hydroxy, cyano, nitro, $C_1$-$C_4$ alkyl, $C_1$-$C_4$ cyanoalkyl, $C_1$-$C_4$ cyanoalkoxy, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_3$-$C_8$ alkoxyalkoxyalkyl, $C_2$-$C_4$ haloalkoxyalkyl, $C_3$-$C_4$ cycloalkyl, $C_3$-$C_4$ halocycloalkyl, cyclopropylmethyl, 1-methylcyclopropyl, 2-methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, —CHO, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_4$ trialkylsilyl, trimethylsilylmethyl or trimethylsilylmethoxy; or two adjacent $R^7$ are taken together along with the carbon atoms to which they are bonded to form a $C_3$-$C_7$ cycloalkyl ring;

each $R^{10}$ is independently halogen, hydroxy, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_4$ alkoxyalkyl, $C_3$-$C_8$ alkoxyalkoxyalkyl, $C_1$-$C_4$ cyanoalkyl, $C_1$-$C_4$ cyanoalkoxy, $C_2$-$C_8$ haloalkenyl, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)$NH_2$, $C_2$-$C_8$ alkylaminocarbonyl, $C_4$-$C_{10}$ cycloalkylaminocarbonyl, $C_3$-$C_{10}$ dialkylaminocarbonyl, hydroxy, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, amino, $C_1$-$C_8$ alkylamino, $C_1$-$C_6$ haloalkylamino, $C_3$-$C_8$ cycloalkylamino, $C_2$-$C_8$ dialkylamino, $C_2$-$C_8$ halodialkylamino, formylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, —$SF_5$, —SCN, $C_3$-$C_{12}$ trialkylsilyl, $C_4$-$C_{12}$ trialkylsilylalkyl, $C_4$-$C_{12}$ trialkylsilylalkoxy or $G^2$; or two adjacent $R^{10}$ are taken together along with the carbon atoms to which they are bonded to form a $C_3$-$C_7$ cycloalkyl ring;

each $R^{7'}$ is independently halogen, hydroxy, cyano, nitro, $C_1$-$C_8$ alkyl, $C_2$-$C_4$ alkoxyalkyl, $C_3$-$C_8$ alkoxyalkoxyalkyl, $C_1$-$C_4$ cyanoalkyl, $C_1$-$C_4$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)$NH_2$, $C_2$-$C_8$ alkylaminocarbonyl, $C_4$-$C_{10}$ cycloalkylaminocarbonyl, $C_3$-$C_{10}$ dialkylaminocarbonyl, hydroxy, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, amino, $C_1$-$C_8$ alkylamino, $C_1$-$C_6$ haloalkylamino, $C_3$-$C_8$ cycloalkylamino, $C_2$-$C_8$ dialkylamino, $C_2$-$C_8$ halodialkylamino, formylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, —$SF_5$, —SCN, $C_3$-$C_{12}$ trialkylsilyl, $C_4$-$C_{12}$ trialkylsilylalkyl, $C_4$-$C_{12}$ trialkylsilylalkoxy; or two adjacent $R^{7'}$ are taken together along with the carbon atoms to which they are bonded to form a $C_3$-$C_7$ cycloalkyl ring;

each $R^8$ is independently H, cyano, $C_2$-$C_3$ alkylcarbonyl or $C_2$-$C_3$ haloalkylcarbonyl;

each $R^9$, $R^{9'}$ and $R^{11}$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{12}$ is independently H, cyano, $C_1$-$C_4$ alkyl, $C_1$-$C_4$ haloalkyl, $C_1$-$C_4$ alkoxy, $C_1$-$C_4$ haloalkoxy, —(C=O)$CH_3$ or —(C=O)$CF_3$;

each $G^1$ is independently phenyl, phenylmethyl, pyridinylmethyl, phenylcarbonyl, phenoxy, phenylethynyl, phenylsulfonyl, phenylcarbonylalkyl; or a 5- or 6-membered heteroaromatic ring, each optionally substituted on ring members with up to 5 substituents independently selected from $R^{13}$;

each $G^2$ is independently phenyl, phenylmethyl, pyridinylmethyl, phenylcarbonyl, phenylcarbonylalkyl, phenoxy, phenylethynyl, phenylsulfonyl; or a 5- or 6-membered heteroaromatic ring, each optionally substituted on ring members with up to 5 substituents independently selected from $R^{14}$;

each $R^{13}$ and $R^{14}$ is independently halogen, cyano, hydroxy, amino, nitro, —CHO, —C(=O)OH, —C(=O)$NH_2$, —$SO_2NH_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^{15}$ is independently halogen, cyano, hydroxy, $C_1$-$C_4$ alkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{16}$ is independently cyano, $C_1$-$C_4$ alkyl, $C_1$-$C_4$ haloalkyl, $C_1$-$C_4$ alkoxy, $C_2$-$C_4$ alkylcarbonyl, $C_2$-$C_4$ alkoxycarbonyl or $C_3$-$C_6$ cycloalkyl;

each $R^{17}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{17a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_1$-$C_6$ alkylthio, $C_1$-$C_6$ haloalkylthio, $C_3$-$C_8$ cycloalkylthio, $C_3$-$C_{10}$ trialkylsilyl or $G^1$;

each $R^{18}$ is independently H, hydroxy, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{19}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20}$ is independently H, hydroxy, amino, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy $C_3$-$C_{10}$ trialkylsilyl or $G^1$;

each $R^{23b}$ is independently H, halogen, cyano, hydroxy, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{24a}$ is independently H, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each u and v are independently 0, 1 or 2 in each instance of $S(=O)_u(=NR^8)_v$, provided that the sum of u and v is 0, 1 or 2;

provided that when a) $J^1$ is an unsubstituted phenyl ring, A is other than —$CH_2$—, —O—, —C≡C—, —C(=O)— or —$SO_2$—; or b) $J^1$ is an unsubstituted pyridinyl ring, A is other than —$CH_2$—;

c) $J^1$ is $C_4$-$C_{10}$ cycloalkylalkyl, A is other than alkyl; or d) $J^1$-A- is at the para position of $Q^1$, A is other than O and $J^1$ is other than 2-furanylmethyl.

2. The compound of claim 1 wherein $Q^1$ is a phenyl ring optionally substituted with 1 to 4 substituents independently selected from $R^7$; or a 5- to 6-membered heteroaromatic ring containing ring members selected from carbon atoms and 1 to 4 heteroatoms independently selected from up to 2 O, up to 2 S and up to 4 N atoms, optionally substituted with up to 4 substituents independently selected from $R^7$ on carbon atom ring members and selected from $R^9$ on nitrogen atom ring members;

$Q^2$ is a phenyl ring optionally substituted with up to 5 substituents independently selected from $R^{10}$; or a 5- to 6-membered heteroaromatic ring containing ring members selected from carbon atoms and 1 to 4 heteroatoms independently selected from up to 2 O, up to 2 S and up to 4 N atoms, optionally substituted with up to 5 substituents independently selected from $R^{10}$ on carbon atom ring members and selected from $R^{11}$ on nitrogen atom ring members;

$J^1$ is a phenyl ring optionally substituted with up to 5 substituents independently selected from $R^{7'}$; or a 4- to 6-membered heterocyclic ring containing ring members selected from carbon atoms and 1 to 4 heteroatoms independently selected from up to 2 O, up to 2 S and up to 4 N atoms, optionally substituted with up to 5 substituents independently selected from $R^{7'}$ on carbon atom ring members and selected from $R^{9'}$ on nitrogen atom ring members;

$R^1$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl or $C_4$-$C_8$ cycloalkylalkyl; and A is a saturated, partially unsaturated or fully unsaturated chain containing 2- to 3-atoms selected from up to 3 carbon, up to 1 O, up to 1 S and up to 1 N atom, the chain optionally substituted with up to 2 substituents independently selected from $R^{15}$ on carbon atoms and $R^{16}$ on nitrogen atoms.

3. The compound of claim 1 wherein $Q^1$ is a phenyl ring or a naphthalenyl ring system, each ring or ring system optionally substituted with 1 to 4 substituents independently selected from $R^7$;

$Q^2$ is a phenyl ring optionally substituted with 1 to 5 substituents independently selected from $R^{10}$; and $J^1$ is a phenyl ring or a naphthalenyl ring system, each ring or ring system optionally substituted with up to 4 substituents independently selected from $R^{7'}$.

4. The compound of claim 3 wherein

A is —$CH_2$—, —$CH_2O$—, —$CH_2NH$—, —CH=CH—, —C≡C—, —NH—, —O—, —S—, —SO— or —$SO_2$—;

each $R^7$ is independently halogen, cyano, $C_1$-$C_2$ alkyl, $C_1$-$C_3$ haloalkyl or $C_1$-$C_3$ alkylsulfonyl;

each $R^{10}$ is independently halogen, cyano, nitro, $C_1$-$C_2$ alkyl, $C_1$-$C_3$ haloalkyl or $C_1$-$C_3$ alkylsulfonyl;

each $R^{7'}$ is independently halogen, cyano, nitro, $C_1$-$C_8$ alkyl or $C_1$-$C_8$ haloalkyl;

$Y^1$ and $Y^2$ are both O.

5. The compound of claim 1 wherein $Q^1$ is a phenyl ring or a naphthalenyl ring system, each ring or ring system optionally substituted with 1 to 4 substituents independently selected from $R^7$;

$Q^2$ is a phenyl ring optionally substituted with 1 to 5 substituents independently selected from $R^{10}$; and $J^1$ is a 4- to 6-membered heterocyclic ring containing ring members selected from carbon atoms and 1 to 3 heteroatoms independently selected from up to 2 O, up to 2 S and up to 3 N atoms, wherein up to 2 carbon ring members are independently selected from C(=O) and C(=S), and the sulfur atom ring members are independently selected from $S(=O)_u(=NR^8)_v$, each ring or ring system optionally substituted with up to 3 substituents independently selected from $R^{7'}$ on carbon atom ring members and selected from $R^{9'}$ on nitrogen atom ring members.

6. The compound of claim 5 wherein

A is —$CH_2$—, —$CH_2O$—, —$CH_2NH$—, —CH=CH—, —C≡C—, —NH—, —O—, —S—, —SO— or —$SO_2$—;

each $R^7$ is independently halogen, cyano, $C_1$-$C_2$ alkyl, $C_1$-$C_3$ haloalkyl or $C_1$-$C_3$ alkylsulfonyl;

each $R^{10}$ is independently halogen, cyano, nitro, $C_1$-$C_2$ alkyl, $C_1$-$C_3$ haloalkyl or $C_1$-$C_3$ alkylsulfonyl;

each $R^{7'}$ is independently halogen, cyano, nitro, $C_1$-$C_8$ alkyl or $C_1$-$C_8$ haloalkyl; and $Y^1$ and $Y^2$ are both O.

7. The compound of claim 1 wherein $Q^1$ is a 5- to 6-membered heteroaromatic ring or an 8- to 10-membered heteroaromatic bicyclic ring system, each ring or ring system optionally substituted with up to 4 substituents independently selected from $R^7$ on carbon atom ring members and selected from $R^9$ on nitrogen atom ring members;

$Q^2$ is a phenyl ring optionally substituted with 1 to 5 substituents independently selected from $R^{10}$; and $J^1$ is a 4- to 6-membered heterocyclic ring containing ring members selected from carbon atoms and 1 to 3 heteroatoms independently selected from up to 2 O, up to 2 S and up to 3 N atoms, wherein up to 2 carbon ring members are independently selected from C(=O) and C(=S), and the sulfur atom ring members are independently selected from $S(=O)_u(=NR^8)_v$, each ring or ring system optionally substituted with up to 3 substituents independently selected from $R^{7'}$ on carbon atom ring members and selected from $R^{9'}$ on nitrogen atom ring members.

8. The compound of claim 7 wherein

A is —$CH_2$—, —$CH_2O$—, —$CH_2NH$—, —CH=CH—, —C≡C—, —NH—, —O—, —S—, —SO— or —$SO_2$—;

each $R^7$ is independently halogen, cyano, $C_1$-$C_2$ alkyl, $C_1$-$C_3$ haloalkyl or $C_1$-$C_3$ alkylsulfonyl;

each $R^{10}$ is independently halogen, cyano, nitro, $C_1$-$C_2$ alkyl, $C_1$-$C_3$ haloalkyl or $C_1$-$C_3$ alkylsulfonyl;

each $R^{7'}$ is independently halogen, cyano, nitro, $C_1$-$C_8$ alkyl or $C_1$-$C_8$ haloalkyl; and $Y^1$ and $Y^2$ are both O.

9. The compound of claim 1 wherein $Q^1$ is a 5- to 6-membered heteroaromatic ring or an 8- to 10-membered heteroaromatic bicyclic ring system, each ring or ring system optionally substituted with up to 4 substituents independently selected from $R^7$ on carbon atom ring members and selected from $R^9$ on nitrogen atom ring members;

$Q^2$ is a phenyl ring optionally substituted with 1 to 5 substituents independently selected from $R^{10}$; and $J^1$ is a phenyl ring or a naphthalenyl ring system, each ring or ring system optionally substituted with up to 4 substituents independently selected from $R^{7'}$.

10. The compound of claim 9 wherein

A is —$CH_2$—, —$CH_2O$—, —$CH_2NH$—, —CH=CH—, —C≡C—, —NH—, —O—, —S—, —SO— or —$SO_2$—;

each $R^7$ is independently halogen, cyano, $C_1$-$C_2$ alkyl, $C_1$-$C_3$ haloalkyl or $C_1$-$C_3$ alkylsulfonyl;

each $R^{10}$ is independently halogen, cyano, nitro, $C_1$-$C_2$ alkyl, $C_1$-$C_3$ haloalkyl or $C_1$-$C_3$ alkylsulfonyl;

each $R^{7'}$ is independently halogen, cyano, nitro, $C_1$-$C_8$ alkyl or $C_1$-$C_8$ haloalkyl; and $Y^1$ and $Y^2$ are both O.

11. The compound of claim 1 selected from the group consisting of

N-(2,4-difluorophenyl)-2-oxo-4-[3-(phenoxymethyl)phenyl]-3-pyrrolidinecarboxamide; and 2-oxo-4-[3-(2-pyridinyloxy)phenyl]-N-(2,3,4-trifluorophenyl)-3-pyrrolidinecarboxamide.

12. A herbicidal composition comprising a compound of claim 1 and at least one component selected from the group consisting of surfactants, solid diluents and liquid diluents.

13. A herbicidal composition comprising a compound of claim 1, at least one additional active ingredient selected from the group consisting of other herbicides and herbicide safeners, and at least one component selected from the group consisting of surfactants, solid diluents and liquid diluents.

14. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides selected from mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

15. A method for controlling the growth of undesired vegetation comprising contacting the vegetation or its environment with a herbicidally effective amount of a compound of claim 1.

* * * * *